(12) United States Patent
Yu et al.

(10) Patent No.: US 8,426,677 B2
(45) Date of Patent: *Apr. 23, 2013

(54) METHOD OF CONTROLLING PLANT GROWTH AND ARCHITECTURE BY CONTROLLING EXPRESSION OF GIBBERELLIN 2-OXIDASE

(75) Inventors: Su-May Yu, Taipei (TW); Shuen-Fang Lo, Dali (TW); Liang-Jwu Chen, Taichung (TW); Tuan-Hua David Ho, Chesterfield, MO (US)

(73) Assignee: Academia Sinica, Taipei (TW)

( * ) Notice: Subject to any disclaimer, the term of this patent is extended or adjusted under 35 U.S.C. 154(b) by 361 days.

This patent is subject to a terminal disclaimer.

(21) Appl. No.: 12/604,808

(22) Filed: Oct. 23, 2009

(65) Prior Publication Data

US 2010/0095406 A1    Apr. 15, 2010

Related U.S. Application Data

(63) Continuation-in-part of application No. 12/139,674, filed on Jun. 16, 2008, now Pat. No. 8,034,992.

(51) Int. Cl.
*A01H 5/00* (2006.01)
*A01H 1/00* (2006.01)
*C07H 21/04* (2006.01)
*C12N 5/04* (2006.01)
*C12N 15/05* (2006.01)

(52) U.S. Cl.
USPC ........ 800/278; 800/298; 435/320.1; 435/410; 435/252.3; 536/23.6

(58) Field of Classification Search .................. None
See application file for complete search history.

(56) References Cited

U.S. PATENT DOCUMENTS

| | | |
|---|---|---|
| 6,670,527 B1 | 12/2003 | Thomas et al. |
| 6,723,897 B2 | 4/2004 | Brown et al. |
| 6,921,849 B2 | 7/2005 | Amasino et al. |
| 7,154,028 B2 | 12/2006 | Tanaka et al. |
| 7,186,891 B1 | 3/2007 | Chappell et al. |
| 7,195,917 B2 | 3/2007 | Brown et al. |
| 7,262,340 B2 | 8/2007 | Thomas et al. |
| 8,034,992 B2 * | 10/2011 | Yu et al. .......... 800/278 |
| 2006/0123505 A1 | 6/2006 | Kikuchi et al. |
| 2009/0313725 A1 | 12/2009 | Yu et al. |

FOREIGN PATENT DOCUMENTS

WO        2009064118 A2    5/2009

OTHER PUBLICATIONS

Int'l Search Report issued Jun. 8, 2011 in Int'l Application No. PCT/US2010/053786; Written Opinion.
Biemelt et al, "Impact of altered gibberellin metabolism on biomass accumulation, lignin biosynthesis, and photosynthesis in transgenic tobacco plants", Plant Physiology, vol. 135, No. 1, pp. 254-265 (2004).
Magome et al, "The DDF1 transcriptional activator upregulates expression of a gibberellin-deactivating gene, Ga2ox7, under high-salinity stress in *Arabidopsis*", The Plant Journal, vol. 56, No. 4, pp. 613-626 (2008).
Office Action issued Jan. 12, 2011 in U.S. Appl. No. 12/139,674.
Database UniProt, Accession No. Q0IIA8, Nov. 14, 2006.
Dong Ju Lee et al.; Molecular Cloning of GA 2-Oxidase3 from Spinach and Its Ectopic Expression in *Nicotiana sylvestris*; Plant Physiology, May 2005, vol. 138, pp. 243-254; American Society of Plant Biologists.
Miho Sakai et al.; Expression of novel rice gibberellin 2-oxidase gene is under homeostatic regulation by biologically active gibberellins; J Plant Res (2003) 116; pp. 161-164; The Botanical Society of Japan and Springer-Verlag, Tokyo 2003.
Tomoaki Sakamoto et al.; An Overview of Gibberellin Metabolism Enzyme Genes and Their Related Mutants in Rice; Plant Physiology, Apr. 2004, vol. 134, pp. 1642-1653; American Society of Plant Biologists.
Tomoaki Sakamoto et al.; Genetic Manipulation of Gibberellin Metabolism in Transgenic Rice; Nature Biotechnology; vol. 21, No. 8; Aug. 2003; Nature Publishing Group.
Tomoaki Sakamoto et al.; Expression of a Gibberellin 2-Oxidase Gene around the Shoot Apex Is Related to Phase Transition in Rice; Plant Physiology; Mar. 2001; vol. 125, pp. 1508-1516; American Society of Plant Biologists.
A print out from Wikipedia of "T-DNA"; retrieved from "http://en.wikipedia.org/wiki/T-DNA"; 1 page, Dec. 7, 2007.
Shuen-Fang Lo et al; A Novel Class of Gibberellin 2-Oxidases Control Semidwarfism, Tillering, and Root Development in Rice; The Plant Cell, vol. 20: 2603-2618; Oct. 2008; American Society of Plant Biologists.

* cited by examiner

*Primary Examiner* — Eileen B O Hara
(74) *Attorney, Agent, or Firm* — Panitch Schwarze Belisario & Nadel LLP

(57) ABSTRACT

Novel gibberellin 2-oxidase (GA2ox) genes were identified. Differential expression of GA2ox genes correlated with flower development, seed germination, tiller growth and other developmental processes. In addition, the early and increased growth of tiller and adventitious root and altered root architecture caused by overexpression of GA2oxs further suggest the pleiotropic role of GA2oxs in controlling growth and architecture in plants such as rice. GA2ox5, GA2ox6 and GA2ox9 were three genes encoding class C20 GA2oxs in rice. Mutants or transgenic rice overexpressing class C20 GA2oxs exhibited a broad range of mutant phenotypes, including semi-dwarfism, increased root system and higher tiller numbers that may favor grain yield. Mutations in the conserved domain III were found to affect the physiological activity of class C20 GA2oxs. Methods are described for controlling plant growth and architecture by controlling gene expression of gibberellin 2-oxidase in the plant.

20 Claims, 17 Drawing Sheets

METHOD OF CONTROLLING PLANT GROWTH AND ARCHITECTURE BY CONTROLLING EXPRESSION OF GIBBERELLIN 2-OXIDASE

REFERENCE TO RELATED APPLICATIONS

This application is a continuation-in-part patent application of U.S. patent application Ser. No. 12/139,674, filed on Jun. 16, 2008, titled "Gibberellin 2-Oxidase Genes And Uses Thereof," which is hereby incorporated by reference herein in its entirety.

BACKGROUND OF THE INVENTION

Gibberellins (GAs) are a class of essential hormones controlling a variety of growth and development processes during the entire life cycle of plants, including seed germination, apical dominance, leaf expansion, stem elongation, root growth, floral initiation, another development and fruit maturation (Harberd et al., 1998; Ross et al., 1997; Hedden and Phillips, 2000, Kin and Evan, 2003, Sun and Gubler, 2004; Kende and Zeevaart, 1997, del Pozo, et al., 2005). GAs are substituted tetracyclic diterpene carboxylic acids formed over several biosynthetic steps (Hedden and Phillips, 2000). To date, 136 different GAs have been identified in plants, fungi and bacteria (see for example, the World Wide Web site of plant-hormones.info/gibberellins); however, most of these GAs are precursors or degradation products.

The bioactive GAs synthesized by higher plants are $GA_1$, $GA_3$, $GA_4$, and $GA_7$ (Hedden and Phillips, 2000). The GA biosynthetic pathway can be classified into three stages, with three classes of enzymes involved, including terpene cyclases, cytochrome P450 monooxygenases (CYP450s), and 2-oxoglutarate-dependent dioxygenases (2-ODDs, including GA 20-oxidase, GA 7-oxidase, GA 3-oxidase, and GA 2-oxidase) (Olszewski et al., 2002; Graebe, 1987, Hedden and Phillip, 2000, Sakamoto et al., 2004). Mutants defective in GA biosynthesis have been identified in a variety of plant species, with the most prominent phenotypes being reduced internode length and small dark green leaves (Koornneef and van der Veen, 1980). Other phenotypes include prolonged germination dormancy, inhibited root growth, defective flowering, reduced seed production, and male sterility (King and Evans, 2003, Sakamoto et al., 2004, Tanimoto, 2005, Wang and Li, 2005). Normal growth of these mutants can be restored by exogenous application of active GAs.

GA 2-oxidases (GA2oxs) are a class of 2-ODDs (Thomas, et al., 1999; Sakamoto, et al., 2001, Schomburg, et al., 2003, Sakamoto et al., 2004, Lee and Zeevaart, 2005). The class C19 GA2oxs identified in various plant species can hydroxylate the C-2 of active $C_{19}$-GAs ($GA_1$ and $GA_4$) or $C_{19}$-GA precursors ($GA_{20}$ and $GA_9$) to produce biologically inactive GAs ($GA_8$, $GA_{34}$, $GA_{29}$, and $GA_{51}$, respectively) (Sakamoto et al., 2004). Recently, three novel class C20 GA2oxs, including Arabidopsis GA2ox7 and GA2ox8 and spinach GA2ox3, were found to hydroxylate $C_{20}$-GA precursors (converting $GA_{12}$ and $GA_{53}$ to $GA_{110}$ and $GA_{97}$, respectively) but not $C_{19}$-GAs (Schomburg et al., 2003, Lee and Zeevaart, 2005). The 2β-hydroxylation of $C_{20}$-GA precursors to $GA_{110}$ and $GA_{97}$ renders them unable to be converted to active GAs and thus decreases active GA levels. The class C20 GA2oxs contain three unique and conserved amino acid domains that are absent in the class C19 GA2oxs (Lee and Zeevaart, 2005).

The physiological function of GA2oxs has been studied in a variety of plant species. Arabidopsis GA2ox 1 and GA2ox2 were found to be expressed in inflorescences and developing siliques, which is consistent with a role of GA2oxs in reducing GA levels and promoting seed dormancy (Thomas et al., 1999). Further study with the pea slender mutant, where the SLENDER gene encoding a GA2ox had been knocked out, showed that GA level increased during germination, and resultant seedlings were hyperelongated (Martin et al., 1999). More recently, dwarf phenotype was also found to correlate with reduced GA levels in two Arabidopsis mutants in which GA2ox7 and GA2ox8 were activation-tagged, and ectopic overexpression of these two genes in transgenic tobacco led to dwarf phenotype (Schomburg et al., 2003). These studies demonstrated that GA2oxs are responsible for reducing the endogenous level of biologically active GAs in plants. The class C20 GA2oxs, regulating early steps in the GA biosynthesis pathway, have also been shown to control photoperiods in dicots. In long-day (LD) rosette plants, such as spinach, LD-induced stem elongation and flowering are dependent on GA-regulated processes. In short-day (SD) plants, deactivation of $GA_{53}$ to $GA_{97}$ prevails, while in LD plants, conversion of $GA_{53}$ to the bioactive $GA_{20}$ and $GA_1$ is favored (Lee and Zeevaart, 2005). The functions of four rice GA2oxs have been previously studied (Sakamoto, et al., 2001, 2004; Sakai et al., 2003).

U.S. patent application Ser. No. 12/139,674 describes the identification and characterization of 10 putative GA2ox genes from the sequence analysis of the rice genome. Differential expression of the GA2ox genes was found to correlate with various developmental processes during rice growth, such as flower development, seed germination and tiller growth. The application also describes methods related to GA2ox genes, such as a method of inhibiting stem elongation and promoting tiller growth in a plant by controlling the expression of a GA2ox gene in a plant.

Features such as semidwarfism, higher finding, more biomass, more adventitious roots, stronger stems and enhanced stress tolerance are the most valuable traits in crop breeding, because they result in plants that are more resistant to damages caused by wind and rain (lodging resistant) and biotic and abiotic stresses, and have stable increase of yields. However, it is difficult to create such plant varieties by conventional breeding of the natural genetic variations of crops species. The present invention offers transgenic approaches for obtaining plants with desirable traits that have not been easily obtained with conventional breeding methods, i.e., by controlling expression of GA2ox gene in both monocots and dicots. Plants with more adventitious roots, thicker or stronger stems and branches, more leaf numbers or more biomass, and higher stress tolerance, as well as plants with semidwarfism and higher tillering, have been obtained using the present invention.

SUMMARY OF THE INVENTION

In one general aspect, the present invention relates to a method of generating a transgenic plant having one or more features selected from the group consisting of reduced height, increased tillering number, more biomass, a stronger and thicker stem, a stronger root system, more leaves, stable increase of yields and/or or seed production, and enhanced stress tolerance, than a plant of substantially the same genetic background grown under the same conditions. The method comprises:
 (a) transforming a cell of the plant of substantially the same genetic background with a nucleic acid molecule to obtain a recombinant plant cell;
 (b) generating a transgenic plant from the recombinant plant cell, wherein the transgenic plant recombinantly expresses a polypeptide selected from the group consisting of:

(1) a polypeptide having an amino acid sequence that is at least about 80% identical to SEQ ID NO:2, wherein the amino acid sequence has a domain that is at least 80% identical to SEQ ID NO:70;

(2) a polypeptide having an amino acid sequence that is at least about 80% identical to SEQ ID NO:4, wherein the amino acid sequence has a domain that is at least 80% identical to SEQ ID NO:71;

(3) a polypeptide having an amino acid sequence that is at least about 80% identical to SEQ ID NO:6, wherein the amino acid sequence has a domain that is at least 80% identical to SEQ ID NO:72;

(4) a polypeptide having an amino acid sequence that is at least about 80% identical to SEQ ID NO:8, wherein the amino acid sequence has a domain that is at least 80% identical to SEQ ID NO:73;

(5) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74;

(6) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75; and (7) a mutant class C20 GA2ox, the mutant C20 GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, and the domain III comprising the amino acid sequence of SEQ ID NO:17.

Another general aspect of the present invention relates to a method of improving one or more traits of a plant selected from the group consisting of reduced height, increased filleting number, more biomass, a stronger and thicker stem, a stronger root system, more leaves, stable increase of yields and/or seed production and enhanced stress tolerance. The method comprises increasing expression and/or activity of a gibberellin 2-oxidase or a derivative thereof in the plant.

In an embodiment of the present invention, the expression and/or activity of the Gibberellin 2-oxidase or a derivative thereof are increased by recombinant expression in the plant of a polypeptide selected from the group consisting of:

(1) a polypeptide having an amino acid sequence that is at least about 80% identical to SEQ ID NO:2, wherein the amino acid sequence has a domain that is at least 80% identical to SEQ ID NO:70;

(2) a polypeptide having an amino acid sequence that is at least about 80% identical to SEQ ID NO:4, wherein the amino acid sequence has a domain that is at least 80% identical to SEQ ID NO:71;

(3) a polypeptide having an amino acid sequence that is at least about 80% identical to SEQ ID NO:6, wherein the amino acid sequence has a domain that is at least 80% identical to SEQ ID NO:72;

(4) a polypeptide having an amino acid sequence that is at least about 80% identical to SEQ ID NO:8, wherein the amino acid sequence has a domain that is at least 80% identical to SEQ ID NO:73;

(5) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74;

(6) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75; and (7) a mutant class C20 GA2ox, the mutant GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, and the domain III comprising the amino acid sequence of SEQ ID NO:17.

In one general aspect, the present invention relates to an isolated nucleic acid comprising a nucleotide sequence that encodes a polypeptide selected from the group consisting of:

(a) a polypeptide having an amino acid sequence that is at least about 80% identical to SEQ ID NO:6, wherein the amino acid sequence has a domain that is at least 80% identical to SEQ ID NO:72;

(b) a polypeptide having an amino acid sequence that is at least about 80% identical to SEQ ID NO:8, wherein the amino acid sequence has a domain that is at least 80% identical to SEQ ID NO:73;

(c) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74; and (d) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75.

In another general aspect, the present invention relates to an isolated polypeptide comprising an amino acid sequence selected from the group consisting of:

(1) an amino acid sequence that is at least about 80% identical to SEQ ID NO:6, wherein the amino acid sequence has a domain that is at least 80% identical to SEQ ID NO:72;

(2) an amino acid sequence that is at least about 80% identical to SEQ ID NO:8, wherein the amino acid sequence has a domain that is at least 80% identical to SEQ ID NO:73;

(3) an amino acid sequence that is at least about 80% identical to SEQ ID NO:10 or at least about 80% identical to SEQ ID NO:12, wherein the amino acid sequence has a domain that is at least 80% identical to SEQ ID NO:74; and (4) an amino acid sequence that is at least about 80% identical to SEQ ID NO:14 or at least about 80% identical to SEQ ID NO:16, wherein the amino acid sequence has a domain that is at least 80% identical to SEQ ID NO:75.

Another general aspect of the present invention relates to an isolated nucleic acid comprising a nucleotide sequence that encodes a mutant class C20 gibberellin 2-oxidase protein (GA2ox), the mutant GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, wherein the domain III comprises an amino acid sequence of SEQ ID NO:17.

Another general aspect of the present invention relates to an isolated polypeptide comprising a mutant class C20 gibberellin 2-oxidase (GA2ox), the mutant GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, wherein the domain III comprises the amino acid sequence of SEQ ID NO:17.

Other general aspects of the present invention relate to an expression vector and a recombinant cell comprising a nucleic acid according to an embodiment of the present invention.

In another general aspect, the present invention relates to a transgenic plant comprising a transgene, wherein the transgene encodes a polypeptide selected from the group consisting of:
 (a) a polypeptide having an amino acid sequence that is at least about 80% identical to SEQ ID NO:2, wherein the amino acid sequence has a domain that is at least 80% identical to SEQ ID NO:70;
 (b) a polypeptide having an amino acid sequence that is at least about 80% identical to SEQ ID NO:4, wherein the amino acid sequence has a domain that is at least 80% identical to SEQ ID NO:71;
 (c) a polypeptide having an amino acid sequence that is at least about 80% identical to SEQ ID NO:6, wherein the amino acid sequence has a domain that is at least 80% identical to SEQ ID NO:72;
 (d) a polypeptide having an amino acid sequence that is at least about 80% identical to SEQ ID NO:8, wherein the amino acid sequence has a domain that is at least 80% identical to SEQ ID NO:73;
 (e) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74;
 (f) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75; and
 (g) a mutant class C20 GA2ox, the mutant GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, and the domain III comprising the amino acid sequence of SEQ ID NO:17.

The present invention also relates to a propagation material obtained from the transgenic plant of the present invention, wherein the propagation material contains the transgene.

In another general aspect, the present invention relates to a method of producing a transgenic plant according to embodiments of the present invention, comprising:
 (a) transforming a plant cell with a nucleic acid molecule comprising a transgene according to an embodiment of the present invention to obtain a recombinant plant cell; and
 (b) growing the recombinant plant cell obtained in (a) to generate a transgenic plant.

Another general aspect of the present invention relates to a method of inhibiting plant growth, comprising:
 (a) transforming a plant cell with a nucleic acid molecule comprising a transgene according to an embodiment of the present invention to obtain a recombinant plant cell that expresses a recombinant polypeptide; and
 (b) growing the recombinant plant cell obtained in (a) to generate a transgenic plant;
 wherein the recombinant polypeptide is expressed in the transgenic plant at a level sufficient to inhibit growth of the transgenic plant.

Another general aspect of the present invention relates to a method of obtaining a semi-dwarf transgenic plant, comprising:
 (a) providing a transgenic plant according to an embodiment of the present invention or a propagation material thereof;
 (b) growing the transgenic plant or the propagation material thereof, so that a recombinant polypeptide is expressed in the transgenic plant at a level sufficient to inhibit growth of the transgenic plant; and
 (c) applying to the transgenic plant or the propagation material thereof a composition comprising at least one bioactive GA compound, so that the transgenic plant or propagation material thereof produces the semi-dwarf transgenic plant.

Another general aspect of the present invention relates to a method of inhibiting stem elongation and promoting tiller growth in a plant, comprising administering to the plant a compound that increases the expression of a gene encoding a polypeptide or a compound that increases the enzymatic activity of the polypeptide in the plant, wherein the polypeptide is selected from the group consisting of:
 (a) a polypeptide having an amino acid sequence that is at least about 80% identical to SEQ ID NO:2, wherein the amino acid sequence has a domain that is at least 80% identical to SEQ ID NO:70;
 (b) a polypeptide having an amino acid sequence that is at least about 80% identical to SEQ ID NO:4, wherein the amino acid sequence has a domain that is at least 80% identical to SEQ ID NO:71;
 (c) a polypeptide having an amino acid sequence that is at least about 80% identical to SEQ ID NO:6, wherein the amino acid sequence has a domain that is at least 80% identical to SEQ ID NO:72;
 (d) a polypeptide having an amino acid sequence that is at least about 80% identical to SEQ ID NO: 8, wherein the amino acid sequence has a domain that is at least 80% identical to SEQ ID NO:73;
 (e) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74; and
 (f) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75.

Another general aspect of the present invention relates to a method of identifying a compound that inhibits stem elongation and promotes tiller growth in a plant, comprising identifying a compound that increases the expression of a gene encoding a polypeptide or a compound that increases the enzymatic activity of the polypeptide in the plant, wherein the polypeptide is selected from the group consisting of:
 (a) a polypeptide having an amino acid sequence that is at least about 80% identical to SEQ ID NO:2, wherein the amino acid sequence has a domain that is at least 80% identical to SEQ ID NO:70;
 (b) a polypeptide having an amino acid sequence that is at least about 80% identical to SEQ ID NO:4, wherein the amino acid sequence has a domain that is at least 80% identical to SEQ ID NO:71;

(c) a polypeptide having an amino acid sequence that is at least about 80% identical to SEQ ID NO:6, wherein the amino acid sequence has a domain that is at least 80% identical to SEQ ID NO:72;

(d) a polypeptide having an amino acid sequence that is at least about 80% identical to SEQ ID NO:8, wherein the amino acid sequence has a domain that is at least 80% identical to SEQ ID NO:73;

(e) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74; and (f) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawing. For the purpose of illustrating the invention, there is shown in the drawing embodiments of the invention. It should be understood, however, that the invention is not limited to the precise arrangements and instrumentalities shown.

In the drawings:

FIG. 1A shows chromosome locations of GA2oxs as determined by the NCBI map viewer program (www.ncbi.nlm.nih.gov/mapview/); FIG. 1B shows the phylogenetic tree based on the comparison of deduced amino acid sequences of rice GA2oxs; FIG. 1C shows the phylogenetic tree based on the comparison of amino acid sequences of 29 GA2oxs from 9 plant species (Table 4); wherein the plant species are: At, *Arabidopsis thaliana*; Cm, *Cucurbita maxima*; Ls, *Lactuca sativa*; Nt, *Nicotiana sylvestris*; Pc, *Phaseolus coccineus*; Po, *Populus alba* x *P. tremuloides*; Ps, *Pisum sativum*; and So, *Spinacia oleracea*; wherein GA2oxs with three unique highly conserved domains are enclosed in squares;

FIG. 2A shows various developmental phases during the life cycle of rice; FIG. 2B shows temporal expression patterns of GA2oxs in rice, wherein the 18S rRNA gene (rRNA) was used as a control; FIG. 2C shows tiller development during the life cycle of rice, wherein a total of 8 plants were used for counting tiller number and error bars indicate the SE (standard errors) of the mean at each time point, and DAI means days after imbibition;

FIG. 3A shows that germination rate of rice seeds reached 100% at 2 DAI; FIG. 3B shows expression patterns of GA2oxs in rice seeds between 0~5 DAI, wherein total RNAs were isolated from embryos at each time point and analyzed by RT-PCR, and wherein the 18S rRNA gene (rRNA) was used as a control;

FIG. 4A shows the severely dwarf mutant M77777, designated as GA2ox3$_{ACT}$, which carries a T-DNA insertion at a position 587 by upstream of the translation start codon of GA2ox3, wherein accumulation of GA2ox3 mRNA in this mutant was significantly enhanced in the heterozygous (T/W) mutant as analyzed by RT-PCR analysis; FIG. 4B shows the semi-dwarf mutant M27337, designated as GA2ox5Δ335-341$_{ACT}$, which carries a T-DNA insertion in the coding region, at a position 23 bp upstream of the translation stop codon of GA2ox5, wherein accumulation of the truncated GA2ox5 mRNA was significantly enhanced by T-DNA activation tagging in both heterozygous and homozygous (T/T) mutants; FIG. 4C shows the severely dwarf mutant M47191, designated as GA2ox6$_{ACT}$, which carries a T-DNA insertion at a position 2.1 kb upstream of the translation start codon of GA2ox6, wherein accumulation of GA2ox6 mRNA was significantly enhanced by T-DNA activation tagging in both heterozygous and homozygous mutants; and FIG. 4D shows the semi-dwarf mutant M58817, designated as GA2ox9$_{ACT}$, which carries a T-DNA insertion at a position 2.4 kb upstream of the translation start codon of GA2ox9, wherein accumulation of GA2ox9 mRNA was significantly enhanced by T-DNA activation tagging in the homozygous mutant; wherein in the diagram, an asterisk indicates translation start codon, filled box indicates exon, triangle indicates T-DNA, arrowheads indicate position of primers used for RT-PCR analysis, and scale bar represents DNA length for each gene, and the open box in the triangle indicates the position of the CaMV35S enhancers (next to the left border of T-DNA);

FIG. 5A shows morphology of T1 seedlings at 18 DAI; FIG. 5B shows that seedling heights of GA2ox5Δ335-341$_{ACT}$ and GA2ox9$_{ACT}$ mutants were slightly shorter while seedlings of GA2ox6$_{ACT}$ were severely shorter than the wild type, wherein heights of 8 plants in each line were measured and error bars indicate the SE of the mean at each time point; FIG. 5C shows that as compared with the wild type, germination rate was normal for GA2ox9$_{ACT}$ mutant, slightly delayed for GA2ox5Δ335-341$_{ACT}$ mutant, and significantly delayed for GA2ox6$_{ACT}$ mutant; wherein germination rates of 154, 20, 156, 49 seeds for TNG67, GA2ox5Δ335-341$_{ACT}$, GA2ox6$_{ACT}$, and GA2ox9$_{ACT}$, respectively, were determined at each time point, and + and − indicate the presence and absence, respectively;

FIGS. 6A and 6B show that expression of Ubi:: GA2ox5 and Ubi::GA2ox6, respectively, resulted in dwarfism in transgenic rice as compared with control rice transformed with vector pCAMBIA1301 only (CK); FIGS. 6C and 6D show that expression of Ubi::GA2ox5 and Ubi::GA2ox6, respectively, resulted in different degrees of dwarfism in transgenic tobacco as compared with control tobacco transformed with vector only (CK); wherein photographs were taken at the heading stage (upper panel) and 18 days (lower panel) after sowing of seeds;

FIG. 7A shows that treatment with GA$_3$ (5 μM) promoted germination and seedling growth of GA2ox6$_{ACT}$ mutant (photo taken at 6 DAI); FIG. 7B shows that overexpression of GA2ox6 in rice mutants reduced shoot but not root growth, wherein treatment with GA$_3$ (5 μM) recovered plant height of the GA2ox6$_{ACT}$ mutant and root growth of both wild type and mutant, and a total of 8 plants were used for measuring plant height and root length and error bars indicate the SE of the mean; FIG. 7C illustrates that accumulation of GA2ox6 mRNA in leaves and roots of wild type and mutant seedlings (at 18 DAI) was not altered by $GA_3$ treatment, wherein the 18S rRNA gene (rRNA) was used as a control, and WT stands for wild type;

FIGS. 8A-8F illustrate that overexpression of GA2ox5 and GA2ox6 promoted early tiller and adventitious root growth and affects root architecture: FIG. 8A shows that swelling on the embryo surface adjacent to the base of the first seedling/tiller (1T) was observed in the GA2ox6$_{ACT}$ mutant and Ubi:: OsGA2ox5 and Ubi:: OsGA2ox6 transgenic rice (panels 2-4) and not in the wild type (panel 1) (photos taken at 3 DAI); FIG. 8C shows that three tillers formed in some seedlings of mutant and transgenic rice (photo taken at 15 DAI); FIG. 8D shows that each tiller grew out of its own coleoptile and all new tillers in the mutant and transgenic rice had their own adventitious roots (photo taken at 21 DAI), wherein panel 2 is a higher magnification of the boxed area in panel 1 that reveals coleoptiles (1C and 2C, respectively) and adventitious roots (1R and 2R, respectively) of the first and second tillers; FIG. 8E shows dwarfism and early tillering of seedlings of mutant and transgenic rice as compared with the wild type (photo taken at 12 DAI), wherein panel 2 is a higher magnification of the boxed area in panel 1 that reveals first and second tillers; FIG. 8F shows that mutant and transgenic roots became highly curled and zigzag (panel 2) as compared with the wild type (panel 1), wherein photos were taken at 15 DAI from the bottom of agar plates for better visualization of root growth and WT stands for wild type.

FIG. 9A shows plant heights of various plants; FIG. 9B shows tiller of various plants; FIG. 9C shows root numbers of various plants; wherein mutant or transgenic rice seeds germinated on MS agar medium for 18 DAI, ten plants in each line were averaged and error bars indicate the SE of the mean, and wherein WT stands for wild type;

FIG. 10A shows design of constructs encoding the full-length and domain III-truncated GA2ox5 and GA2ox6, wherein boxes indicate positions of three highly conserved amino acid domains, and the last amino acid residue was shown at the C-terminus of deduced polypeptides; FIG. 10B shows the comparison of morphology among transgenic rice overexpressing full-length and domain-III-truncated GA2ox5 and GA2ox6 and vector pCAMBIA1301 only (CK);

FIG. 12A shows morphology of plants, and FIG. 12B shows growth curve of plants; the height of transgenic plants increased linearly during first 10 days, tapered off afterward, and finally only reached 63% of the WT; arrows indicate dates for $GA_3$ treatment;

FIG. 14A shows the relative mRNA levels of OSH1 and TB1 in Wild type (WT), GA2ox6$_{ACT}$ and GA2ox5Δ335-341$_{ACT}$ mutants: seeds were germinated in MS agar medium with (+) or without (−) 5 µM $GA_3$, total RNAs were isolated from embryos that containing tiller buds at 12 DAI and analyzed by RT-PCR using primers that specifically amplified rice OSH1 and TB1 cDNAs, the highest mRNA level was assigned a value of 100, and mRNA levels of other samples were calculated relative to this value, error bars indicate the SE for three replicate experiments;

FIG. 14B shows photographs of the seedlings analyzed in FIG. 14A prior to RNA isolation: panels (1) and (2) are higher magnifications of boxed areas for GA2ox5Δ335-341$_{ACT}$ and GA2ox6$_{ACT}$ mutants without $GA_3$ treatment to reveal the main stem (MS) and first tiller (1T);

FIG. 15A shows GA2ox6$_{ACT}$ mutant and wild type seedlings grown on MS agar medium with or without $GA_3$ (5 µM) for 15 days, the lower left panel is a higher magnification of the boxed area for the GA2ox6$_{ACT}$ mutant treated with GA3 to reveal the main stem and first tiller; MS means main stem; 1T means first tiller; and 1L means first true leave; and FIG. 15B shows 1-month-old wild type and GA2ox6$_{ACT}$ mutant plants sprayed with 10 µM $GA_3$ or water only every 7 days for a total of 3 sprays: + and −, presence and absence of 10 µM $GA_3$, respectively.

FIG. 16A shows a photograph of the intact seedlings taken at 12 DAI: stems of mutant and transgenic rice were thicker than that of the wild type (TNG67);

FIG. 16 B shows a photograph of the root system of the seedlings taken at 12 DAI: the mutants and transgenic rice had higher number and stronger roots;

FIG. 16 C illustrates that GA deficient mutant and transgenic rice had higher number of leaves;

FIG. 17A shows a photograph of the well watered plant of wild type, GA2ox6$_{ACT}$ Ubi: GA2ox5, and UB:iGA2ox6;

FIG. 17B illustrates that GA deficient mutant and transgenic rice had higher drought tolerance after 20 days without watering; and FIG. 17C is the magnification of the wild type and GA2ox6$_{ACT}$ plants, illustrating that the GA deficient mutant kept growing and its leaves remained green under the drought condition while the wild type wilted.

DETAILED DESCRIPTION OF THE INVENTION

Figure 1:
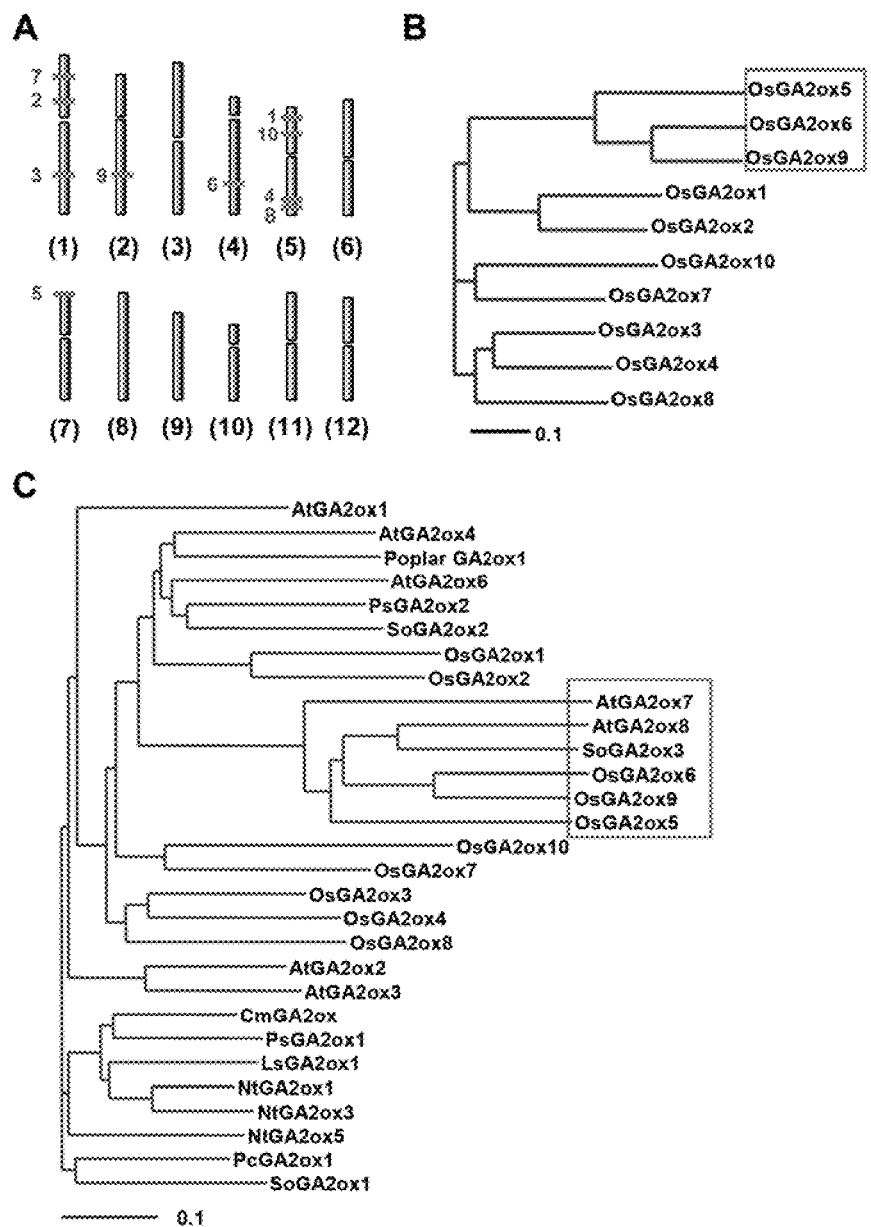
FIGS. 1A-1C illustrate the rice GA2ox family.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, the term "gene" refers to a segment of DNA involved in producing a functional RNA. A gene includes the coding region, non-coding regions preceding ("5'UTR") and following ("3'UTR") the coding region, alone or in combination. The functional RNA can be an mRNA that is translated into a peptide, polypeptide, or protein. The functional RNA can also be a non-coding RNA that is not translated into a protein species, but has a physiological function otherwise. Examples of the non-coding RNA include, but are not limited to, a transfer RNA (tRNA), a ribosomal RNA (rRNA), a micro RNA, a ribozyme, etc. A "gene" can include intervening non-coding sequences ("introns") between individual coding segments ("exons"). A "coding region" or "coding sequence" refers to the portion of a gene that is transcribed into an mRNA, which is translated into a polypeptide and the start and stop signals for the translation of the corresponding polypeptide via triplet-base codons. A "coding region" or "coding sequence" also refers to the portion of a gene that is transcribed into a non-coding but functional RNA.

As used herein, a "promoter" refers to a portion of a gene that provides a control point for regulated gene transcription. A promoter can include a binding site for RNA polymerase. A promoter can also include one or more binding sites for one or more transcription factors. A promoter is often upstream of ("5' to") the transcription initiation site of a gene. A promoter is typically adjacent to the transcriptional start site of the gene. However, a promoter can also be located at a distance from the transcriptional start site of the gene.

As promoters are typically immediately adjacent to the gene in question, positions in the promoter are designated relative to the transcriptional start site, where transcription of RNA begins for a particular gene (i.e., positions upstream are negative numbers counting back from –1, for example –100 is a position 100 base pairs upstream). Conventional notation is used herein to describe polynucleotide sequences. The left-hand end of a single-stranded polynucleotide sequence is the 5'-end, and the left-hand direction of a single-stranded polynucleotide sequence is referred to as the 5'-direction. The left-hand end of a double-stranded polynucleotide sequence is the 5'-end of the plus strand, which is depicted as the top strand of the double strands, and the right-hand end of the double-stranded polynucleotide sequence is the 5'-end of the minus strand, which is depicted as the bottom strand of the double strands. The direction of 5' to 3' addition of nucleotides to nascent RNA transcripts is referred to as the transcription direction. A DNA strand having the same sequence as an mRNA is referred to as the "coding strand." Sequence on a DNA strand which is located 5' to a reference point on the DNA is referred to as "upstream sequence"; sequence on a DNA strand which is 3' to a reference point on the DNA is referred to as "downstream sequence."

As used herein, "operably linked" refers to a functional relationship between two nucleotide sequences. A single-stranded or double-stranded nucleic acid moiety comprises the two nucleotide sequences arranged within the nucleic acid moiety in such a manner that at least one of the two nucleotide sequences is able to exert a physiological effect by which it is characterized upon the other. By way of example, a promoter sequence that controls transcription of a coding sequence is operably linked to that coding sequence. Operably linked nucleic acid sequences can be contiguous, typical of many promoter sequences, or non-contiguous, in the case of, for example, nucleic acid sequences that encode repressor proteins. Within a recombinant expression vector, "operably linked" is intended to mean that the coding sequence of interest is linked to the regulatory sequence(s) in a manner that allows for expression of the coding sequence, e.g., in an in vitro transcription/translation system or in a host cell when the vector is introduced into the host cell.

"Sequence" means the linear order in which monomers occur in a polymer, for example, the order of amino acids in a polypeptide or the order of nucleotides in a polynucleotide.

As used herein, the term "nucleotide sequence", "nucleic acid" or "polynucleotide" refers to the arrangement of either deoxyribonucleotide or ribonucleotide residues in a polymer in either single- or double-stranded form. Nucleic acid sequences can be composed of natural nucleotides of the following bases: T, A, C, G, and U, and/or synthetic analogs of the natural nucleotides. In the context of the present invention, adenosine is abbreviated as "A", cytidine is abbreviated as "C", guanosine is abbreviated as "G", thymidine is abbreviated as "T", and uridine is abbreviated as "U".

As used herein, an "isolated" nucleic acid molecule is one that is substantially separated from at least one of the other nucleic acid molecules present in the natural source of the nucleic acid, or is substantially free of at least one of the chemical precursors or other chemicals when the nucleic acid molecule is chemically synthesized. An "isolated" nucleic acid molecule can also be, for example, a nucleic acid molecule that is substantially free of at least one of the nucleotide sequences that naturally flank the nucleic acid molecule at its 5' and 3' ends in the genomic DNA of the organism from which the nucleic acid is derived. A nucleic acid molecule is "substantially separated from" or "substantially free of" other nucleic acid molecule(s) or other chemical(s) in preparations of the nucleic acid molecule when there is less than about 30%, 20%, 10%, or 5% or less, and preferably less than 1%, (by dry weight) of the other nucleic acid molecule(s) or the other chemical(s) (also referred to herein as a "contaminating nucleic acid molecule" or a "contaminating chemical").

Isolated nucleic acid molecules include, without limitation, separate nucleic acid molecules (e.g., cDNA or genomic DNA fragments produced by PCR or restriction endonuclease treatment) independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

A polynucleotide can have a single strand or parallel and anti-parallel strands. Thus, a polynucleotide may be a single-stranded or a double-stranded nucleic acid. Unless otherwise indicated, a polynucleotide is not defined by length and thus includes very large nucleic acids, as well as short ones, such as an oligonucleotide.

"Sequence identity or similarity", as known in the art, is the relationship between two or more polypeptide sequences or two or more polynucleotide sequences, as determined by comparing the sequences. As used herein, "identity", in the context of the relationship between two or more nucleic acid sequences or two or more polypeptide sequences, refers to the percentage of nucleotide or amino acid residues, respectively, that are the same when the sequences are optimally aligned and analyzed. For purposes of comparing a queried sequence against, for example, the amino acid sequence SEQ ID NO: 6, the queried sequence is optimally aligned with SEQ ID NO: 6 and the best local alignment over the entire length of SEQ ID NO: 6 is obtained.

Analysis can be carried out manually or using sequence comparison algorithms. For sequence comparison, typically one sequence acts as a reference sequence, to which a queried sequence is compared. When using a sequence comparison algorithm, test and reference sequences are input into a computer, sub-sequence coordinates are designated, if necessary, and sequence algorithm program parameters are designated.

Optimal alignment of sequences for comparison can be conducted, for example, by using the homology alignment algorithm of Needleman & Wunsch, J. Mol. Biol., 48:443 (1970). Software for performing Needleman & Wunsch analyses is publicly available through the Institut Pasteur (France) Biological Software website: http://bioweb.pasteur.fr./seqanal/interfaces/needle.html. The NEEDLE program uses the Needleman-Wunsch global alignment algorithm to find the optimum alignment (including gaps) of two sequences when considering their entire length. The identity is calculated along with the percentage of identical matches between the two sequences over the reported aligned region, including any gaps in the length. Similarity scores are also provided wherein the similarity is calculated as the percentage of matches between the two sequences over the reported aligned region, including any gaps in the length. Standard comparisons utilize the EBLOSUM62 matrix for protein sequences and the EDNAFULL matrix for nucleotide sequences. The gap open penalty is the score taken away when a gap is created; the default setting using the gap open penalty is 10.0. For gap extension, a penalty is added to the standard gap penalty for each base or residue in the gap; the default setting is 0.5.

Hybridization can also be used as a test to indicate that two polynucleotides are substantially identical to each other. Polynucleotides that share a high degree of identity will hybridize to each other under stringent hybridization conditions. "Stringent hybridization conditions" has the meaning known in the art, as described in Sambrook et al., *Molecular Cloning: A Laboratory Manual*, Second Edition, Cold Spring Harbor Laboratory, Cold Spring Harbor, N.Y., (1989). An exemplary stringent hybridization condition comprises hybridization in a medium comprising 4-6× sodium chloride/sodium citrate (SSC) at about 45-65° C., followed by one or more washes in 0.2×SSC and 0.1% SDS at 50-65° C., depending upon the length over which the hybridizing polynucleotides share complementarity or percent of identity.

As used herein, the terms "polypeptide" and "protein" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide" and "protein" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by the codons of genes may also be included in a polypeptide.

An "isolated protein" or "isolated polypeptide" is one that is substantially separated from at least one of the other proteins present in the natural source of the protein, or is substantially free of at least one of the chemical precursors or other chemicals when the protein is chemically synthesized. A protein is "substantially separated from" or "substantially free of" other protein(s) or other chemical(s) in preparations of the protein when there is less than about 30%, 20%, 10%, or 5% or less, and preferably less than 1% (by dry weight) of the other protein(s) or the other chemical(s) (also referred to herein as a "contaminating protein" or a "contaminating chemical").

Isolated proteins can have several different physical forms. The isolated protein can exist as a full-length nascent or unprocessed polypeptide, or as a partially processed polypeptide or as a combination of processed polypeptides. The full-length nascent polypeptide can be postranslationally modified by specific proteolytic cleavage events that result in the formation of fragments of the full-length nascent polypeptide. A fragment, or physical association of fragments can have the biological activity associated with the full-length polypeptide; however, the degree of biological activity associated with individual fragments can vary.

An isolated polypeptide or isolated protein can be a non-naturally occurring polypeptide. For example, an isolated polypeptide can be a "hybrid polypeptide." An isolated polypeptide can also be a polypeptide derived from a naturally occurring polypeptide by additions or deletions or substitutions of amino acids. An isolated polypeptide can also be a "purified polypeptide" which is used herein to mean a specified polypeptide in a substantially homogeneous preparation substantially free of other cellular components, other polypeptides, viral materials, or culture medium, or when the polypeptide is chemically synthesized, chemical precursors or by-products associated with the chemical synthesis. A "purified polypeptide" can be obtained from natural or recombinant host cells by standard purification techniques, or by chemical synthesis, as will be apparent to skilled artisans.

As used herein, "recombinant" refers to a polynucleotide, a polypeptide encoded by a polynucleotide, a cell, a viral particle or an organism that has been modified using molecular biology techniques to something other than its natural state.

As used herein, a "recombinant cell" or "recombinant host cell" is a cell that has had introduced into it a recombinant polynucleotide sequence. For example, recombinant cells can contain at least one nucleotide sequence that is not found within the native (non-recombinant) form of the cell or can express native genes that are otherwise abnormally expressed, under-expressed, or not expressed at all. Recombinant cells can also contain genes found in the native form of the cell wherein the genes are modified and re-introduced into the cell by artificial means. The term also encompasses cells that contain an endogenous nucleic acid that has been modified without removing the nucleic acid from the cell; such modifications include those obtained, for example, by gene replacement, and site-specific mutation. The term encompasses cells that contain the recombinant polynucleotide sequence either on a vector, such as an expression vector, or integrated into a cell chromosome.

Recombinant DNA sequence can be introduced into host cells using any suitable method including, for example, electroporation, calcium phosphate precipitation, microinjection, transformation, biolistics and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. It is further understood that the term "recombinant host cell" refers not only to the particular subject cell, but also to the progeny or potential progeny of such a cell. Because certain modifications can occur in succeeding generations due to either mutation or environmental influences, and in such circumstances, such progeny may not, in fact, be identical to the parent cell, but are still included within the scope of the term as used herein.

As used herein, the term "transgenic plant" or "transgenic line" refers to a plant that contains a recombinant nucleotide sequence comprising a genetically modified gene, e.g., a transgene. The transgenic plant can be grown or derived from a recombinant cell. A transgenic plant includes progeny, offspring, clone, breeding material or propagation material, such as seeds, thereof that comprises the transgene. As used herein, a "transgenic plant" is synonymous with "transgenic recombinant plant" or "genetically engineered plant."

As used herein, the term "semi-dwarf transgenic plant" means a transgenic plant having the phenotypic trait of a reduced height of the stem or size that is about 50% to 90% of a non-transgenic plant of the same genetic background while being grown under the same conditions. For example, the semi-dwarf transgenic plant can have a height of the stem that is about 50%, 55%, 60%, 65%, 70%, 75%, 80%, 85%, or 90% of a non-transgenic plant of the same genetic background while being grown under the same conditions.

As used herein, the term "dwarf transgenic plant" means a transgenic plant having the phenotypic trait of a reduced height of the stem or size that is about 20% to 50% of a non-transgenic plant of the same genetic background while being grown under the same conditions. For example, the dwarf transgenic plant can have a height of the stem that is about 20%, 25%, 30%, 35%, 40%, 45%, or 50% of a non-transgenic plant of the same genetic background while being grown under the same conditions.

As used herein, the term "severely dwarf transgenic plant" means a transgenic plant having the phenotypic trait of a reduced height of the stem or size that is less than about 20% of a non-transgenic plant of the same genetic background while being grown under the same conditions.

As used herein, the term "cereal plant" or "cereal crop" refers to a species of true grasses, i.e., Poaceae or Gramineae family in the Class Liliopsida of the flowering plants, or a species of pseudocereals, that is cultivated for its edible grains or seeds. Cereal plants are staple crops grown in greater quantities and provide more energy worldwide than any other type of crop. Cereal grains are a rich source of carbohydrate. Examples of cereal plants include, but are not limited to, plants of maize, rice, wheat, barley, sorghum, millets, oats, rye, triticale, buckwheat, fonio, quinoa, etc.

As used herein, an "expression vector" refers to a nucleic acid molecule that is used to recombinantly express a gene in a target cell. A heterologous or isolated nucleic acid encoding a gene of interest can be or is inserted into an expression vector. The expression vector with the heterologous or isolated nucleic acid can be or is introduced into a host cell. Once the expression vector is inside the cell, the gene product encoded by the heterologous or isolated nucleic acid is produced by the transcription and translation machinery of the host cell. An expression vector typically has for example, an origin of replication sequence allowing replication of the expression vector in the host cell, multiple cloning sites allowing insertion of the heterologous or isolated nucleic acid, a promoter allowing transcription of a gene of interest in the host cell, a heterologous or isolated nucleic acid encoding the gene of interest, a selectable marker gene that encodes a gene product allowing selection of the host cell containing the expression vector from those that do not. The properties, construction and use of expression vectors in the present invention will be readily apparent to those of skill in view of the present disclosure. For example, the expression vector according to embodiments of the present invention can be a plasmid that is replicable in an *agrobacterium* and contains a stress-inducible promoter operably linked to the coding sequence of a stress-resistant gene.

The terms "gibberellin 2-oxidase protein," "GA 2-oxidase," and "GA2ox", as used herein interchangeably, all refer to a 2-oxoglutarate-dependent dioxygenase (2-ODD) that catalyzes the inactivation of biologically active gibberellin (GA) and/or its precursors, thus reducing the endogenous levels of bioactive GAs.

A "GA2ox" can be a class C19 GA2ox, that catalyzes 2β-hydroxylation of the C-2 of biologically active $C_{19}$-GAs ($GA_1$ and $GA_4$) or $C_{19}$-GA precursors ($GA_{20}$ and $GA_9$) to produce biologically inactive GAs ($GA_8$, $GA_{34}$, $GA_{29}$, and $GA_{51}$, respectively). Examples of C19 GA2ox include, but are not limited to, rice GA2oxs 1-4, GA2ox7, GA2ox8 and GA2ox10.

A "GA2ox" can also be a class C20 GA2ox, that catalyzes 2β-hydroxylation of $C_{20}$-GA precursors but not $C_{19}$-GAs. The 2β-hydroxylation of $C_{20}$-GA precursors, e.g., converting $GA_{12}$ and $GA_{53}$ to $GA_{110}$ and $GA_{97}$, respectively, renders them unable to be converted to active GAs and thus decreases active GA levels. The class C20 GA2oxs contain three unique and conserved amino acid domains that are absent in the class C19 GA2oxs (Lee and Zeevaart, 2005). Examples of C20 GA2ox include, but are not limited to, *Arabidopsis* GA2ox7 and GA2ox8, spinach GA2ox3, and rice GA2ox5, GA2ox6 and GA2ox9.

As used herein, the term "bioactive gibberellin compound" and "bioactive GA compound", as used herein interchangeably, all refer to a gibberellin or a derivative thereof that regulates growth and influences various developmental processes of a plant. Depending on the type of gibberellin present as well as the species of plant, the physiological effects of a bioactive GA include, but are not limited to, one or more selected from the group consisting of stimulating stem elongation, stimulating bolting/flowering, breaking seed dormancy, stimulating germination, inducing sex expression, enzyme induction, causing parthenocarpic (seedless) fruit development, and delaying senescence in leaves and fruits. Examples of bioactive GA compound include, but are not limited to, $GA_1$, $GA_3$, $GA_4$ and $GA_7$.

As used herein, the "2-ODD conserved domain" is a conserved domain of the 2OG-Fe(II) oxygenase superfamily.

This family contains members of the 2-oxoglutarate (2OG) and Fe(II)-dependent oxygenase superfamily. This family includes the C-terminal of prolyl 4-hydroxylase alpha subunit. The holoenzyme has the activity EC:1.14.11.2 catalyzing the reaction: Procollagen L-proline+2-oxoglutarate+ $O_2$ <=>procollagen trans-4-hydroxy-L-proline+succinate+ $CO_2$. The full enzyme consists of a alpha2 beta2 complex with the alpha subunit contributing most of the parts of the active site. The family also includes lysyl hydrolases, isopenicillin synthases and AlkB. GA2oxs are members of the 2OG-Fe(II) oxygenase superfamily. The amino acid sequences of the 2-ODD conserved domains for OsGA2ox5; OsGA2ox6; OsGA2ox7; OsGA2ox8; OsGA2ox9-1 and OsGA2ox9-2; and OsGA2ox10-1 and OsGA2ox10-2, are SEQ ID NO:70; SEQ ID NO:71; SEQ ID NO:72; SEQ ID NO:73; SEQ ID NO:74; and SEQ ID NO:75, respectively.

In the present study, 10 putative rice GA2ox genes were identified, and differential expression of nine of them correlated with various developmental processes during rice growth, such as flower development, seed germination and tiller growth. Differential expression and/or biological activities of GA2oxs can give rise to some beneficial phenotypes in rice, including semi-dwarfism, increased root system and higher tiller numbers that may favor grain yield. In addition to some known effects caused by overexpression of GA2oxs, the early and increased growth of tiller and adventitious root and altered root architecture further suggest the pleiotropic role of GA2oxs in controlling rice growth and architecture.

GA2ox5, GA2ox6 and GA2ox9 were three genes encoding class C20 GA2oxs in rice, and their functions were further investigated using T-DNA activation tagged rice mutants and transgenic ectopic overexpression approaches. Mutants or transgenic rice recombinantly expressing class C20 GA2oxs, under the control of their native promoters or a constitutive promoter, exhibited a broad range of mutant phenotypes. Mutations in the conserved domain III were found to affect the physiological activity of class C20 GA2oxs, suggesting domain III is important for the proper biological activity of class C20 GA2oxs. Overexpression of GA2ox5 with partially functional domain III significantly alleviated the mutant phenotype.

Embodiments of the present invention demonstrate that improvement of plant architecture can be achieved by overexpression of certain wild-type or mutant GA2oxs under the control of various promoters, such as the native, constitutive, or inducible promoters.

Accordingly, one general aspect of the present invention relates to an isolated nucleic acid, comprising a nucleotide sequence that encodes a polypeptide selected from the group consisting of:

(a) a polypeptide having an amino acid sequence that is at least about 80% identical to SEQ ID NO:6, wherein the amino acid sequence has a domain that is at least 80% identical to SEQ ID NO:72;

(b) a polypeptide having an amino acid sequence that is at least about 80% identical to SEQ ID NO:8, wherein the amino acid sequence has a domain that is at least 80% identical to SEQ ID NO:73;

(c) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74; and (d) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75.

The invention encompasses any isolated nucleic acid encoding an amino acid sequence that is at least about 80% identical to SEQ ID NO:6, SEQ ID NO:8, SEQ ID NO:10, SEQ ID NO:12, SEQ ID NO:14 or SEQ ID NO:16, and the amino acid sequence has a domain that is at least 80% identical to the 2-ODD conserved domain within each of the respective sequences. In embodiments of the present invention, the nucleic acid encodes an amino acid sequence that is 80%, 85%, 90%, 95%, or 100% identical to SEQ ID NO:6; SEQ ID NO:8; SEQ ID NO:10 or SEQ ID NO:12; or SEQ ID NO:14 or SEQ ID NO:16, and the amino acid sequence has a domain that is at least 80%, 85%, 90%, 95%, or 100% identical to SEQ ID NO:72; SEQ ID NO:73; SEQ ID NO:74; or SEQ ID NO:75, respectively. In particular embodiments of the present invention, the nucleic acid can be genomic DNAs, cDNAs, and chemically synthesized DNAs.

Due to the degeneracy of the genetic code, more than one codon may be used to encode a particular amino acid, and therefore, an amino acid sequence (for example, SEQ ID NO: 6) can be encoded by any one of a plurality of nucleic acid sequences. Isolated nucleic acid includes sequences wherein one or more codons in the sequence are replaced by codons of a different sequence but that code for the same amino acid residue are herein referred to as "conservative codon substitutions".

In one embodiment, the invention encompasses nucleic acid sequences that have one or more than one conservative codon substitutions. One of skill in the art would be able to determine a particular nucleic acid sequence having one or more than one conservative codon substitutions and encoding the above amino acid sequence, based on the sequence information provided herein.

Conservative codon substitutions can be made in the nucleic acid sequence encoding the polypeptide, for example, the codons TTT and TTC (collectively referred to as TTT/C) can encode a Phe (phenylalanine) residue; other exemplary codon substitutions include, but are not limited to: TTA/G and CTT/C/A/G: Leu; ATT/C: Ile; ATG: Met; GTT/C/A/G: Val; TCT/C/A/G: Ser; CCT/C/A/G: Pro; ACT/C/A/G: Thr; GCT/C/A/G: Ala; TAT/C: Tyr; CAT/C: His; CAA/G: Gln; AAT/C: Asn; AAA/G: Lys; GAT/C: Asp; GAA/G Glu; TGT/C: Cys; CGT/C/A/G: Arg; AGT/C: Ser; AGA/G; Arg; GGT/C/A/G: Gly. Conservative codon substitutions can be made at any position in the nucleic acid sequence that encodes the recited amino acid sequence.

In an embodiment of the present invention, the isolated nucleic acid comprises a nucleotide sequence that encodes a polypeptide selected from the group consisting of SEQ ID NO:6, SEQ ID NO:8, SEQ ID NO:10, SEQ ID NO:12, SEQ ID NO:14 and SEQ ID NO:16.

In another embodiment of the present invention, the isolated nucleic acid comprises a nucleotide sequence selected from the group consisting of SEQ ID NO:5, SEQ ID NO:7, SEQ ID NO:9, SEQ ID NO:11, SEQ ID NO:13 and SEQ ID NO:15.

A nucleic acid according to embodiments of the present invention can be readily designed, synthesized and isolated using methods known in the art, in view of the present disclosure. For example, a genomic DNA or cDNA can be prepared according to conventional methods known to those skilled in the art in view of the present disclosure. In one embodiment, genomic DNA can be prepared as follows: (1) extract a genomic DNA from rice cultivars having a DNA encoding a protein with a GA2-oxidation activity; (2) construct a genomic library (utilizing a vector such as a plasmid, phage, cosmid, BAC, or PAC); (3) spread the library; and (4) conduct colony hybridization or plaque hybridization using a probe prepared based on a DNA encoding a polypeptide that is at least about 80% identical to an amino acid sequence selected from the group consisting of SEQ ID NO:6, SEQ ID NO:8, SEQ ID NO:10, SEQ ID NO:12, SEQ ID NO:14 and SEQ ID NO:16. In another embodiment, a genomic DNA can be prepared via PCR using primers specific for a DNA encoding a polypeptide that is at least about 80% identical to an amino acid sequence selected from the group consisting of SEQ ID NO:6, SEQ ID NO:8, SEQ ID NO:10, SEQ ID NO:12, SEQ ID NO:14 and SEQ ID NO:16. cDNA can be prepared as follows: (1) synthesize cDNAs based on mRNAs extracted from rice cultivars having a DNA encoding a protein with a GA2-oxidation activity; (2) prepare a cDNA library by inserting the synthesized cDNA into a vector such as λZAP; (3) spread the cDNA library; and (4) conduct colony hybridization or plaque hybridization as described above. Alternatively, cDNA can also be prepared by RT-PCR. The DNA can be isolated by gel electrophoresis.

A nucleic acid according to embodiment of the present invention can be used to express a polypeptide of the present invention. The nucleic acid can also be used to produce an expression vector, a recombinant cell or a transgenic plant. Preferably, the polypeptide, expression vector, recombinant cell and transgenic plant can be used to regulate plant development, e.g., to suppress plant growth resulting in a semi-dwarf transgenic plant.

In another general aspect, the present invention relates to an isolated polypeptide comprising an amino acid sequence selected from the group consisting of:
  (a) an amino acid sequence that is at least about 80% identical to SEQ ID NO:6, wherein the amino acid sequence has a domain that is at least 80% identical to SEQ ID NO:72;
  (b) an amino acid sequence that is at least about 80% identical to SEQ ID NO:8, wherein the amino acid sequence has a domain that is at least 80% identical to SEQ ID NO:73;
  (c) an amino acid sequence that is at least about 80% identical to SEQ ID NO:10 or at least about 80% identical to SEQ ID NO:12, wherein the amino acid sequence has a domain that is at least 80% identical to SEQ ID NO:74; and
  (d) an amino acid sequence that is at least about 80% identical to SEQ ID NO:14 or at least about 80% identical to SEQ ID NO:16, wherein the amino acid sequence has a domain that is at least 80% identical to SEQ ID NO:75.

The invention encompasses any isolated polypeptide comprising an amino acid sequence that is at least about 80% identical to SEQ ID NO:6, SEQ ID NO:8, SEQ ID NO:10, SEQ ID NO:12, SEQ ID NO:14 or SEQ ID NO:16, and the amino acid sequence has a domain that is at least 80% identical to the 2-ODD conserved domain within each of the respective sequences. In embodiments of the present invention, the polypeptide comprises an amino acid sequence that is 80%, 85%, 90%, 95%, or 100% identical to SEQ ID NO:6; SEQ ID NO:8; SEQ ID NO:10 or SEQ ID NO:12; or SEQ ID NO:14 or SEQ ID NO:16, and the amino acid sequence has a domain that is at least 80%, 85%, 90%, 95%, or 100% identical to SEQ ID NO:72; SEQ ID NO:73; SEQ ID NO:74; or SEQ ID NO:75, respectively. Preferably, the polypeptide has GA2ox biological activity.

The polypeptide according to embodiment of the present invention can have additional amino acid residues. In some embodiments, the additional amino acids are present at the amino terminus, the carboxyl terminus, within the polypeptide sequence or combinations of these locations. Polypeptides having these types of additional amino acid sequences can be referred to as "fusion proteins". In some cases, it may be more appropriate to refer to them otherwise as "chimeric" or "tagged" proteins, or the like, depending on the nature of the additional amino acid sequences. Nonetheless, one will be able to discern a polypeptide having additional amino acid sequences given the sequence information provided herein. The additional amino acid residues can be short, for example, from one to about 20 additional amino acid residues, or longer, for example, greater than about 20 additional amino acid residues. The additional amino acid residues can serve one or more functions or purposes including, for example, serving as epitopes for protein (e.g., antibody) or small molecule binding; serving as tags for intracellular and extracellular trafficking; providing additional enzymatic or other activity; or providing a detectable signal.

For example, the fusion protein can include additional amino acid residues providing coordinates for bonding (such as ionic, covalent, coordinative, hydrogen or Van der Waals bonding or combinations thereof) with organic or inorganic compounds. Useful additional amino acid sequences include, for example, poly-histidine residues useful for protein purification via $Ni^+$-coupled residue, constant domains of immunoglobulins (IgA, IgE, IgG, IgM) or portions thereof (CH1, CH2, CH3), albumin, hemagluttinin (HA) or myc affinity epitope tags useful for the formation of immuno-complexes for detection or purification (antibodies against these moieties can be obtained commercially), polypeptides useful for detection such as the green fluorescent protein (GFP), enzymes such as beta-galactosidase (B-Gal), chloramphenicol acetyltransferase (CAT), luciferase, and alkaline phosphatase (A), signal sequences for protein trafficking and protease cleavage sequences useful for separating additional amino acid sequences from the sequence, if desired.

In an embodiment of the present invention, the isolated polypeptide comprises an amino acid sequence selected from the group consisting of SEQ ID NO:6, SEQ ID NO:8, SEQ ID NO:10, SEQ ID NO:12, SEQ ID NO:14 and SEQ ID NO:16.

A polypeptide according to embodiments of the present invention can be readily designed, synthesized and isolated using methods known in the art, in view of the present disclosure. The polypeptide can be produced as recombinant or naturally-occurring proteins by a method known to one skilled in the art. For example, a recombinant protein can be produced by a method comprising: (1) synthesizing a DNA encoding the protein using PCR with primers having desired restriction enzyme sites; (2) cloning the DNA into an expression vector, such as the pMAL-c2 expression vector (NEB); (3) transforming the expression vector into a host cell, such as *Escherichia coli* strain BL21 cell, to create a recombinant cell; (4) growing the recombinant cell under conditions to allow its expression of the recombinant protein; and (5) isolating the recombinant protein from the recombinant cell. The isolation of the recombinant protein can be facilitated by expressing the recombinant protein as a fusion protein with a histidine tag, maltose-binding protein, or glutathione-S-transferase (GST), and subsequently purifying or isolating the protein on a nickel column, an amylose-column, or a GST-glutathione column, respectively. After the purification or isolation, the above-described tag can be cleaved off using proteases, such as, thrombin and factor Xa as required.

When the polypeptide is produced and isolated as a naturally-occurring protein, such a protein is naturally produced by a plant or a plant tissue, and is isolated, for example, by binding an antibody to the polypeptide to an affinity column and contacting with the column an extract from the plant or plant tissue, such as rice or rice leaves, naturally expressing the polypeptide. The antibody can be prepared by immunizing a suitable animal with a partial sequence of the polypeptide made synthetically.

Another general aspect of the present invention relates to an isolated nucleic acid comprising a nucleotide sequence that encodes a mutant class C20 gibberellin 2-oxidase protein (GA2ox), or an isolated polypeptide comprising the mutant class C20 GA2ox.

The mutant C20 GA2ox has at least one mutation in domain III of a class C20 GA2ox and has a reduced enzymatic activity to hydroxylate a class $C_{20}$-GA precursor compared with an otherwise identical class C20 GA2ox that lacks the at least one mutation. The domain III, which comprises an amino acid sequence of SEQ ID NO:17, is one of the three unique and conserved amino acid domains that are present in the class C20 GA2oxs, but absent in the class C19 GA2oxs. It was discovered in the present invention that mutations in domain III affect the physiological activity of class C20 GA2oxs.

In an embodiment of the present invention, domain III comprises an amino acid sequence selected from the group consisting of: SEQ ID NO:18, SEQ ID NO:19, SEQ ID NO:20, SEQ ID NO:21, SEQ ID NO:22, and SEQ ID NO:23, and the otherwise identical class C20 GA2ox comprises an amino acid sequence selected from the group consisting of SEQ ID NO:2, SEQ ID NO:4, SEQ ID NO:10, SEQ ID NO:24, SEQ ID NO:25 and SEQ ID NO:26.

In view of the present disclosure, methods known in the art, such as site-directed mutagenesis (Kramer and Fritz, *Methods in Enzymology*, 154: 350-367 (1987)), can be used to introduce the at least one mutation, such as a deletion, insertion or substation of one or more amino acids, in domain III. The number and identity of amino acids that are mutated in domain III are not particularly restricted, as long as the class C20 GA2ox with the mutated domain III has a reduced enzymatic activity to hydroxylate a class $C_{20}$-GA precursor compared with an otherwise identical class C20 GA2ox that lacks the at least one mutation.

The enzymatic activity of a class C20 GA2ox with or without one or more mutations in domain III can be assayed using various methods known in the art in view of the present disclosure. For example, the class C20 GA2ox can be isolated or purified, e.g., from a recombinant cell that expresses the C20 GA2ox, or from a plant that has the C20 GA2ox. The enzymatic activity of the isolated or purified C20 GA2ox to hydroxylate a class $C_{20}$-GA precursor can be measured in vitro using a radio-labeled $C_{20}$-GA precursor, such as radio-labeled $GA_{12}$ or $GA_{53}$ (see Lee and Zeevaart, 2002; Schomburg et al., 2003). The enzymatic activity of the isolated or purified C20 GA2ox to hydroxylate a class $C_{20}$-GA precursor can also be measured in vivo by analyzing the amount of $GA_1$ or $GA_{97}$ in plant extracts, e.g., from the mature leaves or seedlings of plants containing the C20 GA2ox.

In an embodiment of the present invention, the mutant class C20 GA2ox comprises an amino acid sequence selected from the group consisting of:
 (a) the amino acid sequence of SEQ ID NO:27, which has a deletion of amino acid residues 335-341 of SEQ ID NO:2 (GA2ox5), i.e., GA2ox5 Δ335-341;
 (b) the amino acid sequence of SEQ ID NO:28, which has a deletion of amino acid residues 325-341 of SEQ ID NO:2 (GA2ox5), i.e., GA2ox5Δ325-341;
 (c) the amino acid sequence of SEQ ID NO:29, which has a deletion of amino acid residues 338-358 of SEQ ID NO:4 (GA2ox6), i.e., GA2ox6Δ338-358;
 (d) the amino acid sequence of SEQ ID NO:30, which has a deletion of amino acid residues 348-358 of SEQ ID NO:4 (GA2ox6), i.e., GA2ox6Δ348-358;
 (e) the amino acid sequence of SEQ ID NO:68, which has a deletion of amino acid residues 344-358 of SEQ ID NO:10 (GA2ox9-1), i.e., GA2ox9-1Δ344-359; and
 (f) the amino acid sequence of SEQ ID NO:69, which has a deletion of amino acid residues 354-358 of SEQ ID NO:10 (GA2ox9-1), i.e., GA2ox9-1Δ354-359.

Another general aspect of the present invention relates to an expression vector comprising a nucleotide sequence that encodes a polypeptide selected from the group consisting of:
 (a) a polypeptide having an amino acid sequence that is at least about 80% identical to SEQ ID NO:2, wherein the amino acid sequence has a domain that is at least 80% identical to SEQ ID NO:70;
 (b) a polypeptide having an amino acid sequence that is at least about 80% identical to SEQ ID NO:4, wherein the amino acid sequence has a domain that is at least 80% identical to SEQ ID NO:71;
 (c) a polypeptide having an amino acid sequence that is at least about 80% identical to SEQ ID NO:6, wherein the amino acid sequence has a domain that is at least 80% identical to SEQ ID NO:72;
 (d) a polypeptide having an amino acid sequence that is at least about 80% identical to SEQ ID NO:8, wherein the amino acid sequence has a domain that is at least 80% identical to SEQ ID NO:73;
 (e) a polypeptide having an amino acid sequence that is at least about 80% identical to SEQ ID NO:10 or SEQ ID NO:12, wherein the amino acid sequence has a domain that is at least 80% identical to SEQ ID NO:74;
 (f) a polypeptide having an amino acid sequence that is at least about 80% identical to SEQ ID NO:14 or 16, wherein the amino acid sequence has a domain that is at least 80% identical to SEQ ID NO:75;
 (g) a mutant class C20 GA2ox, the mutant GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, and the domain III comprising the amino acid sequence of SEQ ID NO:17.

The expression vectors comprise a nucleic acid according to embodiments of the invention in a form suitable for expression of the nucleic acid in a host cell. It will be appreciated by those skilled in the art that the design of the expression vector can depend on such factors as the choice of the host cell to be transformed, the level of expression of protein desired, etc. The expression vectors according to embodiments of the invention can be introduced into host cells to thereby produce proteins or peptides, including fusion proteins or peptides, encoded by nucleic acids as described herein.

In an embodiment of the present invention, the expression vector is replicable and confers a selective marker in a plant cell. In another embodiment of the present invention, the expression vector is replicable and confers a selective marker in an *Agrobacterium*, a bacterium known for its ability to transfer nucleic acid between itself and plants. In yet another embodiment of the present invention, the expression vector allows the shuttling or exchange of nucleotide sequences between a plant cell and an *Agrobacterium*. Such expression vectors can be a modified bacterial tumor-inducing (Ti) plasmid or a bacterial root-inducing (Ri) plasmid.

In an embodiment of the present invention, the expression vector comprises a nucleotide sequence that encodes a polypeptide selected from the group consisting of: SEQ ID NO:2, SEQ ID NO:4, SEQ ID NO:6, SEQ ID NO:8, SEQ ID NO:10, SEQ ID NO:12, SEQ ID NO:14 and SEQ ID NO:16.

In another embodiment of the present invention, the expression vector comprises a nucleotide sequence that encodes a mutant class C20 GA2ox comprising an amino acid sequence selected from the group consisting of: SEQ ID NOs:27-30, SEQ ID NO:68 and SEQ ID NO:69.

Any of a variety of procedures known in the art, such as electroporation, calcium phosphate precipitation, polyethylene glycol transformation, microinjection, nanoparticle-mediated transformation, particle bombardment, *Agrobacterium*-mediated transfer, biolistics-mediated transformation and viral infection, can be used to introduce an expression vector into a host cell in view of the present disclosure.

In another general aspect, the present invention relates to a recombinant cell comprising a nucleotide sequence according to embodiments of the invention. In one embodiment, the recombinant cell is a recombinant plant cell, which includes various forms of plant cells, such as cultured cell suspensions, protoplasts, leaf sections and calluses. In another embodiment, the recombinant cell is a recombinant *Agrobacterium* cell. In another embodiment, the recombinant cell comprises an expression vector according to embodiments of the present invention. In an embodiment of the present invention, the recombinant cell comprises a nucleotide sequence that encodes a polypeptide selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NOs:27-30, SEQ ID NO:68 and SEQ ID NO:69.

Any of a variety of procedures known in the art can be used to construct a recombinant cell according to embodiments of the present invention. For example, a nucleotide sequence according to embodiments of the invention can be introduced into a host cell via a vector. The nucleotide sequence can stay on the vector, separate from the chromosome, in the recombinant cell, such as in a transiently transfected recombinant cell that transiently expresses a gene product encoded by the nucleotide sequence. The nucleotide sequence can also be integrated into the chromosome in the recombinant cell, such as in a stably transfected recombinant cell that stably expresses a gene product encoded by the nucleotide sequence.

In another general aspect, the present invention relates to a transgenic plant comprising a transgene, wherein the transgene encodes a polypeptide selected from the group consisting of:

(a) a polypeptide having an amino acid sequence that is at least about 80% identical to SEQ ID NO:2, wherein the amino acid sequence has a domain that is at least 80% identical to SEQ ID NO:70;

(b) a polypeptide having an amino acid sequence that is at least about 80% identical to SEQ ID NO:4, wherein the amino acid sequence has a domain that is at least 80% identical to SEQ ID NO:71;

(c) a polypeptide having an amino acid sequence that is at least about 80% identical to SEQ ID NO:6, wherein the amino acid sequence has a domain that is at least 80% identical to SEQ ID NO:72;

(d) a polypeptide having an amino acid sequence that is at least about 80% identical to SEQ ID NO:8, wherein the amino acid sequence has a domain that is at least 80% identical to SEQ ID NO:73

(e) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74;

(f) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75;

(g) a mutant class C20 GA2ox, the mutant GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, and the domain III comprising the amino acid sequence of SEQ ID NO:17.

In an embodiment of the present invention, the transgenic plant comprises the mutant class C20 GA2ox, wherein (a) the domain III comprises an amino acid sequence selected from the group consisting of SEQ ID NOs:18-23; and (b) the otherwise identical class C20 GA2ox comprises an amino acid sequence selected from the group consisting of: SEQ ID NO:2, SEQ ID NO:4, SEQ ID NO:10, SEQ ID NO:24, SEQ ID NO:25, and SEQ ID NO:26.

In a preferred embodiment of the present invention, the transgenic plant comprises a transgene, which encodes a polypeptide having the amino acid sequence selected from the group consisting of: SEQ ID NO:2, SEQ ID NO:4, SEQ ID NO:10, SEQ ID NOs:27-30, SEQ ID NO:68 and SEQ ID NO:69.

In one embodiment, a transgenic plant according to embodiments of the present invention stably expresses a gene encoded by a recombinant nucleic acid molecule according to embodiments of the invention. In such a transgenic plant, the recombinant nucleic acid molecule is stably transformed or transfected into a plant cell and has become integrated into the chromosome of the plant cell so that the recombinant nucleic acid molecule is inherited by daughter cells of the plant cell through chromosome replication.

Any of a variety of procedures known in the art can be used to engineer a stable transgenic plant in view of the present disclosure. In one embodiment of the present invention, the transgenic plant is constructed by transforming a tissue of a plant, such as a protoplast or leaf-disc of the plant, with a recombinant *Agrobacterium* cell comprising a nucleic acid molecule according to embodiments of the present invention, and generating a whole plant using the transformed plant tissue. In another embodiment of the present invention, flowers of a plant can be dipped in a culture of recombinant *Agrobacterium* cell comprising a nucleic acid molecule according to embodiments of the present invention. After the bacterium transforms the germline cells that make the female gametes, seeds can be screened for markers carried by the nucleic acid molecule according to embodiments of the present invention. Transgenic plants are then grown out of the seeds.

In another embodiment of the present invention, a nucleic acid molecule according to embodiments of the invention can be introduced into a plant via gene gun technology, particularly when transformation with a recombinant *Agrobacterium* cell is less efficient in the plant. The gene gun technology, also referred to as biolistics, delivers genetic information via an elemental particle of a heavy metal coated with plasmid DNA. This technology is able to transform almost any type of plant cells.

In another embodiment, a transgenic plant according to embodiments of the present invention transiently expresses a gene encoded by a recombinant nucleic acid molecule according to embodiments of the invention. Any of a variety of procedures known in the art can be used to engineer such a transgenic plant in view of the present disclosure. In one embodiment, a recombinant nucleic acid molecule according to embodiments of the invention can be introduced into a transgenic plant by particle bombardment, a specific example of which is described below in the examples. In another embodiment, the method of agroinfiltration can be used to allow transient expression of genes in a plant. In the method, for example, a recombinant nucleic acid molecule according to embodiments of the invention is first introduced into a strain of *Agrobacterium* to generate a recombinant *Agrobacterium* cell. A liquid suspension of the recombinant *Agrobacterium* is then injected into the airspaces inside a plant leaf. Once inside the leaf, the recombinant *Agrobacterium* transforms the gene of interest to a portion of the plant cells and the gene is then transiently expressed. As compared to traditional plant transformation, the method of agroinfiltration is speedy and convenient.

The transgenic plant according to embodiments of the present invention can be both monocot and dicot transgenic plants. In an embodiment of the present invention, the transgenic plant is a transgenic cereal plant, preferably a transgenic rice plant.

The transgenic plant according to embodiments of the present invention can comprise a transgene that is operably linked to any suitable promoters known in the art to provide a control point for regulated gene transcription of the transgene in the transgenic plant. The promoters that can be used in the present invention, include, but are not limited to a native promoter; a constitutive promoter selected from the group consisting of a maize ubiquitin (Ubi) promoter, a rice actin (Act1) promoter, and cauliflower mosaic 35S RNA promoter (CaMV35S) promoter; a tissue-specific promoter selected from the group consisting of a rice glutelin (GluB) promoter, a rubisco small subunit (rbcs) promoter and a maize zean gene promoter; a developmental stage-specific promoter selected from the group consisting of a rice alpha-amylase (αAmy) promoter and a rice glycine rich RNA binding protein (GRRP-A1) promoter; and an inducible promoter inducible by drought, salt, high or low temperatures, hypoxia, anoxia, hydration, pH, chemicals, or hormones. Examples of the inducible promoters that can be used in the present invention, include, but are not limited to, promoters for the genes of *Arabidopsis* rd29A, cor15A, kin1, heat-shock factor (HSF), C-repeat-binding factor (CBF1) and dehydration-responsive element binding protein (DREB1A); and promoters for the genes of rice HVA1 (ABA-inducible), alcohol dehydrogenase (Adh), ethanol-inducible, and alpha-amylase (GA-inducible).

In an embodiment of the present invention, the promoter is expressed in developing seeds, during seed germination, in early seedlings, or in growing plants.

In another embodiment of the present invention, the transgenic plant is at least about 10% shorter, or has more root system, earlier tillering, higher tillering numbers, higher biomass, or higher seed production, than a non-transgenic plant of the same genetic background while being grown under the same conditions. Tillering is an important agronomic trait for grain yield. The tiller is a specialized grain-bearing branch that normally arises from the axil of each leaf and grows independently of the mother stem (culm) with its own adventitious roots. The present invention demonstrates that plant architecture improvements, including, but not limited to semidwarfism, increased root system and higher tiller numbers, which favor grain yield, could be induced by increased expression or activity of wild-type or modified C19 GA2oxs or C20 GA2oxs.

In a preferred embodiment, the transgenic plant is a semi-dwarf or dwarf transgenic plant having a height that is about 20% to 90% of a non-transgenic plant of the same genetic background while being grown under the same conditions. In particular embodiments, the transgenic plant is a semi-dwarf or dwarf transgenic plant having a height that is about 20%, 25%, 30%, 35%, 40%, 45%, 50%, 55%, 60%, 65%, 70%, 75%, 80%, 85%, or 90% of that of a non-transgenic plant of the same genetic background while being grown under the same conditions.

An embodiment of the present invention also includes a propagation material obtained from the transgenic plant according to embodiments of the present invention, wherein the propagation material contains the transgene.

In another general aspect, the present invention relates to a method of producing a transgenic plant of the present invention. The method comprises: (a) transforming a plant cell with a nucleic acid molecule comprising the transgene according to an embodiment of the present invention to obtain a recombinant plant cell; and (b) growing the recombinant plant cell obtained in (a) to generate a transgenic plant.

Another general aspect of the present invention relates to a method of inhibiting stem elongation and promoting tiller growth in a plant. The method comprises: (a) transforming a plant cell with a nucleic acid molecule comprising a transgene according to an embodiment of the present invention to obtain a recombinant plant cell that expresses a polypeptide encoded by the transgene; and (b) growing the recombinant plant cell obtained in (a) to generate a transgenic plant; wherein the polypeptide is expressed in the transgenic plant at a level sufficient to inhibit stem elongation and promote tiller growth in the transgenic plant.

In another embodiment of the method of the present invention, the transgene encodes a mutant class C20 GA2ox having at least one mutation in domain III of the class C20 GA2ox. The mutant GA2ox has a reduced enzymatic activity to hydroxylate a class $C_{20}$-GA precursor compared with an otherwise identical class C20 GA2ox that lacks the at least one mutation. Preferably, the domain III comprises an amino acid sequence selected from the group consisting of SEQ ID NO:18, SEQ ID NO:19, SEQ ID NO:20, SEQ ID NO:21, SEQ ID NO:22 and SEQ ID NO:23, and the otherwise identical class C20 GA2ox that lacks the at least one mutation comprising an amino acid sequence selected from the group consisting of: SEQ ID NO:2, SEQ ID NO:4, SEQ ID NO:10, SEQ ID NO:24, SEQ ID NO:25 and SEQ ID NO:26.

According to an embodiment of the present invention, the transgene used in the method encodes a polypeptide selected from the group consisting of a polypeptide having the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:27, SEQ ID NO:30 and SEQ ID NO:69.

According to an embodiment of the present invention, the transgene can be overexpressed in the transgenic plant, i.e., is expressed at a level higher than that of an otherwise identical gene in a non-transgenic plant of the same genetic background. For example, the transgene encoding SEQ ID NO:2, SEQ ID NO:4, SEQ ID NO:10, SEQ ID NO:28, or SEQ ID NO:29 was overexpressed in transgenic rice plants according to embodiments of the invention.

According to another embodiment of the present invention, the transgene can be expressed at a level the same as or lower than that of an otherwise identical gene in a non-transgenic plant of the same genetic background. For example, the transgene encoding SEQ ID NO:6, SEQ ID NO:8, SEQ ID NO:12, SEQ ID NO:14, SEQ ID NO:16, SEQ ID NO:27, SEQ ID NO:30 or SEQ ID NO:69 was not overexpressed in transgenic rice plants according to embodiments of the invention.

According to a preferred embodiment of the present invention, the method further comprises breeding the transgenic plant with another plant to obtain a semi-dwarf or dwarf transgenic plant that still contains the transgene. Preferably, the transgenic plant is a severely dwarf transgenic plant and the other plant is a non-transgenic plant of the same genetic background. The breeding of the severely dwarf transgenic plant with the non-transgenic plant can produce a semi-dwarf or dwarf transgenic plant that is less dwarf than the severely dwarf parent transgenic plant. More preferably, the transgene in the transgenic plant encodes a polypeptide selected from the group consisting of SEQ ID NO:2, SEQ ID NO:4, SEQ ID NO:6, SEQ ID NO:8 and SEQ ID NO:10.

According to another preferred embodiment of the present invention, the transgene used in the method encodes a polypeptide selected from the group consisting of a polypeptide having the amino acid sequence of SEQ ID NO:10, SEQ ID NO:27, SEQ ID NO:30 and SEQ ID NO:69, and the polypeptide is expressed in the transgenic plant at a level sufficient to inhibit growth and make a semi-dwarf transgenic plant.

Another general aspect of the present invention relates to a method of obtaining a semi-dwarf transgenic plant. The method comprises: (a) providing a transgenic plant according to embodiments of the present invention or a propagation material thereof; (b) growing the transgenic plant or the propagation material thereof, so that the polypeptide transgenically or recombinantly expressed in the transgenic plant is at a level sufficient to inhibit growth of the transgenic plant; and (c) applying to the transgenic plant or the propagation material thereof a composition comprising at least one bioactive GA compound, so that the transgenic plant or propagation material thereof produces a semi-dwarf transgenic plant. The bioactive GA compound can be applied directly to the transgenic plant or the propagation material or indirectly to the soil in which the transgenic plant or the propagation material is grown.

The transgene expressed in the transgenic plant can be any of the transgene according to embodiments of the present invention. In an embodiment of the present invention, the transgene encodes a polypeptide having the amino acid sequence of SEQ ID NO:2, SEQ ID NO:4, SEQ ID NO:6, SEQ ID NO:8 or SEQ ID NO:10. In a preferred embodiment, the transgene is overexpressed in the transgenic plant.

The bioactive GA compound can be any bioactive GA compounds. In an embodiment of the present invention, the bioactive GA compound is not inactivated by the polypeptide recombinantly produced by the transgenic plant. Preferably, the bioactive GA compound is selected from the group consisting of $GA_1$, $GA_3$, $GA_4$ and $GA_7$.

Another general aspect of the present invention relates to a method of inhibiting stem elongation and promoting tiller growth in a plant, comprising administering to the plant a compound that increases the expression of a gene encoding a polypeptide or the enzymatic activity of the polypeptide in the plant, wherein the polypeptide is selected from the group consisting of:

(a) a polypeptide having an amino acid sequence that is at least about 80% identical to SEQ ID NO:2, wherein the amino acid sequence has a domain that is at least 80% identical to SEQ ID NO:70;

(b) a polypeptide having an amino acid sequence that is at least about 80% identical to SEQ ID NO:4, wherein the amino acid sequence has a domain that is at least 80% identical to SEQ ID NO:71;

(c) a polypeptide having an amino acid sequence that is at least about 80% identical to SEQ ID NO:6, wherein the amino acid sequence has a domain that is at least 80% identical to SEQ ID NO:72;

(d) a polypeptide having an amino acid sequence that is at least about 80% identical to SEQ ID NO:8, wherein the amino acid sequence has a domain that is at least 80% identical to SEQ ID NO:73;

(e) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74; and (f) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75.

In a preferred embodiment, the polypeptide is selected from the group consisting of SEQ ID NO:2, SEQ ID NO:4, SEQ ID NO:6, SEQ ID NO:8, SEQ ID NO:10, and the plant is a rice plant.

The compound that increases the expression of a gene encoding a polypeptide or the enzymatic activity of the polypeptide in the plant can be of any type, including, but not limited to a small molecule chemical compound and a molecule of biological origin, i.e., that is originally identified as a molecule made by a biological system, such as a plant, a microorganism, etc., or derivatives thereof.

Another general aspect of the present invention relates to a method of identifying a compound that inhibits stem elongation and promotes tiller growth in a plant, comprising identifying a compound that increases the expression of a gene encoding a polypeptide or the enzymatic activity of the polypeptide in the plant, wherein the polypeptide is selected from the group consisting of:

(a) a polypeptide having an amino acid sequence that is at least about 80% identical to SEQ ID NO:2, wherein the amino acid sequence has a domain that is at least 80% identical to SEQ ID NO:70;

(b) a polypeptide having an amino acid sequence that is at least about 80% identical to SEQ ID NO:4, wherein the amino acid sequence has a domain that is at least 80% identical to SEQ ID NO:71;

(c) a polypeptide having an amino acid sequence that is at least about 80% identical to SEQ ID NO:6, wherein the amino acid sequence has a domain that is at least 80% identical to SEQ ID NO:72;

(d) a polypeptide having an amino acid sequence that is at least about 80% identical to SEQ ID NO:8, wherein the amino acid sequence has a domain that is at least 80% identical to SEQ ID NO:73;

(e) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74; and (f) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75.

In a preferred embodiment, the polypeptide is selected from the group consisting of SEQ ID NO:2, SEQ ID NO:4, SEQ ID NO:6, SEQ ID NO:8 and SEQ ID NO:10, and the plant is a rice plant.

Various methods can be used to facilitate the identification of the compounds. For example, in vitro assay, preferably high-though put assay, can be conducted using an isolated polypeptide to identify compounds that increase the enzymatic activity of the polypeptide. Such in vitro assay can be based on the enzymatic activity of a C19 GA2ox, such as GA2ox7, GA2ox8 or GA2ox10, to hydroxylate the C-2 of biologically active $C_{19}$-GAs ($GA_1$ and $GA_4$) or $C_{19}$-GA precursors ($GA_{20}$ and $GA_9$) to produce biologically inactive GAs ($GA_8$, $GA_{34}$, $GA_{29}$, and $GA_{51}$, respectively). The in vitro assay can also be based on the enzymatic activity of a C20 GA2ox, such as GA2ox5, GA2ox6 or GA2ox9, to catalyze 2β-hydroxylation of $C_{20}$-GA precursors, e.g., converting $GA_{12}$ and $GA_{53}$ to $GA_{110}$ and $GA_{97}$, respectively. The enzymatic activity of a C19 GA2ox or C20 GA2ox can be measured using methods known to those skilled in the art, for example, by using a radio-labeled $C_{19}$-GA, $C_{19}$-GA precursor or $C_{20}$-GA precursor.

Compounds that increase the expression of a gene of interest can be identified using a cell based reporter assay. The transcriptional regulatory region of a gene according to an embodiment of the present invention, including the promoter and the 5'- and/or 3'-untranslated regulatory (UTR) region of the gene, can be operably linked to the coding sequence of a reporter gene, such as a luciferase gene (lux), a β-galactosidase gene (lacZ), a green fluorescent protein gene (GFP), etc. The expression level of the gene can thus be more easily measured from a cell as the biological activity of the reporter gene product. A compound that increases the expression of the gene can be identified by its ability to increase the detected amount of the biological activity of the reporter gene product from the reporter assay.

The compound can be further identified using an in vivo assay, e.g., by administering the compound to a plant and analyzing the amount of biologically inactive GAs in plant extracts.

Another general aspect of the invention relates to a method of generating a transgenic plant having a feature selected from the group consisting of less height, higher tillering, more biomass, a stronger and thicker stem, a stronger root system, more leaves, stable increase of yields and/or seed production, and enhanced stress tolerance, as compared with a plant of substantially the same genetic background grown under the same conditions. The method comprises:
  (a) transforming a cell of the plant of substantially the same genetic background with a nucleic acid molecule to obtain a recombinant plant cell; and
  (b) generating a transgenic plant from the recombinant plant cell,
wherein the transgenic plant recombinantly expresses a polypeptide selected from the group consisting of:
  (1) a polypeptide having an amino acid sequence that is at least about 80% identical to SEQ ID NO:2, wherein the amino acid sequence has a domain that is at least 80% identical to SEQ ID NO:70;
  (2) a polypeptide having an amino acid sequence that is at least about 80% identical to SEQ ID NO:4, wherein the amino acid sequence has a domain that is at least 80% identical to SEQ ID NO:71;
  (3) a polypeptide having an amino acid sequence that is at least about 80% identical to SEQ ID NO:6, wherein the amino acid sequence has a domain that is at least 80% identical to SEQ ID NO:72;
  (4) a polypeptide having an amino acid sequence that is at least about 80% identical to SEQ ID NO:8, wherein the amino acid sequence has a domain that is at least 80% identical to SEQ ID NO:73;
  (5) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74;
  (6) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75; and
  (7) a mutant class C20 GA2ox, the mutant C20 GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, and the domain III comprising the amino acid sequence of SEQ ID NO:17.

As used herein a "plant of substantially the same genetic background" refers to a plant that has substantially the same genotype, i.e., genetic constitution, as that of the transgenic plant according to an embodiment of the present invention, except that the plant does not recombinantly express a polypeptide selected from the group consisting of (1) to (7) above. The "plant of substantially the same genetic background" may contain an unmodified endogenous gene for a polypeptide selected from the group consisting of (1) to (7).

In addition to the gene alterations responsible for the recombinant expression of the polypeptide selected from the group consisting of (1) to (7) above, the transgenic plant can have one or more other genetic alterations resulting from the construction of the transgenic plant, such as an insertion, a deletion, or a disruption of certain gene or genomic sequences, as compared with the "plant of substantially the same genetic background." Preferably, such other genetic alterations do not result in significantly phenotypic changes to the transgenic plant.

In one embodiment of the present invention, the transgenic plant recombinantly expresses a polypeptide selected from the group consisting of (1) to (7) above from a transgene that is not found within the plant of substantially the same genetic background. The transgene is introduced into a cell of the plant of substantially the same genetic background to obtain a recombinant plant cell, which is subsequently used to generate the transgenic plant.

In another embodiment of the present invention, the transgenic plant recombinantly expresses a polypeptide selected from the group consisting of (1) to (7) above from a gene found within the plant of substantially the same genetic background, but the gene is modified and re-introduced into the transgenic plant by recombinant DNA technologies. The gene modifications can include changes to the coding sequence and/or regulatory sequences to alter the activity of the expressed polypeptide and/or the level of protein expression. For example, the endogenous gene can be cloned; the promoter for the endogenous gene can be replaced with a constitutive promoter or a stress-inducible promoter; the modified gene can be reintroduced into a cell of the plant of substantially the same genetic background to obtain a recombinant plant cell; and the recombinant plant cell is used to generate a transgenic plant. Unlike the plant of substantially the same genetic background, the resulting transgenic plant expresses the gene of interest constitutively or in a stress inducible fashion.

In one embodiment of the present invention, the recombinantly expressed polypeptide is encoded by a gene stably integrated into the genome of the transgenic plant cell, such as in a stable transgenic plant.

In another embodiment of the present invention, the recombinantly expressed polypeptide is encoded by a gene that remains on a vector inside the plant cell, such as in a transient transgenic plant.

In another general aspect, the present invention relates to a method of improving one or more traits of a plant selected from the group consisting of reduced height, increased tillering number, more biomass, a stronger and thicker stem, a stronger root system, more leaves, stable increase of yields and/or seed production, and enhanced stress tolerance. The method comprises increasing expression and/or activity of a gibberellin 2-oxidase or a derivative thereof in the plant.

In an embodiment of the present invention, the expression and/or activity of the gibberellin 2-oxidase or its derivative is increased by recombinant expression in the plant a polypeptide selected from the group consisting of:

(1) a polypeptide having an amino acid sequence that is at least about 80% identical to SEQ ID NO:2, wherein the amino acid sequence has a domain that is at least 80% identical to SEQ ID NO:70;

(2) a polypeptide having an amino acid sequence that is at least about 80% identical to SEQ ID NO:4, wherein the amino acid sequence has a domain that is at least 80% identical to SEQ ID NO:71;

(3) a polypeptide having an amino acid sequence that is at least about 80% identical to SEQ ID NO:6, wherein the amino acid sequence has a domain that is at least 80% identical to SEQ ID NO:72;

(4) a polypeptide having an amino acid sequence that is at least about 80% identical to SEQ ID NO:8, wherein the amino acid sequence has a domain that is at least 80% identical to SEQ ID NO:73;

(5) a polypeptide having an amino acid sequence that is at least about 80% identical to SEQ ID NO:10 or at least about 80% identical to SEQ ID NO:12, wherein the amino acid sequence has a domain that is at least 80% identical to the 2-ODD conserved domain of SEQ ID NO:10 or SEQU ID NO:12;

(6) a polypeptide having an amino acid sequence that is at least about 80% identical to SEQ ID NO:14 or at least about 80% identical to SEQ ID NO:16, wherein the amino acid sequence has a domain that is at least 80% identical to SEQ ID NO:75; and (7) a mutant class C20 GA2ox, the mutant GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, and the domain III comprising the amino acid sequence of SEQ ID NO:17.

In another embodiment of the present invention, the expression and/or activity of the gibberellin 2-oxidase or its derivative is increased by administering to the plant an agent that increases the expression and/or activity of the gibberellin 2-oxidase or its derivative in the plant. Such agent can be screened or identified using methods described herein.

In one embodiment of the present invention, the resulting transgenic plant recombinantly expresses a mutant class C20 GA2ox gene. The mutant class C20 GA2ox has at least one mutation in domain III of class C20 GA2ox and a reduced enzymatic activity to hydroxylate a class $C_{20}$-GA precursor compared with an otherwise identical wild-type class C20 GA2ox that lacks the at least one mutation in domain III.

According to embodiments of the present invention, the domain III comprises an amino acid sequence selected from the group consisting of SEQ ID NO:18, SEQ ID NO:19, SEQ ID NO:20, SEQ ID NO:21, SEQ ID NO:22 and SEQ ID NO:23; and the otherwise identical class C20 GA2ox comprises an amino acid sequence selected from the group consisting of: SEQ ID NO:2, SEQ ID NO:4, SEQ ID NO:10, SEQ ID NO:24, SEQ ID NO:25 and SEQ ID NO:26.

In another embodiment of the present invention, the resulting transgenic plant recombinantly expresses GA2ox selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:27, SEQ ID NO:28, SEQ ID NO:29, SEQ ID NO:30, SEQ ID NO:68 and SEQ ID NO:69.

The gene expression of the polypeptide of interest can be driven by a native promoter for the gene; a constitutive promoter such as maize ubiquitin (Ubi) promoter, a rice actin (Act1) promoter, and cauliflower mosaic 35S RNA promoter (CaMV35S) promoter; a tissue-specific promoter such as a rice glutelin (GluB) promoter, a rubisco small subunit (rbcs) promoter and a maize zean gene promoter; a developmental stage-specific promoter such as a rice alpha-amylase (αAmy) promoter and a rice glycine rich RNA binding protein (GRRP-A1) promoter; and an inducible promoter such as that inducible by drought, salt, high or low temperatures, hypoxia, anoxia, hydration, pH, chemicals, or hormones.

In an embodiment of the present invention, the inducible promoter is selected from the group consisting of promoters for the genes of *Arabidopsis* rd29A, cor15A, kin1, heat-shock factor (HSF), C-repeat-binding factor (CBF 1) and dehydration-responsive element binding protein (DREB1A); and promoters for the genes of rice HVA1 (ABA-inducible), alcohol dehydrogenase (Adh), ethanol-inducible, and alpha-amylase (GA-inducible).

In another embodiment of the present invention, the promoter drives gene expression in a developing seed during seed germination, in early seedlings or in growing plants.

Methods according to embodiments of the present invention can be applied to a dicot plant or a monocot plant. In an embodiment of the present invention, methods of the present invention can be applied to an agricultural plant, such as a rice plant; an ornamental plant; a grass used in pasture, ground cover, golf course, or turf; such as Bermuda grass and pangolagrass.

It is readily understood that the transgenic plant can be bred with other plants in order to combine additional desirable traits into one plant. The other plants can be transgenic or nontransgenic.

Methods according to embodiments of the present invention optionally comprise one or more screening steps for screening the one or more desirable traits in the transgenic plants using any screening method known in the art in view of the present disclosure.

In one embodiment of the present invention, the resulting transgenic plant has increased tolerance to one or more biotic stresses, such as that result from an invasion of the plant by a bacterium, a virus, a fungus, a parasite, a harmful insect, an algae, a nematode, or a weed.

In another embodiment of the present invention, the resulting transgenic plant has increased tolerance to one or more abiotic stresses, such as that result the negative impact of a high wind, an extreme temperature, drought, flood, a poor edaphic condition (like rock content, low or high pH, infertile soil, etc), high radiation, compaction, contamination, pollution, or rapid rehydration during seed germination.

This invention will be better understood by reference to the non-limiting examples that follow, but those skilled in the art will readily appreciate that the examples are only illustrative of the invention as described more fully in the claims which follow thereafter.

Identification of the Rice GA2ox Family

The preliminary computer search of the rice genome has identified 10 putative GA2ox genes. Three members of this gene family in rice had previously been found to encode GA2oxs with three unique and conserved domains, as with the class C20 GA2oxs of *Arabidopsis* and spinach (Lee and Zeevaart, 2005). Questions were thus raised as to whether all predicted rice GA2oxs are differentially expressed and regulated, and what their physiological functions in rice are.

Putative rice GA2oxs were sought by BLAST searching the NCBI, TIGR, and RiceGAAS databases with the conserved domain in the 2-oxoglutarate (2OG) and Fe (III)-dependent oxygenase family and nucleotide sequences of four previously identified rice GA2oxs (GA2ox1 to GA2ox4). A total of 10 putative GA2oxs were identified (Table 1). Among them, GA2ox1 to GA2ox4 had previously been partially characterized (Sakamoto, et al., 2001, 2004; Sakai et al., 2003), and GA2ox5 and GA2ox6 had been reported but remained uncharacterized (Lee and Zeevaart, 2005). Four other GA2oxs, designated here as GA2ox7 to GA2ox10, were identified in this study. Almost all GA2oxs encoded 300 to 400 amino acid residues, including the 2OG-Fe (II) oxygenase conserved domain. However, the predicted PI value of GA2ox10 is 9.3, which is significantly different from those of other GA2oxs with predicted PI values ranging from 5.0~7.2.

and others located on chromosomes 2, 4, and 7 (FIG. 1A). Amino acid sequence comparison (Table 2) generated a phylogenetic tree among the rice GA2ox family (FIG. 1B). GA2oxs located on the same chromosome have more amino acid sequence divergence from each other than from GA2oxs located on different chromosomes, indicating that gene duplication by crossing-over among chromosomes has occurred throughout their evolution.

The sequence identities of conserved domains of the deduced amino acids were compared. The identities were low among the 10 rice GA2oxs, indicating that these GA2oxs may play various roles (Table 3).

TABLE 1

Putative GA2ox gene family in rice (*Oryza sativa*)

| Gene Name | Chromosome | BAC No. | Site[a] | Locus[b] | Accession no. of cDNA | PI value | Amino acid |
|---|---|---|---|---|---|---|---|
| GA2ox1 | 5 | OSJNBa0017J22 | 8748~34623 | LOC__Os05g06670 | AK120967 | 6.52 | 403 |
| GA2ox2 | 1 | B1140D12 | 9818~19799 | LOC__Os01g22910 | | 6.64 | 370 |
| GA2ox3 | 1 | OJ1414__E05 | 66551~68322 | LOC__Os01g55240 | AK101713 | 6.26 | 327 |
| GA2ox4 | 5 | P0022D06 | 49345~50496 | LOC__Os05g43880 | AK107211 | 6.39 | 354 |
| GA2ox5 | 7 | P0446F04 | 52078~53103 | LOC__Os07g01340 | AK106859 | 5.88 | 341 |
| GA2ox6 | 4 | OSJNBa0019D11 | 138689~141990 | LOC__Os04g44150 | | 7.18 | 358 |
| GA2ox7 | 1 | P0466B10 | 35930~39272 | LOC__Os01g11150 | AK108802 | 6.67 | 335 |
| GA2ox8 | 5 | OJ1115__B06 | 55485~57032 | LOC__Os05g48700 | AK101758 | 6.03 | 353 |
| GA2ox9 | 2 | B1469H02 | 122528~120151 | LOC__Os02g41954.1 | Ak059045 | 5.58 | 359 |
| | | | | LOC__Os02g41954.2 | AK108598 | 5.04 | 299 |
| GA2ox10 | 5 | OSJNBb0016G07 | 9180~13210 | LOC__Os05g11810.1 | | 9.37 | 378 |
| | | | | LOC__Os05g11810.2 | | 9.33 | 271 |

[a]The critical site of BAC clone.
[b]Locus was identified by the TIGR Rice Pseudomolecules and Genome Annotation 5.0 (www.tigr.org/tdb/e2k1/osa1/), but the relative cDNA clone of GA2ox10 could not be found. GA2ox1 to GA2ox4 were identified by Sakamoto et al. (2001, 2004). GA2ox5 and GA2ox6 were nominated by Lee and Zeevaart (2005). GA2ox7 to GA2ox11 were nominated in this study, based on the sequence similarity search and gene annotation using the NCBI, TIGR and RiceGAAS databases.

The locations of GA2oxs in the rice genome were determined, with seven GA2oxs clustered on chromosome 1 and 5

TABLE 2

Comparison of deduced amino acids among rice GA2oxs

| | GA2ox5 | GA2ox6 | GA2ox9 | GA2ox1 | GA2ox2 | GA2ox10 | GA2ox7 | GA2ox3 | GA2ox4 | GA2ox8 |
|---|---|---|---|---|---|---|---|---|---|---|
| GA2ox5 | 100 | 62 | 63 | 38 | 43 | 22 | 47 | 50 | 47 | 45 |
| GA2ox6 | | 100 | 76 | 36 | 41 | 20 | 44 | 46 | 44 | 44 |
| GA2ox9 | | | 100 | 34 | 39 | 19 | 43 | 45 | 42 | 42 |
| GA2ox1 | | | | 100 | 66 | 24 | 49 | 50 | 49 | 51 |
| GA2ox2 | | | | | 100 | 32 | 56 | 57 | 56 | 57 |
| GA2ox10 | | | | | | 100 | 41 | 38 | 35 | 35 |
| GA2ox7 | | | | | | | 100 | 70 | 63 | 64 |

TABLE 2-continued

Comparison of deduced amino acids among rice GA2oxs

|  | GA2ox5 | GA2ox6 | GA2ox9 | GA2ox1 | GA2ox2 | GA2ox10 | GA2ox7 | GA2ox3 | GA2ox4 | GA2ox8 |
|---|---|---|---|---|---|---|---|---|---|---|
| GA2ox3 |  |  |  |  |  |  |  | 100 | 73 | 70 |
| GA2ox4 |  |  |  |  |  |  |  |  | 100 | 67 |
| GA2ox8 |  |  |  |  |  |  |  |  |  | 100 |

TABLE 3

Identities of conserved domains among rice GA2oxs

|  | GA2ox5 | GA2ox6 | GA2ox9 | GA2ox1 | GA2ox2 | GA2ox10 | GA2ox7 | GA2ox3 | GA2ox4 | GA2ox8 |
|---|---|---|---|---|---|---|---|---|---|---|
| GA2ox5 | 100 | 79 | 83 | 51 | 50 | 44 | 50 | 53 | 54 | 55 |
| GA2ox6 |  | 100 | 87 | 51 | 51 | 46 | 55 | 54 | 53 | 56 |
| GA2ox9 |  |  | 100 | 50 | 50 | 44 | 51 | 50 | 50 | 54 |
| GA2ox1 |  |  |  | 100 | 74 | 57 | 64 | 68 | 66 | 68 |
| GA2ox2 |  |  |  |  | 100 | 58 | 70 | 70 | 66 | 67 |
| GA2ox10 |  |  |  |  |  | 100 | 65 | 64 | 62 | 59 |
| GA2ox7 |  |  |  |  |  |  | 100 | 83 | 75 | 77 |
| GA2ox3 |  |  |  |  |  |  |  | 100 | 82 | 84 |
| GA2ox4 |  |  |  |  |  |  |  |  | 100 | 75 |
| GA2ox8 |  |  |  |  |  |  |  |  |  | 100 |

Figure 11:
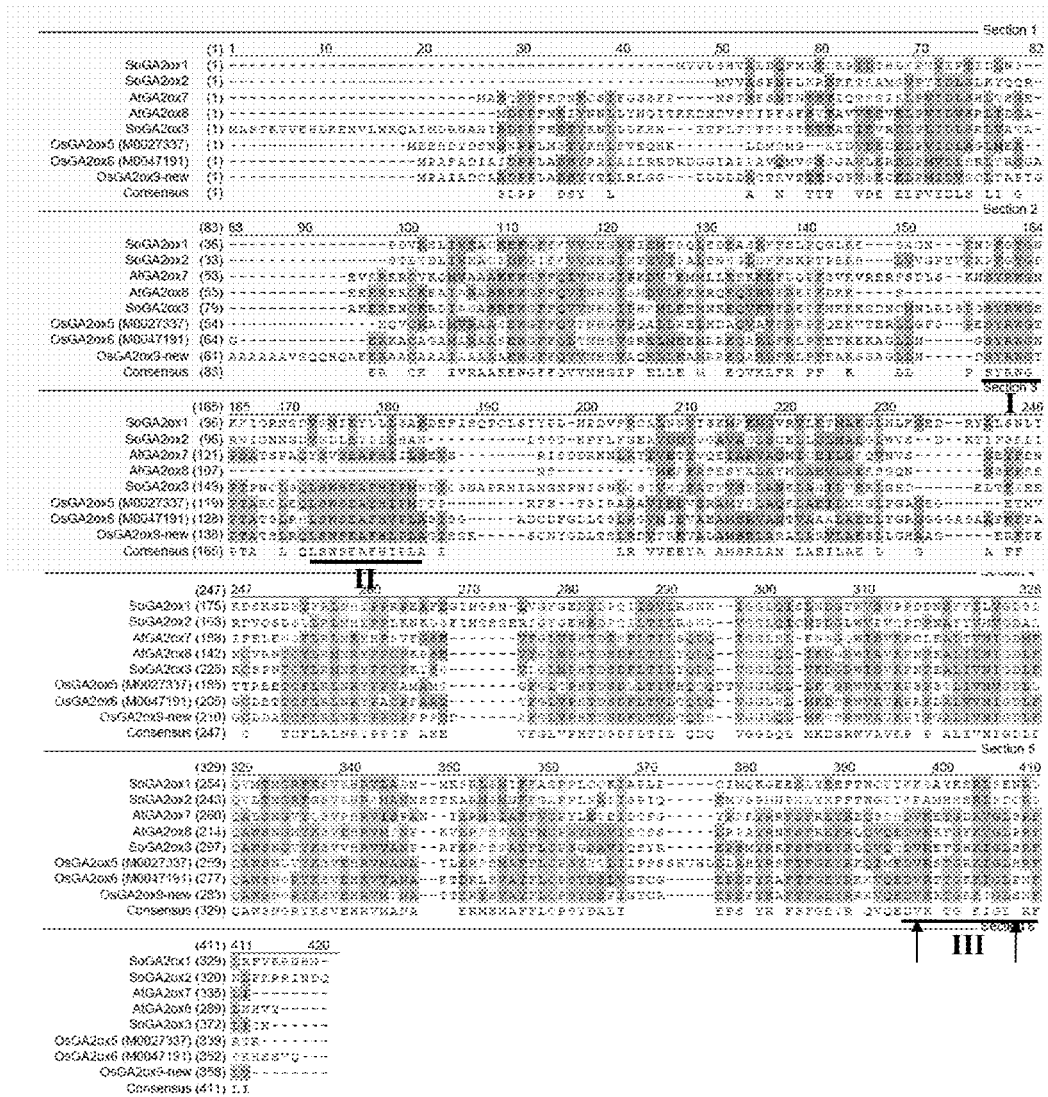
FIG. 11 illustrates amino acid sequence alignment of rice GA2oxs, including OsGA2ox5 (SEQ ID NO: 2), OsGA2ox6 (SEQ ID NO:4) and OsGA2ox9 (SEQ ID NO: 10); Arabidopsis GA2oxs, including AtGA2ox7 (SEQ ID NO: 24) and AtGA2ox8 (SEQ ID NO:25); and spinach GA2ox, including SoGA2ox3 (SEQ ID NO: 26), using the Vector NTI 6.0 software (InforMax, Inc.), wherein these GA2oxs contain three highly conserved domains (underlined) that are absent in other GA2oxs (Lee and Zeevaart, 2005)

Amino acid sequence comparison also generated a phylogenetic tree of 10 rice GA2oxs and 19 GA2oxs from 8 dicot plant species (Table 3), which revealed that rice GA2ox5, GA2ox6 and GA2ox9 are more closely related to the *Arabidopsis* GA2ox7 and GA2ox8 and spinach GA2ox3 (FIG. 1C). These six GA2oxs contain three unique and conserved domains (Lee and Zeevaart, 2005) (FIG. 11).

TABLE 4

Gene names and accession number of 19 GA2oxs from different plant species

| Name | Species | Accession Number |
|---|---|---|
| AtGA2ox1 | *Arabidopsis thaliana* | AJ132435 |
| AtGA2ox2 | *Arabidopsis thaliana* | AJ132436 |
| AtGA2ox3 | *Arabidopsis thaliana* | AJ132437 |
| AtGA2ox4 | *Arabidopsis thaliana* | AY859740 |
| AtGA2ox6 | *Arabidopsis thaliana* | AY859741 |
| AtGA2ox7 | *Arabidopsis thaliana* | NM103976 |
| AtGA2ox8 | *Arabidopsis thaliana* | NM118239 |
| CmGA2ox | *Cucurbita maxima* | AJ302041 |
| LsGA2ox1 | *Lactuca sativa* | AB031206 |
| NtGA2ox1 | *Nicotiana sylvestris* | AB125232 |
| NtGA2ox3 | *Nicotiana sylvestris* | EF471117 |
| NtGA2ox5 | *Nicotiana sylvestris* | EF471118 |
| PcGA2ox1 | *Phaseolus coccineus* | AJ132438 |
| Poplar GA2ox1 | *Populus alba × P. tremuloides* | AY392094 |
| PsGA2ox1 | *Pisum sativum* | AF056935 |
| PsGA2ox2 | *Pisum sativum* | AF100954 |
| SoGA2ox1 | *Spinacia oleracea* | AF506281 |
| SoGA2ox2 | *Spinacia oleracea* | AF506282 |
| SoGA2ox3 | *Spinacia oleracea* | AY935713 |

Differential Expression of GA2ox Correlated with Flower and Tiller Development

Growth of the rice cultivar TNG67 used in the present study could be divided into vegetative, reproductive and ripening phases (FIG. 2A). To understand the role that individual GA2oxs may play in rice growth, the temporal expression patterns of GA2oxs in rice during the rice life cycle was examined. As leaves have been shown to be a major site of GA biosynthesis (Choi et al., 1995), fully expanded leaves at different growth or developmental stages ranging from 5 to 100 days after imbibition (DAI) were collected. The different growth or developmental stages include seedling from about 1-20 DAI, tillering from about 30-40 DAI, reproductive from about 60-90 DAI and ripening at about 100 DAI. Total RNAs were isolated from the leaves. The expression levels of GA2ox mRNA were analyzed by RT-PCR using GA2ox and GA3ox2 gene-specific primers (Table 7), and the 18S rRNA gene (rRNA) was used as a control.

It was observed that the genes GA2ox1 to GA2ox9 were differentially expressed in leaves and the expression was temporally regulated. However, mRNAs of GA2ox10 was not detected in any tissue in any growth stage, indicating GA2ox10 may be a pseudogene or its mRNA level was too low to be detected. Based on temporal mRNA accumulation patterns, the GA2oxs could be classified into 2 groups. As can be seen in FIG. 2B, for members of group A, which exclude GA2ox2 and GA2ox6, accumulation of their mRNAs in leaves was detected prior to the transition from vegetative to reproductive growth phases. In contrast, for members of group B, which include GA2ox2 and GA2ox6, their mRNAs accumulated in leaves after the phase transition from vegetative to reproductive growth. GA2ox6 mRNA could also be detected in leaves at early seedling stage and transiently at high level during active tillering stage.

Figure 2:
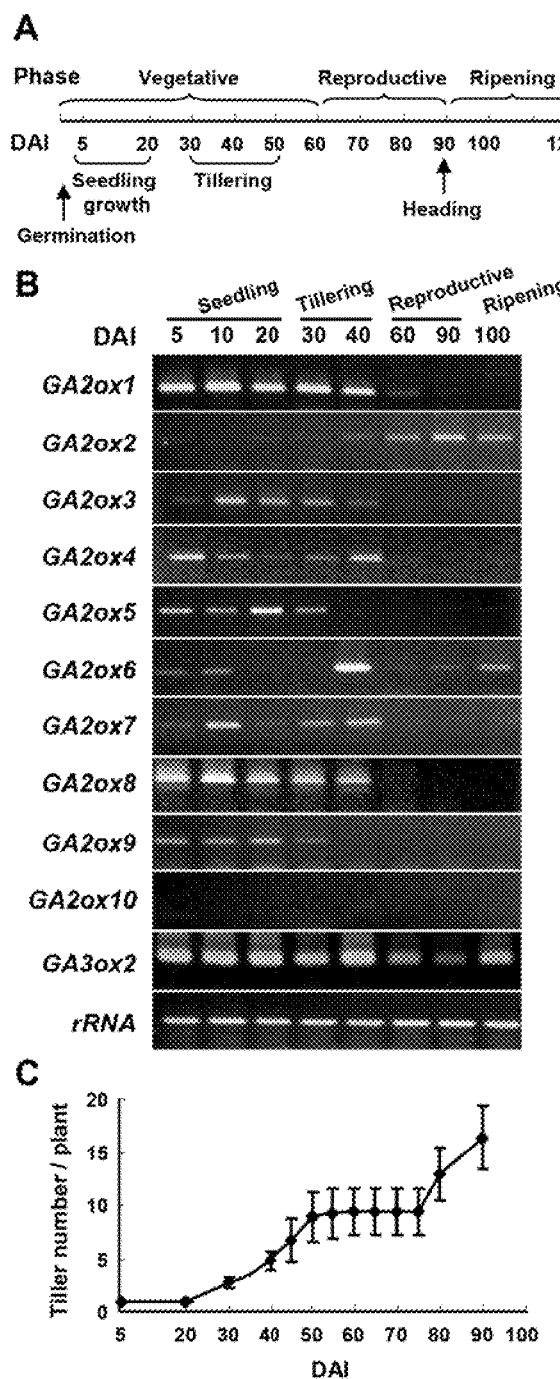
FIGS. 2A-2C illustrate differential expression of GA2oxs that correlated with flower and tiller development.

Since expression of most GA2oxs terminated after tillering, the pattern of tiller growth throughout the rice life cycle was examined. Tiller number increased from 30 to 50 DAI, remained constant until 75 DAI, and then increased again until 90 DAI when the experiment was terminated (FIG. 2C). Expression of group A and group B GA2oxs paralleled the increase in tiller number in the vegetative and reproductive phases, respectively (FIG. 2, compare B with C). Except for a slight reduction in the reproductive phase, the expression of GA3ox2, which encodes the enzyme involved in GA biosynthesis, was not significantly altered in leaves throughout the rice life cycle. These results suggest that up- and down-regulation of group A GA2oxs may control GA levels for tiller growth in the vegetative phase and for flower development in the reproductive phase, respectively, while up-regulation of group B GA2oxs controls tiller growth in the reproductive phase.

Decrease in GA2ox6 Expression Correlated with Seed Germination

Figure 3:
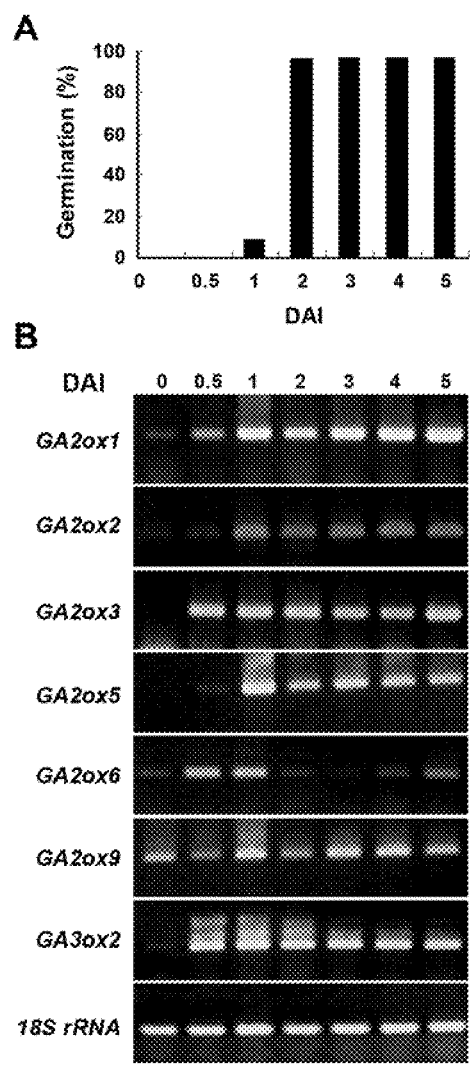
FIGS. 3A and 3B illustrate decrease in GA2ox6 expression that correlated with seed germination.

Bioactive-GAs are well-known to be responsible for relieving seed dormancy and promoting germination, so the role of GA2oxs during germination was studied. Seeds were imbibed for various lengths of time. Germination of wild-type seeds was observed from 1 DAI which reached almost 100% at 2 DAI (FIG. 3A). Total RNAs were isolated from embryos after imbibition of seeds, and temporal expression profiles of six GA2oxs were analyzed by RT-PCR. Accumulation of most GA2ox mRNAs was detectable starting from 0 to 1 DAI, which was maintained at similar levels afterward (FIG. 3B). GA2ox6 had a distinct expression pattern as its mRNA quickly accumulated from 0.5 to 1 DAI and then decreased significantly from 2 to 4 DAI. Low-level accumulation of GA3ox mRNA was detected at 0 DAI and then at similarly high levels after 0.5 DAI. This study demonstrated that most GA2oxs were constitutively expressed and competed with GA3ox for GA, while only GA2ox6 was transiently expressed and its reduced expression correlated with the rapid seed germination at 2 DAI.

Figure 4:
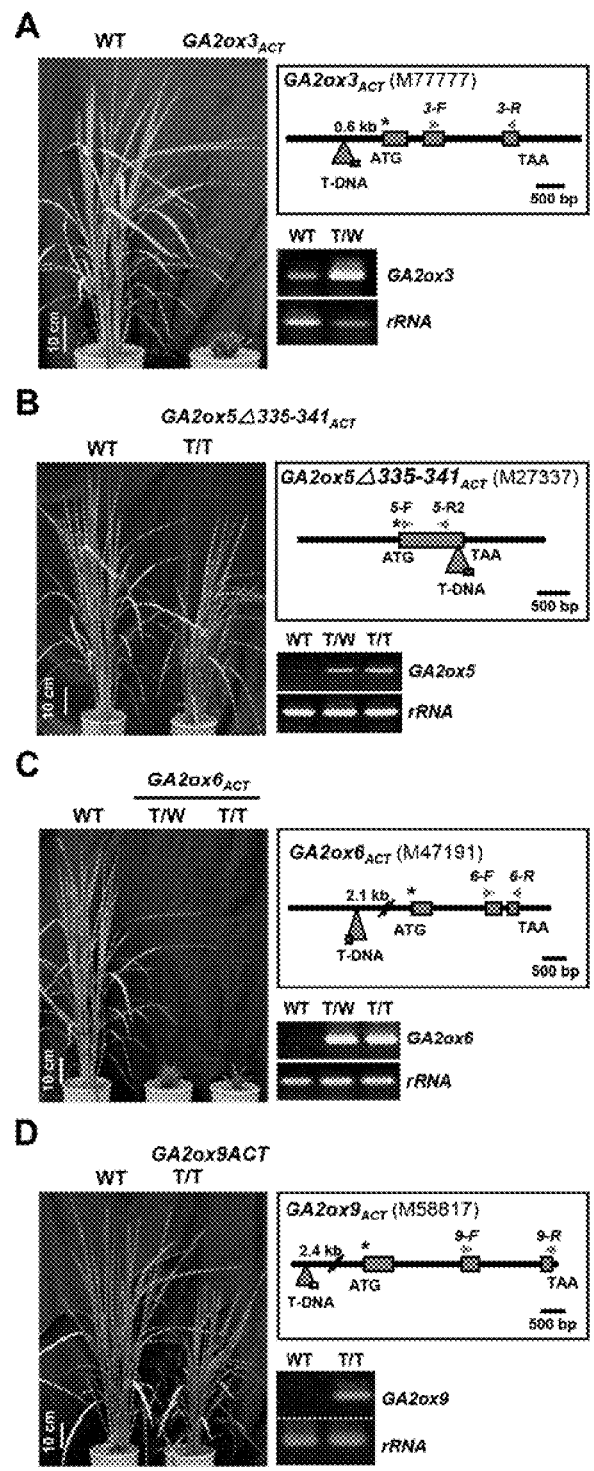
FIGS. 4A-4D illustrate four GA2ox mutants identified from the TRIM mutant library.

Plant Growth and Seed Germination were Impaired in T-DNA Tagged Rice Mutants Overexpressing GA2oxs To study the functions of GA2oxs in rice, mutants in a T-DNA tagged rice mutant library, the Taiwan Rice Insertional Mutagenesis (TRIM) library (Hsing et al., 2007), were screened. The T-DNA tag used for generating the TRIM library contained multiple CaMV35S enhancers adjacent to the right border, which activate promoters located close to T-DNA insertion sites (Hsing et al., 2007). Two GA2ox-activated dwarf mutants, M77777 and M47191, were identified by a forward genetic screen and another two mutants, M27337 and M58817, were identified by a reverse genetic screen of the library (FIG. 4).

The severely dwarf mutant M77777, designated as GA2ox3$_{ACT}$, carries a T-DNA insertion at a position 587 by upstream of the translation start codon of GA2ox3 (FIG. 4A). Accumulation of GA2ox3 mRNA in this mutant was significantly enhanced in the heterozygous mutant. GA2ox3$_{ACT}$ mutant did not produce seeds and was therefore maintained and propagated vegetatively.

The semi-dwarf mutant M27337, designated as GA2ox5Δ335-341$_{ACT}$, carries a T-DNA insertion in the coding region, at a position 23 by upstream of the translation stop codon of GA2ox5 (FIG. 4B). Truncation of GA2ox5 by T-DNA resulted in a loss of 4 amino acids at the C-terminal of the putative GA2ox5 polypeptide. Accumulation of the truncated GA2ox5 mRNA was significantly enhanced by T-DNA activation tagging in both homozygous and heterozygous mutants, but the semi-dwarf phenotype was observed only in the homozygous mutant. The GA2ox5Δ335-341$_{ACT}$ homozygous mutant had an average plant height 90%, and produced seeds with an average fertility 88%, of the wild type (Table 5). These results suggest that the truncated GA2ox5 mRNA might encode a partially functional GA2ox5.

TABLE 5

Characterization of rice mutants and transgenic rice overexpressing GA2oxs

| Traits | Wild type | GA2ox5Δ335-341$_{ACT}$ (T3)[a] | GA2ox9$_{ACT}$ (T3) | GA2ox6$_{ACT}$ (T2) | Ubi::GA2ox5 (T1) | Ubi::GA2ox6 (T1) |
|---|---|---|---|---|---|---|
| Tiller number of seedling (18 DAI) | 1.0 ± 0.0[b] (100)[c] | 1.8 ± 0.8 (180) | 1.0 ± 0.0 (100) | 2.6 ± 0.5 (260) | 2.7 ± 0.6 (270) | 2.5 ± 0.7 (250) |
| Root length (cm) at 18 DAI | 6.3 ± 0.9 (100) | 15.7 ± 3.2 (249) | 11.0 ± 1.9 (175) | 5.8 ± 1.8 (92) | 6.3 ± 2.1 (100) | 6.6 ± 0.4 (105) |
| Plant height (cm) at 120 DAI | 109.5 ± 2.5 (100) | 98.0 ± 7.1 (90) | 83.2 ± 4.1 (76) | 16.6 ± 1.7 (15) | 16.7 ± 2.8 (15) | 12.1 ± 2.7 (11) |
| Length of the leaf below flag leaf (cm) at 120 DAI | 49.9 ± 6.0 (100) | 49.6 ± 5.1 (100) | 49.3 ± 3.3 (99) | 12.2 ± 0.9 (24) | 10.6 ± 1.2 (21) | 8.1 ± 0.8 (16) |
| Width of the leaf below flag leaf (cm) at 120 DAI | 1.64 ± 0.1 (100) | 1.66 ± 0.1 (101) | 1.75 ± 0.2 (107) | 1.51 ± 0.1 (92) | 1.2 ± 0.1 (73) | 1.04 ± 0.1 (63) |
| Heading day (DAI) | 108.7 ± 1.5 | 107.6 ± 1.3 | 107.9 ± 1.0 | >150 | >150 | >150 |
| Panicle length (cm) | 21.6 ± 2.0 (100) | 20.3 ± 1.5 (94) | 19.7 ± 1.8 (91) | 7.7 ± 1.6 (36) | 5.9 ± 0.8 (27) | 7.5 ± 0.9 (35) |
| Final Tiller number | 11.0 ± 1.8 (100) | 20.3 ± 4.1 (185) | 13.4 ± 2.9 (122) | 17.6 ± 3.7 (160) | NA | 18.8 ± 4.5 (171) |
| Grain weight (g/100 grains) | 2.44 ± 0.1 (100) | 2.04 ± 0.1 (84) | 2.34 ± 0.2 (96) | 1.54 (63) | 1.43 (59) | 1.98 (81) |
| Fertility (%) | 92.6 ± 4.2 (100) | 81.1 ± 5.4 (88) | 85.4 ± 8.9 (92) | 39.5 ± 18 (43) | 27.7 ± 12.0 (30) | 59.4 ± 4.4 (64) |

[a]T1, T2 and T3 in parenthesis indicate generation of mutants.
[b]SE; n = 20 for GA2ox5Δ335-341$_{ACT}$, GA2ox9$_{ACT}$, and GA2ox6$_{ACT}$; n = 10 for Ubi::GA2ox5 and Ubi::GA2ox6.
[c]Values in parentheses indicate % of the wild type.
NA: not available.
DAI: days after imbibition.

The severely dwarf mutant M47191, designated as GA2ox6$_{ACT}$, carries a T-DNA insertion at a position 2.1 kb upstream of the translation start codon of GA2ox6 (FIG. 4C). Accumulation of GA2ox6 mRNA was significantly enhanced by T-DNA activation tagging, and severely dwarf phenotype was observed in both heterozygous and homozygous mutants. The GA2ox6$_{ACT}$ homozygous mutant produced seeds with an average fertility of only 43% of the wild type after more than 5 months of growth (Table 5).

The semi-dwarf mutant M58817, designated as GA2ox9$_{ACT}$, carries a T-DNA insertion at a position 2.4 kb upstream of the translation start codon of GA2ox9 (FIG. 4D). Accumulation of GA2ox9 mRNA was significantly enhanced by T-DNA activation tagging, and the semi-dwarf phenotype was observed in both homozygous and heterozygous mutant. The GA2ox9$_{ACT}$ homozygous mutant produced seeds with an average fertility of 92% of the wild type (Table 4).

Figure 5:
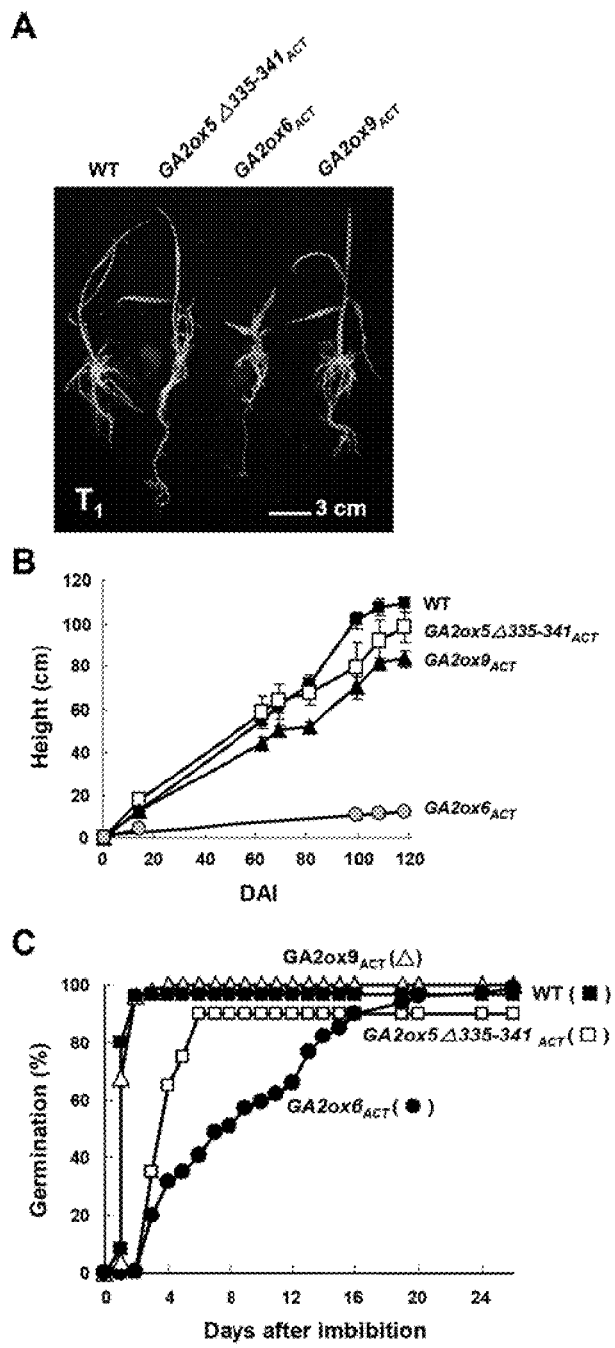
FIGS. 5A-5C illustrate that activation of GA2oxs expression had different effect on seed germination and seedling growth.

The three activation-tagged mutants, GA2ox5Δ335-341$_{ACT}$, GA2ox6$_{ACT}$ and GA2ox9$_{ACT}$ were further characterized. Mutant seedlings and plants displayed the same phenotypes as their parents, with GA2ox5Δ335-341$_{ACT}$ growing slightly shorter and GA2ox9$_{ACT}$ shorter still than the wild type, while GA2ox6$_{ACT}$ remained severely dwarfed throughout all growth stages (FIG. 5, A and B). GA2ox5Δ335-341$_{ACT}$ and GA2ox9$_{ACT}$ displayed a rather normal phenotype, except for longer roots and higher tiller numbers than the wild type (Table 5). Other phenotypes significantly altered in the severely dwarf GA2ox6$_{ACT}$ mutant included shorter leaf length, longer heading day, shorter panicle length, higher tiller numbers, lower grain weight and lower seed fertility as compared with the wild type (Table 5). Germination of GA2ox6$_{Act}$ seeds was also significantly delayed, as it took 20 days to reach 90% germination rate, while the wild type and GA2ox9$_{ACT}$ mutant seeds took only 2 days to reach a germination rate of 97% and 98%, respectively (FIG. 5C). Germination of GA2ox5Δ335-341$_{ACT}$ seeds was delayed for 4 days to reach a final 88% germination rate (FIG. 5C).

Figure 6:
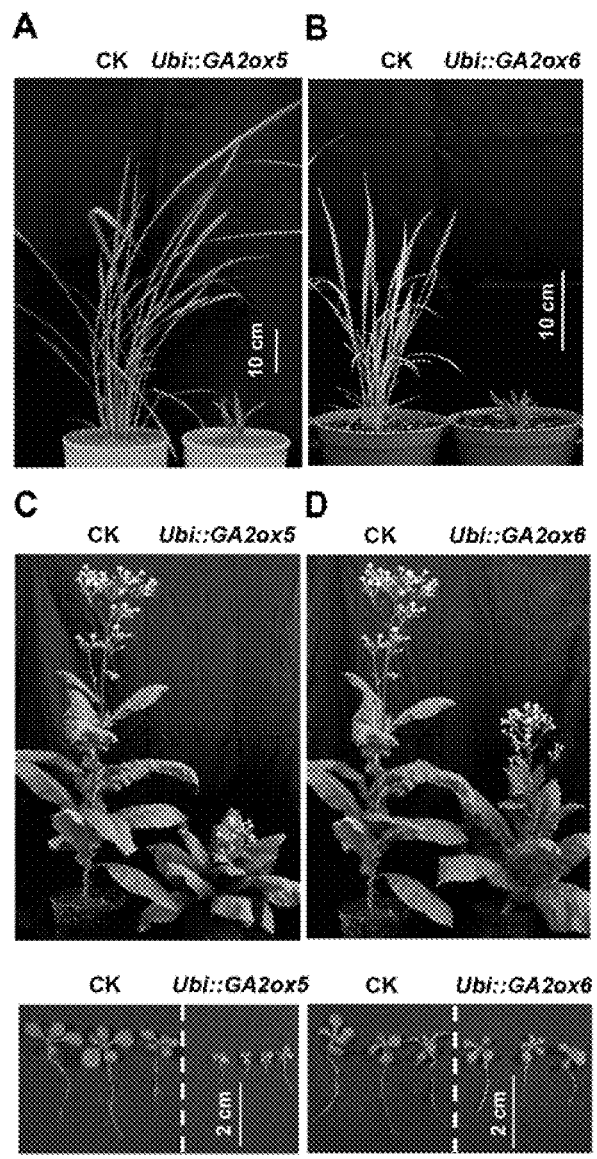
FIGS. 6A-6D illustrate that overexpression of GA2ox5 and GA2ox6 recapitulated the dwarf phenotypes in transgenic rice and tobacco.

Overexpression of GA2ox5 and GA2ox6 Recapitulated the Dwarf or Semi-Dwarf Phenotypes in Transgenic Rice and Tobacco To verify the function of GA2ox5 and GA2ox6 in dwarfism of rice plants, full length cDNAs of GA2ox5 and GA2ox6 were isolated from rice and fused downstream of the maize ubiquitin (Ubi) promoter, generating Ubi::GA2ox5 and Ubi::GA2ox6 constructs for rice transformation. More than 30 independent transgenic rice lines were obtained for each construct. All transgenic rice plants showed dwarf phenotypes, although slight variations in final height were observed. The overall phenotypes of Ubi::GA2ox5 and Ubi::GA2ox6 T$_1$ plants were similar to the GA2ox6$_{ACT}$ mutant, except that the seed fertility produced by Ubi::GA2ox6 transgenic rice (average 64%) was higher than of Ubi::GA2ox5 transgenic rice (average 30%) (FIG. 6, A and B and Table 5). RT-PCR analysis showed that both GA2ox5 and GA2ox6 mRNAs accumulated at similar high levels in all transgenic lines (data not shown). These results demonstrated that ectopic overexpression of GA2ox5 or GA2ox6 was able to recapitulate the dwarf phenotype in transgenic rice. They also suggest that the nearly normal phenotype of GA2ox5Δ335-341$_{ACT}$ mutant could be due to overexpression of a GA2ox5 product missing part of domain III.

Ectopic overexpression of *Arabidopsis* GA2ox7 and GA2ox8 and spinach GA2ox3 reduced the bioactive GA content and resulted in a dwarf phenotype of transgenic tobacco plants (Schomburg et al., 2003; Lee and Zeevaart, 2005). To examine whether rice GA2oxs are also functional in dicots, Ubi::GA2ox5 and Ubi::GA2ox6 constructs were used for tobacco transformation.

Ectopic overexpression of these two rice GA2oxs in transgenic tobacco revealed the same retardation of plant growth, but with different effects. While Ubi:: GA2ox5 reduced plant height to 32% and seed production to 62%, and Ubi::GA2ox6 reduced plant height to 67% of the wild type tobacco, Ubi:: GA2ox6 had no effect on seed production (FIGS. 6C and D, upper panels, and Table 6). The numbers of leaves to inflorescence were not different between the transgenic and wild type tobacco, but the flowering time was delayed approximately 2 to 4 weeks for all transgenic tobacco. Growth of hypocotyls and roots of 18-day-old T$_1$ transgenic tobacco seedlings was slightly retarded by overexpression of GA2ox6, but significantly retarded by overexpression of GA2ox5, compared with the wild type (FIGS. 6C and D, lower panels, and Table 6). These studies demonstrated that the two rice GA2oxs have similar functions in monocots and dicots, with GA2ox5 being more potent in inactivation of GA than GA2ox6 in both transgenic rice and tobacco.

TABLE 6

Characterization of transgenic tobacco overexpressing rice GA2ox5 and GA2ox6

| Traits | Wild Type | Ubi::GA2ox5 | Ubi::GA2ox6 |
|---|---|---|---|
| Root length (mm) at 18 DAI | 20.8 ± 2.7$^a$ (100)$^b$ | 9.6 ± 4.6 (46) | 17.7 ± 3.6 (85) |
| Hypocotyl length (mm) at 18 DAI | 6.5 ± 0.8 (100) | 3.2 ± 0.6 (49) | 4.6 ± 1.0 (71) |
| Final Plant height (cm) | 127.7 ± 4.7 (100) | 41.2 ± 18.9 (32) | 85.3 ± 9.4 (67) |
| Number of leaves to inflorescence | 18.3 ± 0.6 (100) | 20.8 ± 3.3 (114) | 19.0 ± 0.8 (104) |
| Seeds yield (g)/plant | 31.1 (100) | 19.3 ± 3.4 (62) | 31.3 ± 4.1 (100) |

$^a$SE with n = 40.
$^b$Values in parentheses indicate % of the wild type.

Figure 7:
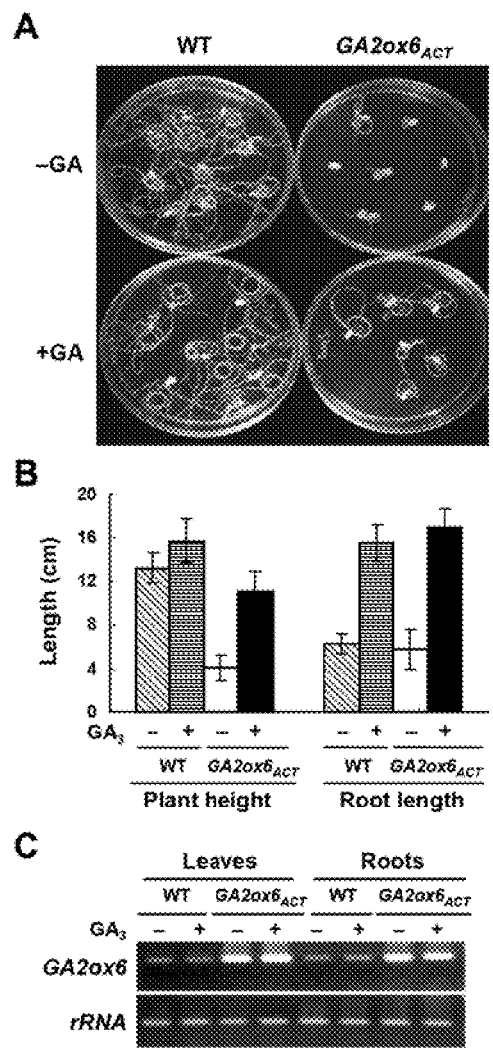
FIGS. 7A-7C show that overexpression of GA2ox6 reduced GA levels in rice mutant in which only shoot but not root growth was affected.

Overexpression of GA2ox6 Reduced GA Levels in Rice Mutants in which Only Shoot but not Root Growth was Affected To determine whether the dwarfism of rice mutants overexpressing GA2ox was a result of a reduction of bio-active GAs, GA2ox6$_{ACT}$ mutant seeds were germinated on MS agar medium with or without supplementation with 5 μM GA$_3$. Addition of GA$_3$ promoted germination of GA2ox6$_{ACT}$ seeds (FIG. 7A), indicating that an insufficient endogenous GA concentration was responsible for the reduced germination of GA2ox6$_{ACT}$ mutant seeds. Plant height of 18-day-old wild-type seedlings was only slightly enhanced by GA$_3$ treatment; in contrast, height of the dwarf GA2ox6$_{ACT}$ mutant seedlings was significantly enhanced by GA$_3$ treatment, with recovery of up to 84% of the wild type (FIG. 7B). Root lengths of the wild type and GA2ox6$_{ACT}$ mutant seedlings were similar, and both were effectively enhanced by GA$_3$ treatment (FIG. 7B).

Figure 12:
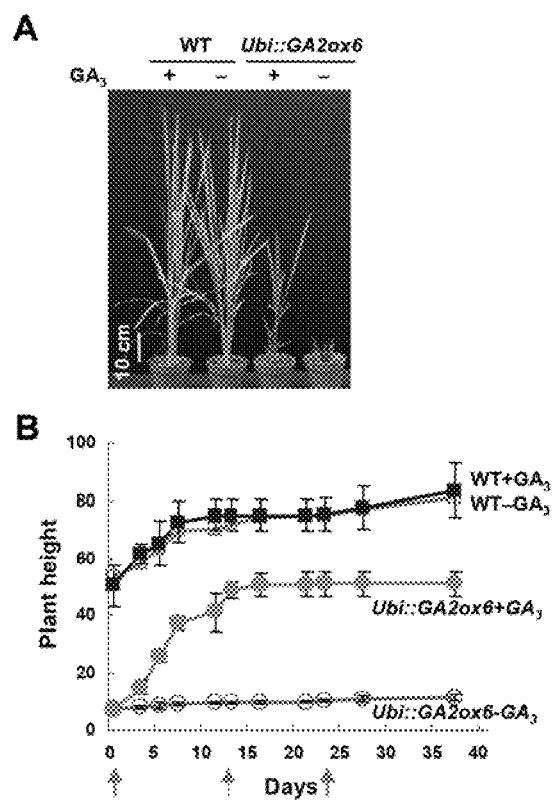
FIGS. 12 A and 12 B show dwarfism of Ubi::GA2ox6 transgenic rice that is partially rescued by $GA_3$: Wild type (WT) and Ubi::GA2ox6 transgenic rice grown in pot soil were treated with (+) or without (−) 10 µM $GA_3$ at a 12-day interval for 5 weeks; the height of WT plant was not altered, while that of transgenic plant was enhanced, by $GA_3$ treatment.

It was noticed that root growth of GA2ox6$_{ACT}$ was significantly slower initially after germination (FIG. 7A, upper panel), but it sped up after 6 DAI and became similar to the wild type at 18 DAI (FIG. 7B). A similar phenomenon was observed for other mutants and Ubi:: GA2ox5 and Ubi:: GA2ox6 transgenic rice. GA2ox6 mRNA in leaves and roots accumulated to a higher level in the GA2ox6$_{ACT}$ mutant than in the wild type, but both were unaffected by GA$_3$ treatment (FIG. 7C), indicating that plant and root growth was promoted by GA$_3$ and was not related to GA2ox6 expression. These results suggest that reduction of GA levels affected only stem and leaf growth but not root growth. Additionally, GA$_3$ treatment could compensate for the decrease in endogenous GA concentration and recover seed germination and plant growth of the GA2ox6$_{ACT}$ mutant (FIG. 12), suggesting that GA responsiveness was not affected in the mutant.

Figure 8:
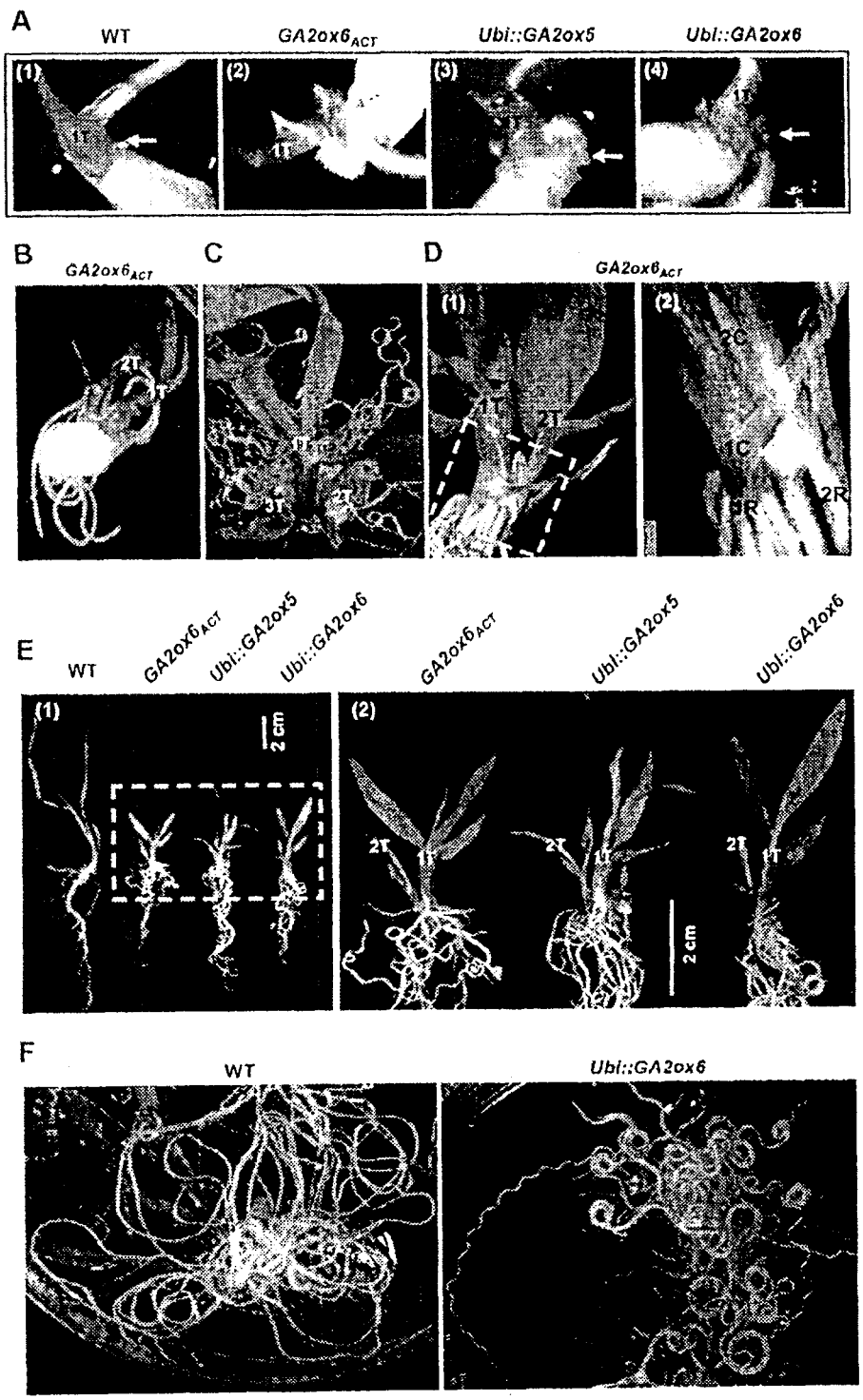
FIG. 8 B shows that a second tiller (2T) grew out from the swollen embryo surface of mutant and transgenic rice (photo taken at 9 DAI)
Figure 9:
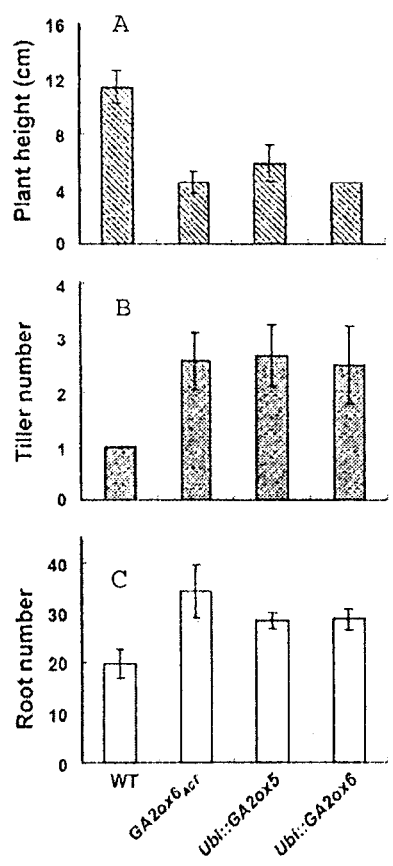
FIGS. 9A-C show that overexpression of GA2ox5 and GA2ox6 decreased plant heights, but increased tiller numbers and root numbers.

Overexpression of GA2ox5 and GA2ox6 Promoted Early Tiller and Adventitious Root Growth and Affected Root Architecture Normally, the rice wild type forms tillers 30 days after seed imbibition (FIG. 2C). It was found that rice mutants or transgenic rice overexpressing GA2oxs formed tillers not only with higher number but also much earlier than the wild type. In the GA2ox6$_{ACT}$ mutant and Ubi:: GA2ox5 and Ubi:: GA2ox6 transgenic seedlings, after growth of the first seedling/tiller from the embryo at 2 DAI, a subsequent swelling on the embryo surface adjacent to the base of the first seedling/tiller was observed at 3 DAI (FIG. 8A, panels 2 to 4). Then a second and even a third seedling/tiller grew out from the swelled embryo surface from 9 to 15 DAI (FIG. 8, B and C). Each tiller grew out from its own coleoptile (FIG. 8D), suggesting these tillers developed independently in the embryo. Both the mutant and transgenic seedlings showed early tillering (FIG. 8E). The swollen embryo surface where a second shoot was about to emerge was not observed in the wild type (FIG. 8A, panel 1). All new tillers in the mutant and transgenic rice had their own adventitious roots (FIG. 8D), a feature similar to tillers from the wild type plant around 30 DAI. Despite some retardation of shoot elongation, root length appeared normal; however, roots of mutant and transgenic seedlings became very curled and zigzag in shape, compared to the wild type (FIG. 8F). Quantitation of the data also revealed that only stem elongation was inhibited, while tiller and root numbers for 18-day-old mutant and transgenic rice were enhanced, as compared with the wild type (FIG. 9).

GA2ox5 and GA2ox6 Specifically Inactivated $C_{20}$-GA Precursors and Reduce GA Biosynthesis To examine if GA metabolism in the rice GA2ox6$_{ACT}$ mutant (M47191) was altered, crude extracts containing GA were prepared from leaves of 18-day-old seedlings and mature plants and subjected to a GC-MS-selected ion monitoring method for identification of GA compounds (Lee and Zeevaart., 2002). In seedling and mature leaves, the level of $GA_1$ was much lower in mutants (0.1 and 0 ng/g, respectively) than in the wild type (0.6 and 0.7 ng/g, respectively); in contrast, the level of $GA_{97}$ was much higher in mutants (28.7 and 10.8 ng/g, respectively) than in the wild type (3.6 and 0.5 ng/g, respectively) (Table 7).

TABLE 7

GAs content in GA2ox6$_{ACT}$ mutant and the wild type

| Sample | $GA_1$ | $GA_{97}$ |
| --- | --- | --- |
| Leaves from seedlings at 18 DAI | | |
| GA2ox6$_{ACT}$ | 0.1* | 28.7 |
| Wild type | 0.6 | 3.6 |
| Leaves from mature plants | | |
| GA2ox6$_{ACT}$ | 0.0 | 10.8 |
| Wild type | 0.7 | 0.5 |

*GA content in ng/g dry weight.

$GA_{53}$, a precursor of $GA_1$, could be converted to $GA_{97}$ in vitro by the *Arabidopsis* class C20 GA2ox through 2β-hydroxylation (Schomburg et al., 2003). The in vitro activity of rice GA2ox5 and GA2ox6 were also investigated by overexpression as fusion proteins with glutathione S-transferase in *E. coli*. Fusion proteins were partially purified and their enzyme activity analyzed. Both proteins could convert $GA_{53}$ to $GA_{97}$, an activity similar to the *Arabidopsis* GA2ox7 and GA2ox8 (Schomburg et al., 2003) and spinach GA2ox3 (Lee and Zeevaart, 2005). These studies provide evidence that overexpression of GA2ox6 could promote conversion of $GA_{53}$ to $GA_{97}$ and consequently reduced synthesis of bioactive $GA_1$ from $GA_{53}$ in vivo.

Mutations in Domain III Affect the Activity of GA2ox5 and GA2ox6

The class C20 GA2oxs, including the *Arabidopsis* GA2ox7 and GA2ox8 and spinach GA2ox3, contain three unique conserved domains that are absent in other GA2oxs (Lee and Zeevaart, 2005). These conserved domains are also present in the rice GA2ox5, GA2ox6 and GA2ox9 (FIG. 11). It has been demonstrated that rice GA2ox6 is capable of catalyzing 2β-hydroxylation of $C_{20}$-GAs (Table 7). Such C20 GA2ox activity can also be demonstrated for GA2ox5 and GA2ox9 using similar methods. The function of none of these three conserved domains in plants had been previously identified. It was discovered in the present invention that the rice GA2ox5Δ335-341$_{ACT}$ mutant, which expresses a mutant GA2ox5 with 4 amino acids deleted in domain III, exhibited severe mutant phenotype. This observation prompted investigation of the function of domain III in GA2oxs.

Truncated cDNAs of GA2ox5 and GA2ox6, with deletion of nucleotides encoding domain III, were fused downstream of the Ubi promoter. The resulting constructs, Ubi::GA2ox5-IIIΔ325-341 and Ubi:: GA2ox6-IIIΔ338-358 (FIG. 10A), were then used for rice transformation. More than 30 independent transgenic plants, with transgene insertions being confirmed, were obtained for each construct.

As shown in FIG. 10B, these transgenic plants exhibited the same normal phenotype as the control transformed with the empty vector (compare panels 2 and 5 with panel 3), which was in contrast to the dwarf phenotype of rice plants transformed with Ubi::GA2ox5 and Ubi::GA2ox6 (panels 1 and 4). Plant height, panicle number and seed germination were normal in all transgenic plants overexpressing GA2oxs with domain III deleted. These studies demonstrated that domain III is important for the activity of GA2ox5 and GA2ox6, and that mutations in domain III affect the activity of GA2ox5 and GA2ox6.

GA Deficiency Promotes Expression of OSH1 and TB1

The studies demonstrated that tiller and adventitious root growth was promoted by GA-deficiency and inhibited by $GA_3$ (see FIGS. 15A and B). Additionally, the inhibition of tillering by $GA_3$ was independent of rice growth stage (see FIG. 15B). To demonstrate that the increase in tiller and adventitious root growth was due to a decrease in endogenous GA levels by overexpression of GA2ox, wild type and GA2ox6$_{ACT}$ seedlings were grown in media with or without 5 μM GA3 after germination. The first tiller of the mutant without GA treatment developed at 9 DAI while that of the GA-treated mutant developed at 16 DAI, indicating that GA3 delayed tillering (FIG. 15A). Root system in the GA-treated mutant was also significantly reduced compared to the mutant without GA treatment, suggesting that GA3 repressed adventitious root development. To further demonstrate that GA inhibits tillering is independent of growth stage, 1-month-old wild type and GA2ox6$_{ACT}$ plants grown in pot soil were sprayed with 10 μM GA3 or water only once every 7 days for a total of 3 sprays. Both GA-treated GA2ox6$_{ACT}$ mutant and wild-type plants produced 2-3 times fewer tillers than mutant and wild-type plants without GA treatment (FIG. 15B).

Figure 14:
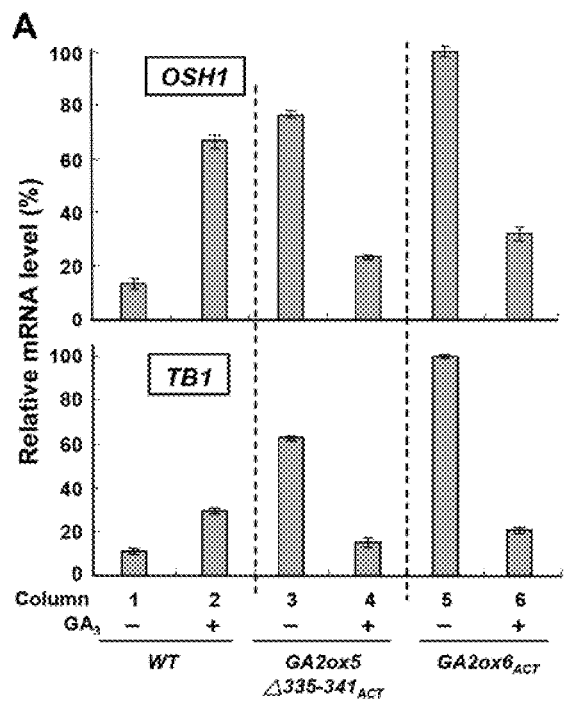
FIG. 14A and FIG. 14B illustrate that $GA_3$ suppresses OSH1 and TB1 expression.
Figure 14:
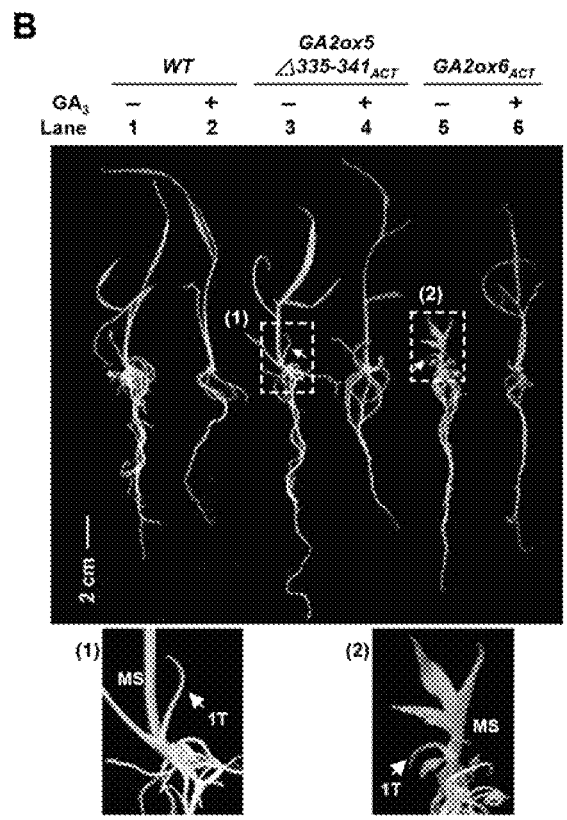

To determine whether GA deficiency induced expression of OSH1 and TB1 that in turn promotes tillering and root development, GA2ox5Δ335-341$_{ACT}$, GA2ox6$_{ACT}$ and wild type seedlings were grown in media with or without 5 μM $GA_3$ after germination. Rice embryos containing tiller buds were collected at 12 DAI. RT-PCR and real-time quantitative RT-PCR analyses revealed that levels of both OSH1 and TB1 mRNAs were significantly higher in mutants than in the wild type, whereas $GA_3$ significantly reduced levels of both mRNAs in mutants (FIG. 14A). Increase in OSH1 and TB1 mRNA levels correlated well with early tillering and adventitious root development in both mutants, whereas $GA_3$ coordinately suppressed OSH1 and TB1 mRNA accumulation, and tillering and adventitious root development in both mutants (compare FIG. 14A with 14B). It is not clear why the accumulation of OSH1 and TB1 mRNAs in the wild type was enhanced by $GA_3$ (FIG. 14A), nevertheless, its stem became slenderer and adventitious root growth was inhibited similar as mutants (FIG. 14B).

Discussion

The GA2ox Family is Differentially Regulated and Plays Pleiotropic Roles Regulating Rice Growth and Development In the present study, gene expression profiling and mutant and transgenic analyses demonstrate that rice GA2oxs control GA levels and regulate rice growth and development, including stem elongation, flower development and seed germination. It was found that differential expression of different members of the rice GA2ox family may control different aspects of rice growth and development. For example, down-regulation of the group A, but not group B, GA2oxs correlated with the phase transition from vegetative to reproductive growth (FIG. 1). This is consistent with the role of GA in promoting flowering in maize and *Arabidopsis* (Evans and Poethig, 1995; Blazquez et al., 1998). Also, although the mRNAs of most GA2oxs accumulated to high levels during seed germination, the mRNA of GA2ox6 decreased significantly and this decrease correlated with rapid seed germination (FIG. 2). Furthermore, similarities as well as differences between monocots and dicots in GA control of some important traits were found, some of which is discussed below.

GA2oxs Control Tiller Growth

The tiller in rice is an important agronomic trait for grain yield. The rice tiller is a specialized grain-bearing branch that normally arises from the axil of each leaf and grows independently of the mother stem (culm) with its own adventitious roots. A MONOCULM 1 gene (MOC1), which encodes a GRAS family nuclear protein and is expressed mainly in the axillary buds, has been shown to be essential for controlling tiller bud growth (Li et al., 2003). It was found some similarities between GA2oxs and MOC1 in controlling rice growth. First, expression of group A GA2oxs correlated with tiller growth in the vegetative phase, and expression of group B GA2oxs correlated with tiller growth in the reproductive phase (FIG. 2C). More importantly, higher tiller number and earlier tiller growth were observed in the GA2ox mutant and Ubi::GA2ox transgenic rice (FIG. 8) and in MOC1::MOC1 transgenic rice (Li et al., 2003). Second, plants became dwarf in the GA2ox mutant and Ubi::GA2ox transgenic rice (FIG. 4 and FIG. 6) and in MOC1::MOC1 transgenic rice (Li et al., 2003). Third, shoot but not root growth was affected in the GA2ox mutant and Ubi:: GA2ox transgenic rice (FIG. 7B) and in the moc1 mutant (Li et al., 2003). Fourth, seed germination was impaired in the GA2ox mutant and Ubi::GA2ox transgenic rice (FIG. 5C) and in the mod mutant (Wang and Li, 2005). These studies suggest that both GA2ox and MOC1 promote tiller growth but inhibit stem elongation and seed germination in rice. It is unclear whether there is crosstalk between the GA and MOC1 signaling pathways or whether they act independently.

One class of dwarf mutants, called tillering dwarf mutants, shows increased tiller number and reduced plant height (Ishikawa et al., 2005). A more recent study also showed that overexpression of YAB1 gene, a feedback regulator of GA biosynthesis, in transgenic rice leads to reduced GA level, increased tiller number and a semi-dwarf phenotype (Dai et al., 2007). Consequently, based on those previous studies and this work, it was concluded that GA deficiency concomitantly suppress shoot elongation and promotes tillering, though the mechanism is unclear. Increased tiller growth indicates loss of apical dominance, which is well known to be mediated by a network of hormonal signals: apically-produced auxin inhibits axillary meristems while cytokinin promotes meristem growth. Whether the auxin, cytokinin and GA signaling pathways crosstalk in rice mutants overexpressing GA2oxs merits further study.

GA2oxs Expressed with Different Promoter and/or Biological Activity Differentially Affect Phenotype The level of bioactive GAs are tightly regulated by a dynamic balance between their synthesis and catabolism, and therefore, expression of enzymes involved in these processes affects the degree of GA-defective phenotypes. In the present study, it was observed that overexpression of individual GA2oxs caused various GA-defective phenotypes in rice. For example, both the T-DNA activation-tagged rice mutant $GA2ox3_{ACT}$ and CaMV35S::GA2ox3 exhibited severe dwarfism and bore no seeds despite long cultivation periods (FIG. 4A and Sakai et al., 2003). Similarly, the T-DNA activation-tagged rice mutant $GA2ox6_{ACT}$ and Ubi::GA2ox5 and Ubi::GA2ox6 transgenic rice exhibited severe dwarfism and produced fewer seeds after more than 5 months of cultivation (Table 4), and germination of $GA2ox6_{ACT}$ mutant seeds was delayed significantly (FIG. 5C). In contrast, the T-DNA activation-tagged rice mutant $GA2ox9_{ACT}$ exhibited semi-dwarf phenotype but produced nearly normal amount of seeds (Table 5) with normal germination rate (FIG. 5C). GA2oxs with different biological activity might account for the difference in phenotypes. Alternatively, activation efficiency by enhancers in T-DNA inserted close to these GA2ox promoters or a positional effect of T-DNA insertion might contribute to the difference. Dose effects of gene overexpression, as detected by mRNA accumulation of tagged genes and severity of phenotypes, appeared to be common for all mutant lines.

Although ectopic overexpression of both GA2ox5 and GA2ox6 caused severe dwarfism in transgenic rice, overexpression of GA2ox5 had more severe growth effects than GA2ox6 in transgenic rice (on fertility and grain weight) and tobacco (on root and hypocotyl length, plant height and seed yield) (FIG. 6), indicating conservation of activity of these two enzymes in monocots and dicots. Similar phenomena were also observed in transgenic *Arabidopsis* and tobacco overexpressing the *Arabidopsis* GA2ox7 and GA2ox8 genes under the control of the CaMV35S promoter; GA2ox7 overexpression generally caused a more severely dwarf phenotype than GA2ox8 overexpression did (Schomburg et al., 2003). However, shortage of GA appeared to affect root growth in docots (FIGS. 6C and 6D; Lee and Zeevaart, 2005). One additional difference is that reduced GA levels promoted tillering of transgenic rice but had no effect on branching of transgenic tobacco (FIG. 6).

GA2oxs Containing a Unique Functional Domain Display Substrate Specificity

GA2ox5, GA2ox6 and GA2ox9 contain three conserved domains that are similar to those of the *Arabidopsis* GA2ox7 and GA2ox8 and spinach GA2ox3 (Lee and Zeevaart, 2005), but are absent in other rice GA2oxs. These *Arabidopsis* and spinach GA2oxs have been shown to catalyze 2β-hydroxylation of $C_{20}$-GAs, such as $GA_{53}$ and $GA_{12}$, instead of $C_{19}$-GA catalysis by most other GA2oxs. In the present study, we found that GA2ox6 also catalyzed 2β-hydroxylation of $C_{20}$-GAs (Table 7), which suggests that the class C20 GA2oxs may have distinct substrate specificity from the class C19 GA2oxs in rice. Domain III appears to be important for activity of class C20 GA2oxs. Transgenic rice overexpressing intact GA2ox5 and GA2ox6 showed severe dwarfism (FIG. 6).

In contrast, the rice GA2ox5Δ335-341$_{ACT}$ mutant overexpressing a truncated GA2ox5 missing 4 amino acids of domain III, showed semi-dwarfism (FIG. 4B) on an otherwise nearly normal phenotype (Table 5), and transgenic rice overexpressing GA2ox5-IIIΔ325-341 and GA2ox6-IIIΔ338-358, with deletion of the entire domain III, showed normal phenotype (FIG. 10B). These data indicate that GA2ox5 activity was only partially lost by partial deletion or mutation, e.g., by deleting 4 amino acids, of domain III, while it was completely lost by deleting the entire domain III. It is unclear whether domain III is essential for substrate binding or for catalytic activity. Interestingly, the GA2ox5Δ335-341$_{ACT}$ mutant produced twice as many tillers, and its roots were 2.5 times longer than the wild type (Table 5), indicating that the partially-functional GA2ox5 promoted root and tiller meristem growth.

T-DNA Activation-Tagged Rice Mutants are Useful for Studying Functions of GA2oxs More than 18 GA-deficient mutants have been identified by screening rice mutant populations that were generated by chemical mutagen, retrotransposon (Tos17) insertion, and γ-ray irradiation (Sakamoto et al., 2004). Despite extensive efforts, loss-of-function mutations in GA2ox that caused elongated slender phenotype were not found in these mutant populations, probably due to functional redundancy of the GA2ox multigene family; however, gain-of-function mutations in a GA2ox that caused dwarf phenotype were not found in these mutant populations either, perhaps due to a lack of tools for gene activation in the three mutagenesis approaches used (Sakamoto et al., 2004). In the present study, severely dwarf rice mutants GA2ox3$_{ACT}$ and GA2ox6$_{ACT}$ were identified by forward genetics screens, and semi-dwarf mutants GA2ox5Δ335-341$_{ACT}$ and GA2ox9$_{ACT}$ were identified by reverse genetics screens, of the TRIM mutant library (Hsing et al., 2007). Further study of the GA2ox5$_{ACT}$Δ335-341 mutant led to the discovery of an important functional domain, domain III, in GA2oxs. All these mutants displayed specific phenotypes due to activation of individual GA2oxs. Consequently, the gene activation and/or knockout rice mutant population is a useful resource not only for the identification of mutants with altered GA2ox functions but also for the study of the functions of other genes involved in GA biosynthesis and signaling pathways in rice.

An additional advantage of the T-DNA activation approach is that it allows the overexpression of GA2oxs under the control of their native promoters. The T-DNA activation approach has been shown to mainly elevate the expression level of nearby genes without altering the original expression pattern in general (Jeong et al., 2002). The controlled expression of GA2oxs in the right time and right place may give rise to phenotypes that facilitate functional analysis of both GA2ox promoters and enzymes during all phases of the life cycle of rice.

GA Signaling Represses OSH1 and TB1 Expression that in Turn Inhibits Tillering

Despite the important contribution of tillering and root system to grain yield, the mechanisms that control these two developmental processes in rice are mostly unclear. It is interesting to note that high tillering often accompanies dwarfism in rice (Ishikawa et al., 2005). A recent study shows that overexpression of a YAB1 gene, a feedback regulator of GA biosynthesis, in transgenic rice leads to reduced GA level, increased tiller number and a semidwarf phenotype (Dai et al., 2007), which provides a clue that GA might coordinately control the two opposite developmental processes.

Figure 13:
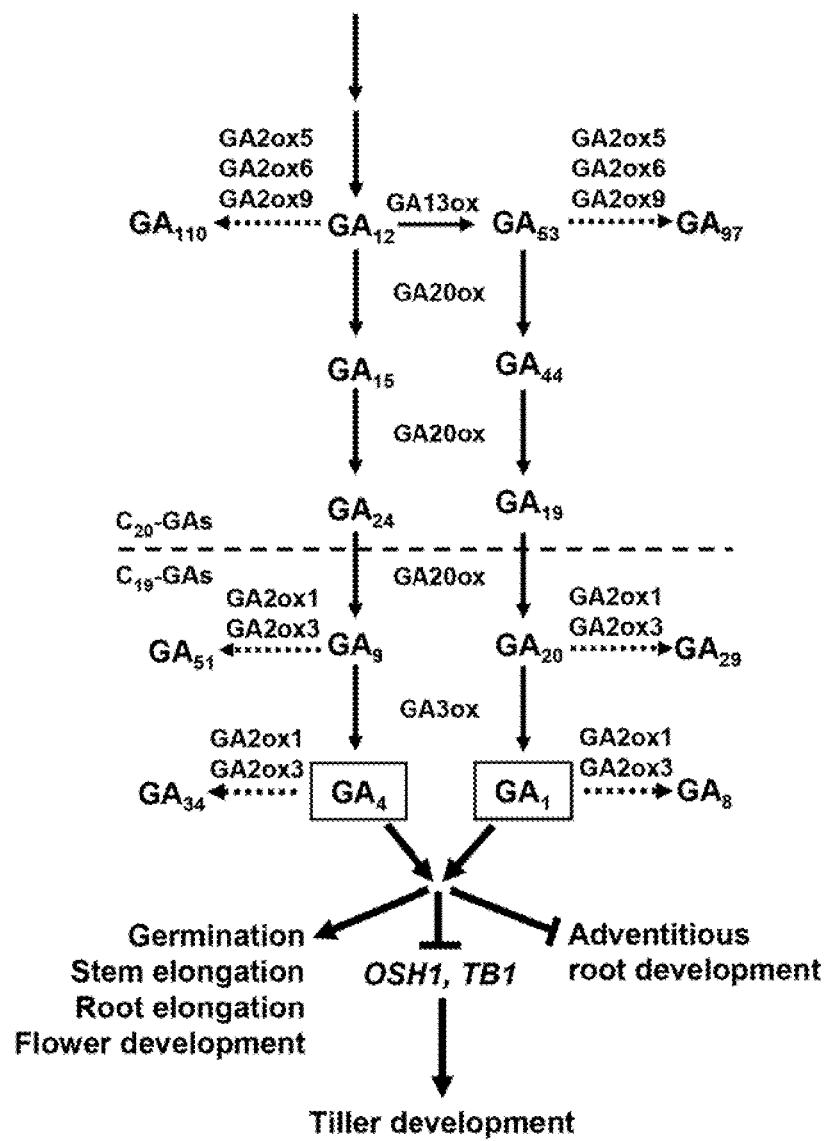
FIG. 13 is schematic diagram that shows GA catabolism and response pathways: bioactive GA positively regulates germination, stem and root elongation, and flower development, but negatively regulates OSH1 and TB1 that control tillering; bioactive GA also negatively regulates adventitious root development.

In the present study, by using GA-deficient mutants, we demonstrated that stem elongation was inhibited but tillering was promoted by GA-deficiency; in contrast, stem elongation was promoted but tillering was inhibited by GA$_3$ (FIG. 14B). Consequently, we conclude that GA concomitantly promotes shoot elongation and inhibits tillering (FIG. 13). However, increase in tillering indicates a loss of apical dominance. Studies mostly with dicots indicate that this process is mediated by a network of hormonal signals: apically-produced auxin inhibits axillary meristems, while cytokinin promotes meristem growth (Busov et al., 2008). A HIGH-TILLERING DWARF 1 (HTD1) gene, encoding a carotenoid cleavage dioxygenase, negatively regulates tiller bud outgrowth in rice (Zou et al., 2006). As HTD1 expression is induced by auxin (NAA), it has been suggested that auxin may suppress rice tillering partly through up-regulation of HTD1 transcription (Zou et al., 2006). Further studies are required to understand whether auxin, cytokinin and GA signalings interact and control tillering in rice.

Figure 10:
FIGS. 10A and 10B illustrate that mutations in domain III affected the activity of GA2ox5 and GA2ox6.
Figure 10:
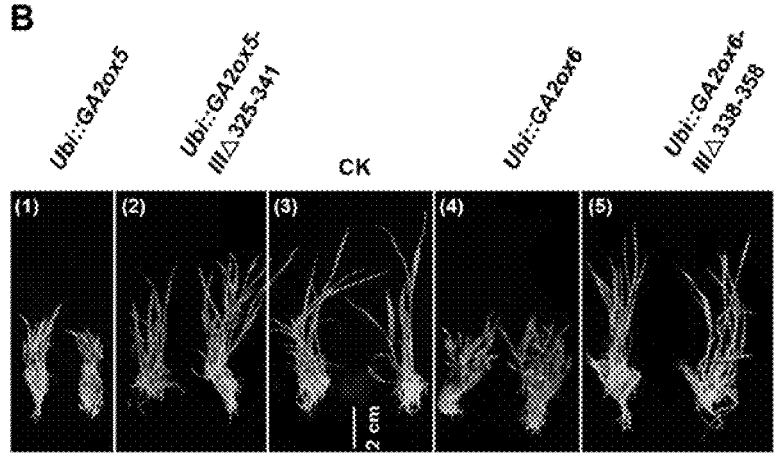

In the present study, we also showed that growth of adventitious roots was induced by GA-deficiency and suppressed by GA$_3$ (FIG. 10). This notion is supported by a recent study which shows that GA$_3$ inhibits adventitious root formation in *Populus* tree (Busov et al., 2006). Additionally, overexpression of DELLA-less versions of GA insensitive (GA1) and repressor of GAI-like 1 (RGL1), which conferred GA insensitivity in transgenic *Populus* trees, led to dwarfism and increase in adventitious root growth (Busov et al., 2006). Crown rootless (Crl1) promotes crown and lateral root formation and Crl1 itself is up regulated by auxin in rice (Inukai et al., 2005). However, aboveground organs are normal in the crl1 mutant (Inukai et al., 2005), indicating that adventitious/crown root growth might be regulated by a root-specific auxin signaling pathway. Again, further studies are required to determine whether auxin and GA signaling interacti on controls root growth in rice.

MOC1 is an essential regulator of rice tiller bud formation and development (Li et al., 2003). Overexpression of MOC1 also promotes tiller growth and inhibits stem elongation in transgenic rice, and OSH1 and TB1 are downstream positive regulators themselves positively regulated by MOC1 in tiller development (Li et al., 2003; Wang and Li, 2005). In addition to tillering, seed germination and fertilization are also impaired in the moc1 mutant, which indicates that MOC1 might be involved in GA signaling pathways, by serving as both positive and negative regulators (Wang and Li, 2005). However, it is unclear how MOC1 interacts with the GA signaling pathway for regulation of OSH1 and TB1 expression and thus tiller development.

We were unable to detect MOC1 mRNA in GA2ox6$_{ACT}$ mutant and wild type seedlings by the RT-PCR method in a quantitative manner, probably due to its low abundance in the axillary buds (Li et al., 2003). Nevertheless, we showed that expression of OSH1 and TB1 was induced by GA-deficiency and suppressed by GA$_3$ (FIG. 14A). Meanwhile, development of tiller and adventitious roots was promoted by GA-deficiency and inhibited by GA$_3$ (FIG. 14B). Consequently, our study provides evidence that GA negatively regulates OSH1 and TB1 expression that in turn inhibits tiller development (FIG. 13).

GA2ox Mutants are Useful in Plant Breeding

Semi-dwarfism is one of the most valuable traits in crop breeding, because it results in plants that are more resistant to damage by wind and rain (lodging resistant) and have stable yield increases. It is a major component in the increasing yield of the "green revolution" varieties (Peng et al., 1999; Spielmeyer et al., 2002). However, the creation of such varieties has relied on limited natural genetic variations within the crop species. Overexpression of GA2oxs is an easy way to reduce GA levels in transgenic plants, but constitutive ectopic overexpression of most GA2oxs caused severe dwarfism and low seed production in various plant species because active GAs were probably deactivated as soon as they were produced (Schomburg et al., 2003; Lee and Zeevaart, 2005; Dijkstra et al., 2007; Sakamoto et al., 2001; Singh et al., 2002; Biemelt et al., 2004). Expression of the rice GA2ox1 under the control of the rice GA3ox2 promoter, at the site of active GA biosynthesis in shoot apex, led to a semi-dwarf phenotype with normal flowering and grain development (Sakamoto et al., 2003). The present invention offers three alternative approaches for breeding plants with reduced height but normal flowering, leaf mass, seed production, and other desirable traits. First, overexpression of GA2ox9 generated a semi-dwarf rice variety. The average grain weight and fertility of the GA2ox9$_{ACT}$ mutant were only slightly reduced (by 8 and 4%, respectively), but tiller number increased 22% compared to the wild type (Table 5), which suggests a potential yield increase. Second, overexpression of GA2oxs with defective domain III could also generate a semi-dwarf rice variety. The average grain weight and fertility of the GA2ox5Δ335-341$_{ACT}$ mutant was reduced by 16 and 12%, respectively, but tiller number increased almost 2-fold (Table 5), which also suggests a potential for overall yield increase. Third, overexpression of a selected GA2ox gene, such as GA2ox6 which has less effect on plant growth, could be used for breeding a semi-dwarf plant without sacrificing seed production. It is interesting to note that roots of both GA2ox5Δ335-341$_{ACT}$ and GA2ox9$_{ACT}$ were 2-3-fold longer than the wild type (Table 5), a trait that could be beneficial for increased uptake of nutrients and water from soil.

Figure 15:
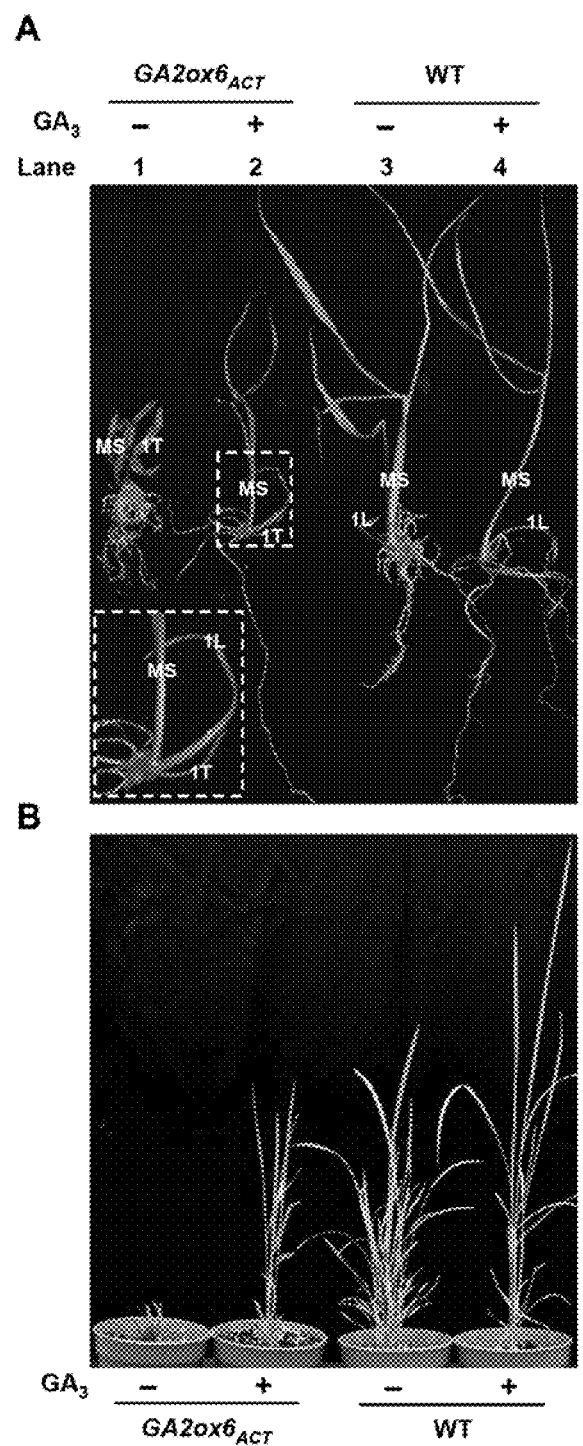
FIG. 15A and FIG. 15B show that $GA_3$ represses tiller growth independent of growth stages.
Figure 16:
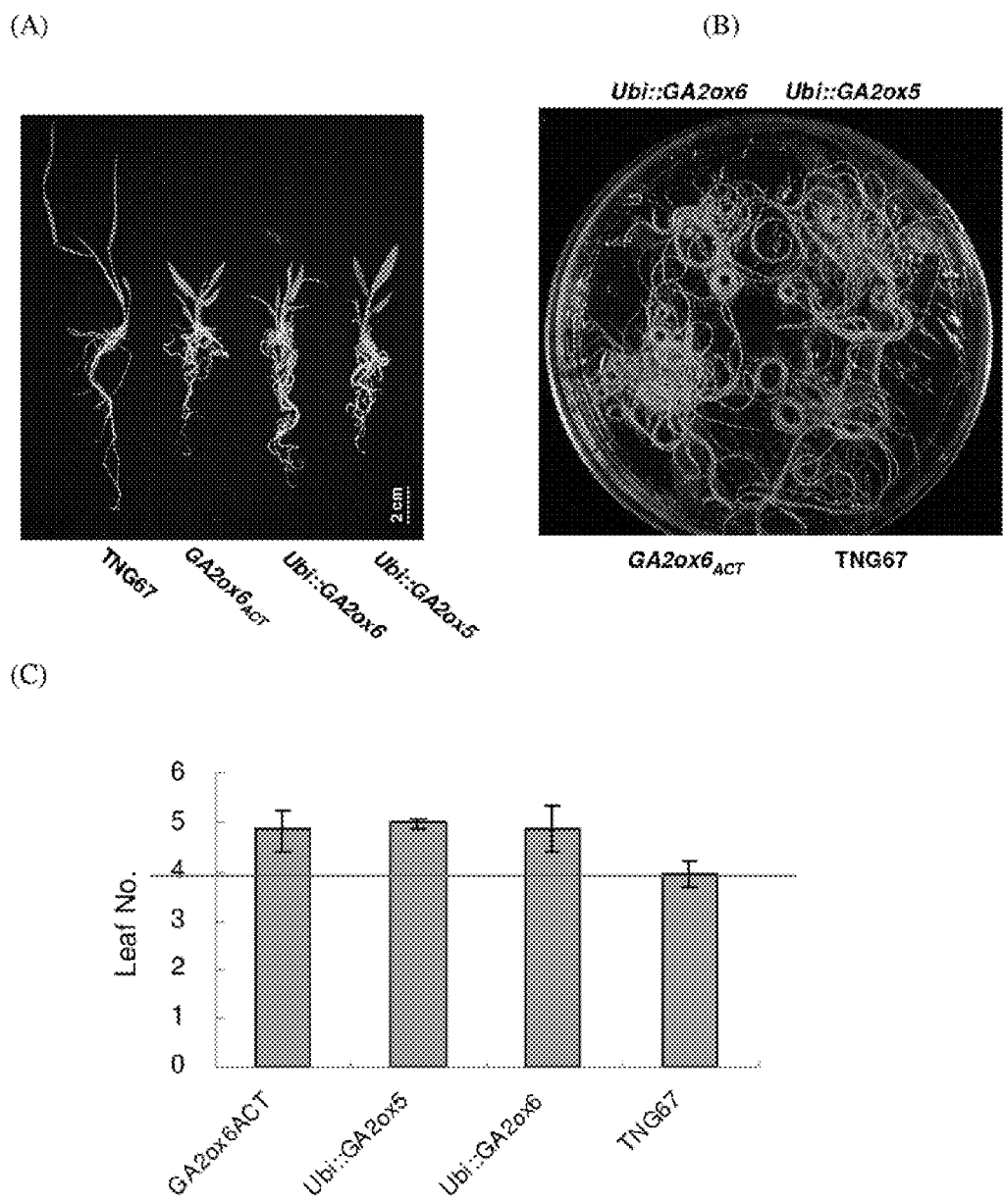
FIGS. 16 A-C illustrate that GA deficiency enhanced the strength of stem and root and increased the number of leaves at seedling stages.

Gibberellins (GAs) are a class of essential plant hormones that control a variety of plant growth and developmental processes. Gibberellin 2-oxidases (GA2oxs) down-regulate the endogenous levels of bioactive GAs in plants through 2β-hydroxylation of biologically active GA. Identities of conserved domain of deduced amino acids were low among the 10 putative GA2oxs in rice, indicating that these GA2oxs may play variable roles (Table 1). We also found that mutants or transgenic rice overexpressing GA2oxs, under the control of their native or a constitutive promoter, exhibited a broad range mutant phenotypes, depending on promoters and GA2ox genes. In addition to some previously discussed effects caused by overexpression of GA2oxs, such as reduced plant height, small dark green leaves, delayed seed germination, delayed flowering, and reduced seed production, we further discovered thicker and stronger stems, normal-size dark green leaves, early and increased tillering, more active adventitious, stronger root growth and altered root architecture (FIG. 16), and enhanced stress tolerance, due to the reduced accumulation of bioactive GA. Our experiment also demonstrated that GA content in plants is closely related to the thickness of stem (FIG. 15). These studies suggest the pleiotropic role of GA2oxs in controlling rice growth and architecture. We also found that overexpression of GA2oxs in transgenic dicotyledons plants, such as tobacco, exhibited various levels of semidwarfism and increases in the number of leaves (Table 5 and FIG. 6). Our studies demonstrated that GA2oxs can be applied to breeding of various plant species for alteration of statures.

Figure 17:
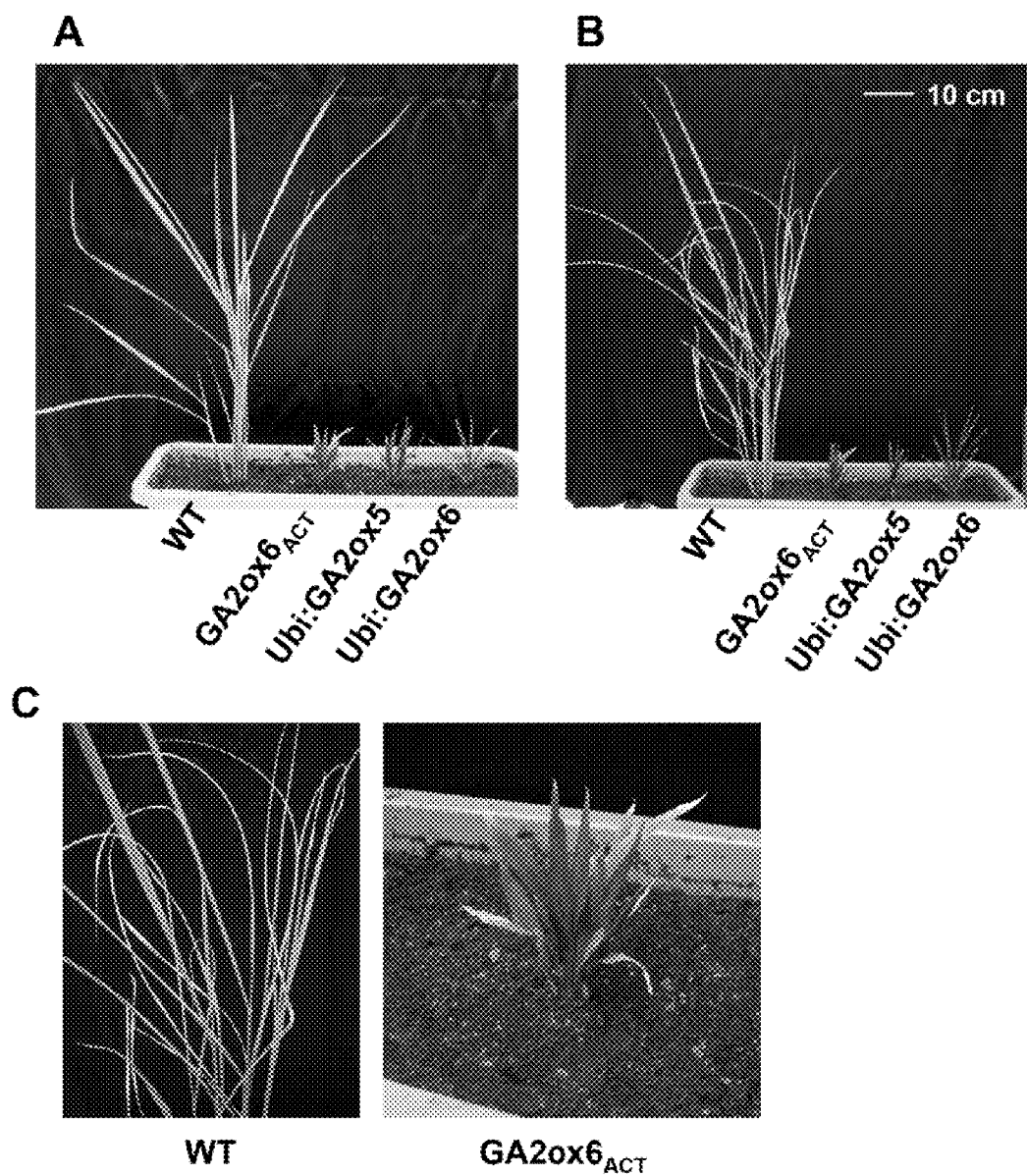
FIGS. 17A-C illustrate that GA deficiency enhanced the drought tolerance.

Semidwarfism, higher tillering, more biomass, more adventitious roots, stronger and thicker stems, stable increase of yields and/or seed production, enhanced stress tolerance (FIG. 17), etc., are the most valuable traits in crop breeding, because it results in plants that are more resistant to damages caused by wind and rain (lodging resistant) and biotic and abiotic stresses, and have stable increase of yields. However, the creation of such varieties has relied on natural genetic variations within the crops species that are difficult to achieve in conventional breeding. Overexpression of GA2oxs is an easy way to control GA levels in transgenic plants. Our discoveries offer approaches for breeding plants with desirable traits that have not been described previously, in addition to other known traits. That is, overexpression of GA2ox gene in both monocots and dicots resulted in plants with thicker stems, branches, more leaf numbers, and higher stress tolerance.

In view of the present disclosure, native, inducible or constitutive promoters can be used for better ectopic overexpression of GA2oxs in transgenic rice to lead to desirable traits, such as reduced height, higher tillering, more biomass, increased root mass, stronger stems, enhanced stress tolerance, higher grain yield, etc. in transgenic rice. The desirable traits can be obtained in a wide range of plant species by controlling expression of GA2oxs or a related gene product.

Materials and Methods

Plant Materials

The rice cultivar *Oryza sativa* L. cv Tainung 67 was used as in this study. Four T-DNA tagged rice GA2ox mutant lines were obtained from the Taiwan Rice Insertional Mutagenesis database (TRIM database, http://trim.sinica.edu.tw/). T$_1$ mutant seeds were surface sterilized in 2.5% NaClO for 18 minutes, washed well with sterile water, placed on MS agar medium (Murashige and Skoog Basal Medium, Sigma), and incubated at 28° C. with continuous light for 15~20 days. Wild type rice was grown under the same conditions. Plants were transplanted to pot soil and grown in a net-house during the growing season.

Database Searching and Bioinformatics Analysis of GA2Oxs

Putative GA2ox genes were searched by blast with the database (www.ncbi.nlm.nih.gov/BLAST/) using the published rice GA2ox1 to GA2ox4 and 20G-Fe (II) oxygenase conserved domain, and by annotation of two rice databases, The Institute for Genomic Research (TIGR) (www.tigr.org/tdb/e2k1/osa1/irgsp.shtml) and the Rice Genome Annotation (RiceGAAS) (http://ricegaas.dna.affrc.go.jp). Non-redundant amino acid sequences of putative GA2oxs were analyzed for conserved domains with the program Vector NTI (version 9.0.0). The deduced amino acid sequences were aligned and the phylogenetic tree was obtained with Vector NTI using the Neighbor Joining (NJ) method (Saitou and Nei, 1987). The Knowledge-based *Oryza* Molecular Biological Encyclopedia (KOME) database (http://cdna01.dna.affrc.go.jp/cDNA) was used to search cDNA.

T-DNA Flanking Sequence Analysis

Genomic DNA was extracted with CTAB extraction buffer as described elsewhere (Doyle and Doyle, 1987). T-DNA flanking sequences were rescued using a built-in plasmid rescue system (Upadhyaya et al., 2002) and analyzed with an ABI Prism 3100 DNA sequencer (Applied Biosystems) using DNA sequences 100-bp upstream of the T-DNA right border as an RB primer. T-DNA flanking sequences were blasted by a BLASTN (Basic Local Alignment Search Tool) routine against the NCBI database for assignment in the rice BAC/PAC site, and gene dispersions were annotated by the RiceGAAS database.

PCR and RT-PCR

Total RNA was purified from rice tissues using a Trizol reagent (Invitrogen). Total RNA (15 µg aliquots) was treated with 1 unit of RNase-free DNase I (Promega) in a 20 µL volume and incubated at 37° C. for 30 min. The RNA sample was then incubated at 65° C. for 10 min and placed on ice. cDNA synthesis was performed in a 20 µL mixture containing 1× reverse transcription reaction buffer (Invitrogen), 4.5 µg of purified RNA, 400 ng oligo $(dT)_{16}$ primer, 5 mM DTT, 0.5 mM each dNTP, 40 units RNasin (Promega), and 200 units Superscript® III reverse transcriptase (Invitrogen). The reaction was carried out at room temperature (25° C.) for 10 min, transferred to 50° C. for 1 h, and terminated by heating at 72° C. for 15 min. The sample, which served as a cDNA stock for PCR analysis, was then stored at −70° C.

RT-PCR analysis was carried out in a 15 µl, solution containing 0.9 µL cDNA, 1×PCR buffer (Promega), 1.5 mM $MgCl_2$, 0.2 mM each dNTP, 0.3 µmole each primer, 3% DMSO, and 0.6 units of Taq DNA polymerase (Promega). For GA2ox2, GA2ox7, and GA2ox8 that had very low mRNA abundance, RT-PCR analysis was carried out using KOD Hot Start DNA Polymerase (Novagen). Each 15 µL of reaction solution contained 0.9 µL cDNA, 1×PCR buffer (Novagen), 1.0 mM $MgSO_4$, 0.2 mM each dNTP, 0.3 µmole each primer, 3% DMSO, and 1 unit of KOD Hot Start DNA Polymerase (Novagen). PCR was performed with the following conditions: denaturation at 94° C. for 1 min, primer annealing at different temperature for each gene for 1 min, primer extension at 72° C. for 1 min, and a final 10 min primer extension at 72° C. using a programmable thermal cycler (PTC-200, MJ Research). The RT-PCR products were fractionated in a 1.5% agarose gel and visualized by ethidium bromide staining.

Rice and Tobacco Transformation

Full length GA2ox5 and GA2ox6 cDNAs were PCR-amplified from the rice genomic DNA based on their putative open reading frames annotated with the RiceGAAS database. A BamHI restriction site was designed at the 5' end of DNA primers used for PCR amplification (Supplemental Table SIV). The PCR products of 1,043 and 1,094 bps were ligated into the pGEM®-T Easy cloning vector (Promega) and their sequences were confirmed by DNA sequencing. Plasmid pAHC18 (Bruce et al., 1989) was derived from plasmid pUC18 that contains the maize ubiquitin (Ubi) promoter and nopaline synthase (Nos) terminator. GA2ox5 and GA2ox6 cDNAs were then excised with BamHI from the pGEM-T Easy vector and ligated into the same site between the Ubi promoter and Nos terminator in plasmid pLN. Plasmids containing Ubi:: GA2ox5 and Ubi: GA2ox6 were linearized with HindIII and inserted into the same site in pCAMBIA1301 (Hajdukiewicz et al., 1994). The resulting binary vectors were transferred into *Agrobacterium tumefaciens* strain EHA105 and then used for rice and tobacco transformation using methods previously described (Krügel, et al., 2002).

The constructs GA2ox5-IIIΔ325-341 and GA2ox6-IIIΔ338-358, which generated GA2ox5 and GA2ox6 with deletions of domain III (amino acids 325 to 341 and 338 to 358, respectively), were PCR-amplified with DNA primers shown in Supplemental Table SIV. PCR products of 992 and 1,031 bps were ligated into the pGEM®-T Easy cloning vector and then the pCAMBIA1301 binary vector, following procedures described above, for generation of binary vectors containing Ubi:: GA2ox5-IIIΔ325-341 and Ubi:: GA2ox6-III Δ338-358 for rice transformation.

Expression and Activity Assay of Recombinant GA2ox5 and GA2ox6

Full length cDNAs of GA2ox5 and GA2ox6 in the pGEM®-T Easy cloning vector were digested with BamHI and subcloned into the same site in pGEX-5X expression vector (Amersham Biosciences). The resulting expression vectors were used to transform *E. coli* strain BL21-Codon-Plus® (DE3) RIPL (Stratagen). A volume of 5 mL transformants pre-cultured overnight in Luria-Bertani broth (LB broth, DIFCO) was transferred to 500 mL of LB broth with 100 $mgL^{-1}$ ampicillin and incubated at 37° C. until cell density reached an $OD_{600}$ around 0.6~0.8. Isopropyl-β-D-thiogalactopyranoside (IPTG) was added to the bacteria culture to a final concentration of 0.3 mM and incubated at 28° C. for another 3 hours. Bacteria were pelleted by centrifuge and harvested, resuspended in BugBuster® Protein Extraction Reagent (Novagen) at room temperature for 10~20 minutes, and centrifuged at 1,3000 rpm for 30 min. The supernatant protein extracts were partially purified through GST-Bind resin (Novagen), and the purified protein extracts were stored at −80° C. Enzyme assays with recombinant GA2ox5 and GA2ox6 were performed in Dr. Zeevaart's laboratory. The assay methods for product identification were described in Lee and Zeevaart (2002).

Analysis of Endogenous GA Levels

The procedures for extraction, purification, and quantification of endogenous GAs have been described elsewhere (Talon et al., 1990, Zeevaart et al., 1993, Schomburg et al., 2003).

Primers

Primers used for the confirmation of T-DNA insertions in mutant genomes, DNA PCR and RT-PCR analysis are provided in Table 7.

TABLE 7

Primers used for T-DNA flanking sequence, PCR and RT-PCR analyses and plasmid construction.

| Primers | SEQ ID NO | Sequence | Gene |
|---|---|---|---|
| PCR (Confirmation of T-DNA insertion and genotyping) | | | |
| GA2ox5-5' | SEQ ID NO: 31 | 5'-ATGGAGGAGCACGACTACGACT-3' | OsGA2ox5$^Δ$335-341$_{ACT}$genotyping |
| GA2ox5-R2 | SEQ ID NO: 32 | 5' TCCTCCATGATCTGCTTCCTGTA-3' | |
| GA2ox6-5' | SEQ ID NO: 33 | 5'-AGATACTCACTCCGTTTCATGTT-3' | OsGA2ox6$_{ACT}$ genotyping |
| GA2ox6-3' | SEQ ID NO: 34 | 5'-GTAGTGCGGTGAAACAGGATGCC-3' | |
| GA2ox9-5' | SEQ ID NO: 35 | 5'-TGCTCCGGACGCCACAATCTA-3' | OsGA2ox9$_{ACT}$ genotyping |

TABLE 7-continued

Primers used for T-DNA flanking sequence,
PCR and RT-PCR analyses and plasmid construction.

| Primers | SEQ ID NO | Sequence | Gene |
|---|---|---|---|
| GA2ox9-3' | SEQ ID NO: 36 | 5'-CGAGATGATACTTTGACCAACAAT-3' | |
| RB | SEQ ID NO: 37 | 5'-AACTCATGGCGATCTCTTACC-3' | T-DNA right border |
| RT-PCR-analysis of gene expression | | | |
| GA2ox1-F | SEQ ID NO: 38 | 5'-CGAGCAAACGATGTGGAAGGGCTACAGG-3' | OsGAox1 (332 bp) |
| GA2ox1-R | SEQ ID NO: 39 | 5'-TGGCTCAGGCGGAGTGAGTACATTGTCG-3' | |
| GA2ox2-F | SEQ ID NO: 40 | 5'-CCCCACATCCCTGACAAGGCTC-3' | OsGA2ox2 (592 bp) |
| GA2ox2-R | SEQ ID NO: 41 | 5'-CTATTCATGGTCGTCATCGTCC-3' | |
| GA2ox3-F | SEQ ID NO: 42 | 5'-TGAGCGCGCTGGTGACGGCGGA-3' | OsGA2ox3 (451 bp) |
| GA2ox3-R | SEQ ID NO: 43 | 5'-CTTGATTTGTAGGCAGCCTTC-3'- | |
| GA2ox4-F | SEQ ID NO: 44 | 5'-TCGGTGGAGGATAACTTCGGC-3' | OsGA2ox4 (999 bp) |
| GA2ox4-R | SEQ ID NO: 45 | 5'-TGGGTTAGCGACAGGTGGTGG-3' | |
| GA2ox5-F | SEQ ID NO: 46 | 5'-ATGGAGGAGCACGACTACGACT-3' | OsGA2ox5 (974 bp) |
| GA2ox5-R | SEQ ID NO: 47 | 5'-TCCTCCATGATCTGCTTCCTGTA-3' | |
| GA2ox6-F | SEQ ID NO: 48 | 5'-GACGACGTGCTTCCTGCGGCTCAA-3' | OsGA2ox6 (389 bp) |
| GA2ox6-R | SEQ ID NO: 49 | 5'-CTTCCTGCACCTTCTTCCTGTA-3' | |
| GA2ox7-F | SEQ ID NO: 50 | 5'-ACGGGAGCTTCTACGCGAGT-3' | OsGA2ox7 (594 bp) |
| GA2ox7-R | SEQ ID NO: 51 | 5'-TCAAATCTGCAGAGCCTGTCGTC-3' | |
| GA2ox8-F | SEQ ID NO: 52 | 5'-GTGCTGCGGCGGATGGTGGTGG-3' | OsGA2ox8 (555 bp) |
| GA2ox8-R | SEQ ID NO: 53 | 5'-CTTCGTCGCGGCCTCATCGTTGG-3' | |
| GA2ox9-F | SEQ ID NO: 54 | 5'-ATGTCGAGGCTGGCCAGGG-3' | OsGA2ox9 (533 bp) |
| GA2ox9-R | SEQ ID NO: 55 | 5'-CATACGAGGAAATTACTGAGGC-3' | |
| GA2ox10-F | SEQ ID NO: 56 | 5'-CTCCGATCCAACGACACCTCT-3' | OsGA2ox11 (501 bp) |
| GA2ox10-R | SEQ ID NO: 57 | 5'-AGCCAGCGCCTCGTCCTGAT-3' | |
| GA3ox2-F | SEQ ID NO: 58 | 5'-TCTCCAAGCTCATGTGGTCCGAGGGCTA-3' | OsGA3ox2 (346 bp) |
| GA3ox2-R | SEQ ID NO: 59 | 5'-TGGAGCACGAAGGTGAAGAAGCCCGAGT-3' | |
| 18S-F | SEQ ID NO: 60 | 5'-CCTCGTGCCCCTATCAACTT-3' | 18S rRNA (201 bp) |
| 18S-R | SEQ ID NO: 61 | 5'-GACACTAAAGCGCCCGGTAT-3' | |
| RT-PCR-cDNA amplification for cloning | | | |
| GA2ox5-full-F | SEQ ID NO: 62 | 5'-AGCGGATCCATGGAGGAGCACGACTACG-3' | OsGA2ox5 full length |
| GA2ox5-full-R | SEQ ID NO: 63 | 5'-AATGGATCCCTATCGGGTTCGAAAGCGG-3' | (for cloning) |
| GA2ox6-full-F | SEQ ID NO: 64 | 5'-TTGGATCCATGCCGGCCTTCGC-3' | OsGA2ox6 full length |
| GA2ox6-full-R | SEQ ID NO: 65 | 5'-CGGGATCCTTATTGTACTGAAGA-3' | (for cloning) |
| GA2ox5-III-D-R | SEQ ID NO: 66 | 5'-TCGGATCCCTACTCCATGATCTGCTTCCTG-3' | cloning of Ubi::OsGA2ox5-III$^\Delta$325-341 |
| GA2ox6-III-D-R | SEQ ID NO: 67 | 5'-TTTGGATCCTTATTCCTGCACCTTCTTCCT-3' | cloning of Ubi::OsGA2ox6-III$^\Delta$338-358 |

TABLE 7-continued

Primers used for T-DNA flanking sequence,
PCR and RT-PCR analyses and plasmid construction.

| Primers | SEQ ID NO | Sequence | Gene |
|---------|-----------|----------|------|

LITERATURES CITED

Biemelt S, Tschiersch H, Sonnewald U (2004) Impact of altered gibberellin metabolism on biomass accumulation, lignin biosynthesis, and photosynthesis in transgenic tobacco plants. Plant Physiol 135: 254-265.

Blazquez M A, Green R, Nilsson O, Sussman M R, Weigel D (1998) Gibberellins promote flowering of arabidopsis by activating the LEAFY promoter. Plant Cell 10: 791-800.

Bruce, W B, Christensen, A H, Klein, T, Fromm, M, and Quail, P H (1989) Photoregulation of a phytochrome gene promoter from oat transferred into rice by particle bombardment. Proc. Natl. Acad. Sci. USA 86: 9692-9696.

Choi Y H, Kobayashi M, Fujioka S, Matsuno T, Hirosawa T, Sakurai A (1995) Fluctuation of Endogenous Gibberellin Levels in the Early Development of Rice. Biosci. Biotech. Biochem. 59: 285-288.

Dai M, Zhao Y, Ma Q, Hu Y, Hedden P, Zhang Q, Zhou D-X (2007) The rice YABBY1 gene is involved in the feedback regulation of gibberellin metabolism. Plant Physiol. 144: 121-133.

Dijkstra C, Adams E, Bhattacharya A, Page A F, Anthony P, Kourmpetli S, Power J B, Lowe K C, Thomas S G, Hedden P, Phillips A L, Davey M R (2007) Over-expression of a gibberellin 2-oxidase gene from Phaseolus coccineus L. enhances gibberellin inactivation and induces dwarfism in Solanum species. Plant Cell Rep. 27: 463-470.

Doyle J J, Doyle J L (1987) A rapid DNA isolation procedure for small quantities of fresh leaf tissue. Phytoch. Bull. 19:11-15.

Evans M M, Poethig R S (1995) Gibberellins promote vegetative phase change and reproductive maturity in maize. Plant Physiol 108: 475-487.

Graebe J E (1987) Gibberellin biosynthesis and control. Ann. Rev. Plant Physiol. 38: 419-465.

Hajdukiewicz P, Svab Z, Maliga P (1994) The small, versatile pPZP family of Agrobacterium binary vectors for plant transformation. Plant Mol Biol 25: 989-994.

Harberd N P, King K E, Carol P, Cowling R J, Peng J, Richards D E (1998) Gibberellin: inhibitor of an inhibitor of . . . ? Bioessays 20: 1001-1008.

Hedden P, Phillips A L (2000). Gibberellin metabolism: new insights revealed by the genes. Trends in Plant Sci. 5: 523-530.

Hsing Y-I, Chern C-G, Fan M-J, Lu P-C, Chen K-T, Lo S-F, Sun P-K, Ho S-L, Lee K-W, Wang Y-C, Huang W-L, Ko S-S, Chen S, Chen J-L, Chung C-I, Lin Y-C, Hour A-L, Wang Y-W, Chang Y-C, Tsai M-W, Lin Y-S, Chen Y-C, Yen H-M, Li C-P, Wey C-K, Tseng C-S, Lai M-H, Huang S-C, Chen L-J, Yu S-M (2007) A rice gene activation/knockout mutant resource for high throughput functional genomics. Plant Mol. Biol. 63: 351-364.

Ishikawa S, Maekawa M, Ante T, Onishi K, Takamure I, Kyozuka J (2005) Suppression of tiller bud activity in tillering dwarf mutants of rice. Plant Cell Physiol. 46: 79-86.

Jeong D H, An S, Kang H G, Moon S, Han J J, Park S, Lee H S, An K, An G (2002) T-DNA insertional mutagenesis for activation tagging in rice. Plant Physiol 130: 1636-1644.

Kende H, Zeevaart J A D (1997) The five "classical" plant hormones. The Plant Cell 9: 1197-1210.

King R W, Evans L T (2003) Gibberellins and flowering of grasses and cereals: prizing open the lid of the "Florigen" black box. Ann. Rev. Plant Biol. 54: 307-328.

Koornneef M and van der Veen J H (1980) Induction and analysis of gibberellin sensitive mutants in Arabidopsis thaliana (L.) heynh. Theor. Appl. Genet. 58: 257-263.

Krügel, T, Lim, M, Gase, K, Halitschke, R and Baldwin, I T (2002) Agrobacterium-mediated transformation of Nicotiana attenuata, a model ecological expression system. Chemoecology, 12: 177-183.

Lee D J, Zeevaart J A D (2002) Differential regulation of RNA levels of gibberellin dioxygenases by photoperiod in spinach. Plant Physiol. 130: 2085-2094.

Lee D J, Zeevaart J A D (2005) Molecular Cloning of GA 2-oxidase3 from spinach and its ectopic expression in Nicotiana sylvestris. Plant Physiol. 138: 243-254.

Li X, Qian Q, Fu Z, Wang Y, Xiong G, Zeng D, Wang X, Liu X, Teng S, Hiroshi F, Yuan M, Luo D, Han B, Li J (2003) Control of tillering in rice. Nature 422: 618-621.

Martin D N, Proebsting W M, Hedden P (1999) The SLENDER gene of pea encodes a gibberellin 2-oxidase. Plant Physiol 121: 775-781.

Olszewski N, Sun T-P, Gubler F (2002) Gibberellin signaling: biosynthesis, catabolism, and response pathways. The Plant Cell 14: S61-S80.

Peng J, Richards D E, Hartley N M, Murphy G P, Devos K M, Flintham J E, Beales J, Fish L J, Worland A J, Pelica F, Sudhakar D, Christou P, Snape J W, Gale M D, Harberd N P (1999) 'Green revolution' genes encode mutant gibberellin response modulators. Nature 400: 256-261.

del Pozo J C, Lopez-Matas M A, Ramirez-Parra E, Gutierrez C (2005) Hormonal control of the plant cell cycle. Physiol. Plant. 123: 173-183.

Ross, J J, Murfet I C, Reid J B (1997) Gibberellin mutants. Physiol. Plant. 100: 550-560.

Saitou N, Nei M (1987) The neighbor-joining method: a new method for reconstructing phylogenetic trees. Mol Biol Evol 4: 406-425.

Sakai M, Sakamoto T, Saito T, Matsuoka M, Tanaka H, Kobayashi M (2003) Expression of novel rice gibberellin 2-oxidase gene is under homeostatic regulation by biologically active gibberellins. J. Plant Res. 116: 161-164.

Sakamoto T, Kobayashi M, Itoh H, Tagiri A, Kayano T, Tanaka H, Iwahori S, Matsuoka M (2001) Expression of a gibberellin 2-oxidase gene around the shoot apex is related to phase transition in rice. Plant Physiol. 125: 1508-1516.

Sakamoto T, Morinaka Y, Ishiyama K, Kobayashi M, Itoh H, Kayano T, Iwahori S, Matsuoka M, Tanaka H (2003) Genetic manipulation of gibberellin metabolism in transgenic rice. Nat Biotechnol 21: 909-913.

Sakamoto T, Miura K, Itoh H, Tatsumi T, Ueguchi-Tanaka M, Ishiyama K, Kobayashi M, Agrawal G K, Takeda S, Abe K, Miyao A, Hirochika H, Kitano H, Ashikari M, Matsuoka M (2004) An overview of gibberellin metabolism enzyme genes and their related mutants in rice. Plant Physiol. 134: 1642-1653.

Schomburg F M, Bizzell C M, Lee D J, Zeevaart J A D, Amasino R M (2003). Overexpression of a novel class of gibberellin 2-oxidases decreases gibberellin levels and creates dwarf plants. Plant Cell 15: 151-163.

Singh D P, Jermakow A M, Swain S M (2002) Gibberellins are required for seed development and pollen tube growth in *Arabidopsis*. Plant Cell 14: 3133-3147.

Spielmeyer W, Ellis M H, Chandler P M (2002) Semidwarf (sd-1), "green revolution" rice, contains a defective gibberellin 20-oxidase gene. Proc Natl Acad Sci USA 99: 9043-9048.

Sun T-P, Gubler F (2004) Molecular mechanism of gibberellin signaling in plants. Ann. Rev. Plant Biol. 55: 197-223.

Tanimoto E (2005) Regulation of root growth by plant hormones—roles of auxin and gibberellin. Critic. Rev. in Plant Sci. 24: 249-265.

Talon M, Koornneef M, Zeevaart J A D (1990) Endogenous gibberellins in *Arabidopsis thaliana* and possible steps blocked in the biosynthetic pathways of the semidwarf ga4 and ga5 mutants. Proc. Natl. Acad. Sci. USA 87: 7983-7987.

Thomas S G, Philips A L, Hedden P (1999) Molecular cloning and functional expression of gibberellin 2-oxidases, multifunctional enzymes involved in gibberellin deactivation. Proc. Natl. Acad. Sci. USA 96: 4698-4703.

Upadhyaya, N M, Zhou, X R, Zhu, Q H et al. (2002) An iAc/Ds gene and enhancer trapping system for insertional mutagenesis in rice. Funct. Plant Biol. 29: 547-559.

Wang Y, Li J (2005) The plant architecture of rice (*Oryza sativa*). Plant Mol. Biol. 59: 75-84.

Zeevaart J A D, Gage D A, Talon M (1993) Gibberellin $A_1$ is required for stem elongation in spinach. Proc. Natl. Acad. Sci. USA 90: 7401-7405.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

---

We claim:

1. A method of generating a transgenic plant having one or more features selected from the group consisting of reduced height, increased tillering number, more biomass, a stronger and thicker stem, a stronger root system, more leaves, stable increase of yields and/or seed production, and enhanced stress tolerance, than a plant of substantially the same genetic background grown under the same conditions, the method comprising:
   (a) transforming a cell of the plant of substantially the same genetic background with a nucleic acid molecule to obtain a recombinant plant cell;
   (b) generating a transgenic plant from the recombinant plant cell, wherein the transgenic plant recombinantly expresses a polypeptide selected from the group consisting of:
      (1) a polypeptide having an amino acid sequence that is at least about 80% identical to SEQ ID NO:2, wherein the amino acid sequence has a domain that is at least 80% identical to SEQ ID NO:70;
      (2) a polypeptide having an amino acid sequence that is at least about 80% identical to SEQ ID NO:4, wherein the amino acid sequence has a domain that is at least 80% identical to SEQ ID NO:71;
      (3) a polypeptide having an amino acid sequence that is at least about 80% identical to SEQ ID NO:10 or at least about 80% identical to SEQ ID NO:12, wherein the amino acid sequence has a domain that is at least 80% identical to SEQ ID NO:74; and
      (4) a mutant class C20 GA2ox having at least one mutation in domain III of class C20 GA2ox, the mutant C20 GA2ox having a reduced enzymatic activity to hydroxylate a class C20-GA precursor compared with an otherwise identical class C20 GA2ox that does not comprise the at least one mutation, and the domain III comprising the amino acid sequence of SEQ ID NO:17.

2. The method of claim 1, wherein the transgenic plant recombinantly expresses a polypeptide selected from the group consisting of: SEQ ID NO:2, SEQ ID NO:4, SEQ ID NO:10, SEQ ID NO:12, SEQ ID NO:27, SEQ ID NO:28, SEQ ID NO:29, SEQ ID NO:30, SEQ ID NO:68, SEQ ID NO:69, and the mutant class C20 GA2ox, wherein the domain III comprises an amino acid sequence selected from the group consisting of SEQ ID NO:18, SEQ ID NO:19, and SEQ ID NO:20, and the otherwise identical class C20 GA2ox comprises an amino acid sequence selected from the group consisting of: SEQ ID NO:2, SEQ ID NO:4, and SEQ ID NO:10.

3. The method of claim 1, wherein the polypeptide is encoded by a gene located in the genome of the transgenic plant.

4. The method of claim 1, wherein gene expression of the polypeptide in the transgenic plant is controlled by a promoter selected from the group consisting of a native promoter; a constitutive promoter selected from the group consisting of a maize ubiquitin (Ubi) promoter, a rice actin (Act1) promoter, and cauliflower mosaic 35S RNA promoter (CaMV35S) promoter; a tissue-specific promoter selected from the group consisting of a rice glutelin (GluB) promoter, a rubisco small subunit (rbcS) promoter and a maize zean gene promoter; a developmental stage-specific promoter selected from the group consisting of a rice alpha-amylase (αAmy)promoter and a rice glycine rich RNA binding protein (GRRP-A1) promoter; and an inducible promoter inducible by drought, salt, high or low temperatures, hypoxia, anoxia, hydration, pH, chemicals, or hormones.

5. The method of claim 4, wherein the inducible promoter is selected from the group consisting of promoters for the genes of Arabidopsis rd29A, cor15A, kin1, heat-shock factor (HSF), C-repeat-binding factor (CBF1) and dehydration-responsive element binding protein (DREB1A); and promoters for the genes of rice HVA1 (ABA-inducible), alcohol dehydrogenase (Adh), ethanol-inducible, and alpha-amylase (GA-inducible).

6. The method of claim 1, wherein gene expression of the polypeptide in the transgenic plant is controlled by a promoter that controls gene expression in a developing seed during seed germination of the transgenic plant, in an early seedling of the transgenic plant, or in a growing plant of the transgenic plant.

7. The method of claim 1, wherein the transgenic plant is a dicot plant.

8. The method of claim 1, wherein the transgenic plant is a monocot plant.

9. The method of claim 1, wherein the transgenic plant is a rice plant.

10. The method of claim 1, further comprising breeding the transgenic plant with a second plant, wherein the second plant is transgenic or nontransgenic.

11. The method of claim 1, further comprising screening the transgenic plant for the one or more features.

12. A method of improving one or more traits of a plant selected from the group consisting of reduced height, increased tillering number, more biomass, a stronger stem, a stronger root system, more leaves, and enhanced stress tolerance, the method comprising increasing expression of a gibberellin 2-oxidase or a derivative thereof in the plant.

13. The method of claim 12, wherein the expression of the gibberellin 2-oxidase or a derivative thereof are increased by recombinant expression in the plant of a polypeptide selected from the group consisting of:
   (1) a polypeptide having an amino acid sequence that is at least about 80% identical to SEQ ID NO:2, wherein the amino acid sequence has a domain that is at least 80% identical to SEQ ID NO:70;
   (2) a polypeptide having an amino acid sequence that is at least about 80% identical to SEQ ID NO:4, wherein the amino acid sequence has a domain that is at least 80% identical to SEQ ID NO:71;
   (3) a polypeptide having an amino acid sequence that is at least about 80% identical to SEQ ID NO: 10 or at least about 80% identical to SEQ ID NO:12, wherein the amino acid sequence has a domain that is at least 80% identical to SEQ ID NO:74;
   (4) a mutant class C20 GA2ox, the mutant GA2ox having at least one mutation in domain III of class C20 GA2ox, the mutant GA2ox having a reduced enzymatic activity to hydroxylate a class $C_{20}$-GA precursor compared with an otherwise identical class C20 GA2ox that lacks the at least one mutation, and the domain III comprising the amino acid sequence of SEQ ID NO:17.

14. The method of claim 13, wherein the expression of the gibberellin 2-oxidase or a derivative thereof are increased by recombinant expression in the plant of a polypeptide selected from the group consisting of: SEQ ID NO:2, SEQ ID NO:4, SEQ ID NO:10, SEQ ID NO:12, SEQ ID NO:27, SEQ ID NO:28, SEQ ID NO:29, SEQ ID NO:30, SEQ ID NO:68, SEQ ID NO:69, and the mutant class C20 GA2ox, wherein the domain III comprises an amino acid sequence selected from the group consisting of SEQ ID NO:18, SEQ ID NO:19, SEQ ID NO:20, and the otherwise identical class C20 GA2ox comprises an amino acid sequence selected from the group consisting of: SEQ ID NO:2, SEQ ID NO:4, and SEQ ID NO:10.

15. The method of claim 14, wherein gene expression of the polypeptide in the plant is controlled by a promoter selected from the group consisting of a native promoter; a constitutive promoter selected from the group consisting of a maize ubiquitin (Ubi) promoter, a rice actin (Act1) promoter, and cauliflower mosaic 35S RNA promoter (CaMV35S) promoter; a tissue-specific promoter selected from the group consisting of a rice glutelin (GluB) promoter, a rubisco small subunit (rbcS) promoter and a maize zean gene promoter; a developmental stage-specific promoter selected from the group consisting of a rice alpha-amylase (□Amy)promoter and a rice glycine rich RNA binding protein (GRRP-A1) promoter; and an inducible promoter inducible by drought, salt, high or low temperatures, hypoxia, anoxia, hydration, pH, chemicals, or hormones.

16. The method of claim 14, further comprising breeding the plant with a second plant, wherein the second plant is transgenic or nontransgenic.

17. The method of claim 12, wherein the plant is a dicot plant.

18. The method of claim 12, wherein the plant is a monocot plant.

19. The method of claim 12, wherein the stress is a biotic stress resulting from an invasion of the plant by a bacterium, a virus, a fungus, a parasite, a harmful insect, an algae, a nematode or a weed.

20. The method of claim 12, wherein the stress is an abiotic stress resulting from the negative impact of a high wind, a low or high temperature, drought, salinity, flood, a poor edaphic condition, high radiation, compaction, contamination, pollution or rapid rehydration during seed germination.

* * * * *

SEQUENCE LISTING

```
<160> NUMBER OF SEQ ID NOS: 75

<210> SEQ ID NO 1
<211> LENGTH: 1026
<212> TYPE: DNA
<213> ORGANISM: Oryza sativa

<400> SEQUENCE: 1
atggaggagc acgactacga ctccaactcg aacccgccgt tgatgagcac gtacaagcac      60
ctgttcgtgg agcagcaccg cctggacatg gacatgggcg ccatcgacgt cgacgagtgc     120
gagctccctg tgatcgacct cgcggggctc atggaggcgg agcaggtgtg ccgcgcagac     180
atggtgcgtg cggcgtcgga atgggcttc ttccaggtga ccaaccacgg cgtgccgcag     240
gcgctgctgc gcgagctgca cgacgcacag gtggccgtgt tccggcggcc cttccaggag     300
aaggtgaccg agaggctgct cggcttctcg ccggagagct accggtgggg aacgccgacg     360
gccaagtgcc tggagcagct gtcgtggtcg gaggcctatc acatcccaat gacgacgccc     420
aggcccagca cgagcatcag ggccagggcg gtgatcgagg aggtgtcgag ggcgatgtac     480
gagctggcgc agaagctggc agagatcctg atgagagggc tgccgggcgc cggcgagggc     540
gagacgatgg tgacgacgcg ggaggagacg tgcttcctgc ggctgaaccg gtacccaccg     600
tgcgccatgg ccatgggggg cttcgggctg tgcccgcaca cggacagcga cttgctcacc     660
atcgtgcacc agcagcagga caccgtcggc ggcctccagc tgctcaaggg cggcaggtgg     720
gtggccgtga agcccagccc cagcaccctc atcgtcaacg tcggcgacct cctgcaggcg     780
tggagcaacg atgtgtacaa gagcgtggag cacagggtga tggccaacgc cacgctggag     840
cgcttctcca tggccttctt cctctgcccc tcctaccaca cgctcatcat cccaagcagc     900
agccatgtcc acgacgacga tgcccattac cggagcttca ccttcggcga gtacaggaag     960
cagatcatgg aggacgtcag gagcacaggc cgcaagattg gactgcaccg ctttcgaacc    1020
cgatag                                                                1026

<210> SEQ ID NO 2
<211> LENGTH: 341
<212> TYPE: PRT
<213> ORGANISM: Oryza sativa
```

```
<400> SEQUENCE: 2

Met Glu Glu His Asp Tyr Asp Ser Asn Ser Asn Pro Pro Leu Met Ser
1               5                   10                  15

Thr Tyr Lys His Leu Phe Val Glu Gln His Arg Leu Asp Met Asp Met
            20                  25                  30

Gly Ala Ile Asp Val Asp Glu Cys Glu Leu Pro Val Ile Asp Leu Ala
        35                  40                  45

Gly Leu Met Glu Ala Glu Gln Val Cys Arg Ala Asp Met Val Arg Ala
    50                  55                  60

Ala Ser Glu Trp Gly Phe Phe Gln Val Thr Asn His Gly Val Pro Gln
65                  70                  75                  80

Ala Leu Leu Arg Glu Leu His Asp Ala Gln Val Ala Val Phe Arg Arg
                85                  90                  95

Pro Phe Gln Glu Lys Val Thr Glu Arg Leu Leu Gly Phe Ser Pro Glu
            100                 105                 110

Ser Tyr Arg Trp Gly Thr Pro Thr Ala Lys Cys Leu Glu Gln Leu Ser
        115                 120                 125

Trp Ser Glu Ala Tyr His Ile Pro Met Thr Thr Pro Arg Pro Ser Thr
130                 135                 140

Ser Ile Arg Ala Arg Ala Val Ile Glu Glu Val Ser Arg Ala Met Tyr
145                 150                 155                 160

Glu Leu Ala Gln Lys Leu Ala Glu Ile Leu Met Arg Gly Leu Pro Gly
                165                 170                 175

Ala Gly Glu Gly Glu Thr Met Val Thr Thr Arg Glu Glu Thr Cys Phe
            180                 185                 190

Leu Arg Leu Asn Arg Tyr Pro Pro Cys Ala Met Ala Met Gly Gly Phe
        195                 200                 205

Gly Leu Cys Pro His Thr Asp Ser Asp Leu Leu Thr Ile Val His Gln
    210                 215                 220

Gln Gln Asp Thr Val Gly Gly Leu Gln Leu Leu Lys Gly Gly Arg Trp
225                 230                 235                 240

Val Ala Val Lys Pro Ser Pro Ser Thr Leu Ile Val Asn Val Gly Asp
                245                 250                 255

Leu Leu Gln Ala Trp Ser Asn Asp Val Tyr Lys Ser Val Glu His Arg
            260                 265                 270

Val Met Ala Asn Ala Thr Leu Glu Arg Phe Ser Met Ala Phe Phe Leu
        275                 280                 285

Cys Pro Ser Tyr His Thr Leu Ile Ile Pro Ser Ser His Val His
    290                 295                 300

Asp Asp Asp Ala His Tyr Arg Ser Phe Thr Phe Gly Glu Tyr Arg Lys
305                 310                 315                 320

Gln Ile Met Glu Asp Val Arg Ser Thr Gly Arg Lys Ile Gly Leu His
                325                 330                 335

Arg Phe Arg Thr Arg
            340

<210> SEQ ID NO 3
<211> LENGTH: 1113
<212> TYPE: DNA
<213> ORGANISM: Oryza sativa

<400> SEQUENCE: 3
atgtcgaggc tggccagggc gctggcgcgc gtgctggcgg agagcctcct gggccacgcc      60
gccggcgagc gattcccgga ggggtgcgac gacgcgacgt gcttcctccg gctgaaccgc     120
```

```
taccegccgt gecccttece accggacgac gecttcggec tggtccegca caccgacagc      180 gacttcctca ccgtgctctg ccaggaccac gtcggcggcc tgcagctcat gaagggctcc      240
cgctgggtcg ccgtcaagcc catccccggc gccctcatcg tcaacatcgg agaccttttt      300
caggcgtgga gcaacaacag gtacaagagc gtggagcaca gggtgatgac gaacgcgacg      360
acggagagat actccgtcgc ctacttcctc tgcccgtcgt acgactcgcc catcggcacg      420
tgcagggagc cttcccctta caaggcgttc accttcgggg agtacaggcg aagggtgcag      480
gaagacgtca agaagacggg gaagaagact ggcctcagta atttcctcct tagtttgacg      540
gtgtacaagt actgccttgc cggcggcggc ggcggagggc agcggcggaa catacaggcc      600
gactcatctt catccgcgag gacatggaga aagccggaag ccgggtggat aaagctcaac      660
ttcgatgggt cgtctaagca cgcgaccaag atcgcgagca tcggcggcgt gtaccgcgac      720
cacgagggcg cattcgtgct cggctacgcg gagcggatcg gcagagcgac gagctccgtc      780
gcggagctcg cggcgctcag gcgcggcctc gagctggtgt gcggaacgg gtggcggcgc      840 gtctgggcgg agggcgactc caagacggtg gtcgacgtgg tgtgcgaccg cgccaacgtg      900
cggtcggagg aggacctgag acagtgcagg gagatcgccg cgctgctccc gctgatcgat      960
gacatggccg tgtcacacgt gtaccgcagc gggaacaagg tggcgcacgg cttcgccagg     1020
ctcggacaca aggcggtgcg cccgcgggtg tggcgcgccg cgccgcccga ggaggtgctc     1080
cggttcctcc aacaagacgc cgatcaacga taa                                  1113
```

<210> SEQ ID NO 4
<211> LENGTH: 358
<212> TYPE: PRT
<213> ORGANISM: Oryza sativa

<400> SEQUENCE: 4

```
Met Pro Ala Phe Ala Asp Ile Ala Ile Asp Pro Pro Leu Ala Asp Ser
1               5                   10                  15

Tyr Arg Ala Leu Ala Leu Leu Arg Arg Asp Arg Asp Gly Gly Ile Ala
                20                  25                  30

Pro Pro Ala Val Gln Met Val Gly Ser Gly Gly Ala Val Leu Glu Arg
            35                  40                  45

Asp Leu Pro Met Val Asp Leu Glu Arg Leu Thr Arg Gly Gly Ala Gly
        50                  55                  60

Glu Arg Lys Ala Cys Ala Gly Ala Met Ala Arg Ala Ala Ser Glu Trp
65                  70                  75                  80

Gly Phe Phe Gln Leu Thr Asn His Gly Val Gly Arg Glu Leu Met Glu
                85                  90                  95

Glu Met Arg Arg Glu Gln Ala Arg Leu Phe Arg Leu Pro Phe Glu Thr
                100                 105                 110

Lys Glu Lys Ala Gly Leu Leu Asn Gly Ser Tyr Arg Trp Gly Asn Pro
            115                 120                 125

Thr Ala Thr Ser Leu Arg His Leu Ser Trp Ser Glu Ala Phe His Val
        130                 135                 140

Pro Leu Ala Ser Ile Ser Gly Ala Asp Cys Asp Phe Gly Asp Leu Thr
145                 150                 155                 160

Ser Leu Arg Gly Val Met Gln Glu Val Ala Glu Ala Met Ser Arg Val
                165                 170                 175

Ala Asn Thr Val Ala Ala Leu Ala Glu Glu Leu Thr Gly Arg Gly
            180                 185                 190

Gly Gly Gly Ala Ser Ala Ala Pro Trp Phe Pro Ala Gly Cys Asp Glu
        195                 200                 205
```

Thr Thr Cys Phe Leu Arg Leu Asn Arg Tyr Pro Ala Cys Pro Phe Ala
    210                 215                 220

Ala Asp Thr Phe Gly Leu Val Pro His Thr Asp Ser Asp Phe Leu Thr
225                 230                 235                 240

Val Leu Cys Gln Asp Gln Val Gly Gly Leu His Leu Met Lys Asp Ser
                245                 250                 255

Arg Trp Val Ala Val Arg Pro Arg Pro Asp Ala Leu Val Val Asn Ile
            260                 265                 270

Gly Asp Leu Phe Gln Ala Trp Ser Asn Asn Arg Tyr Lys Ser Val Glu
        275                 280                 285

His Lys Val Val Ala Asn Ala Lys Thr Asp Arg Leu Ser Val Ala Tyr
    290                 295                 300

Phe Leu Cys Pro Ser Tyr Asp Ser Leu Val Gly Thr Cys Gly Glu Pro
305                 310                 315                 320

Ser Pro Tyr Arg Ala Phe Thr Phe Gly Glu Tyr Arg Lys Lys Val Gln
                325                 330                 335

Glu Asp Val Arg Thr Thr Gly Lys Lys Ile Gly Leu Pro Asn Phe Phe
            340                 345                 350

Lys His Ser Ser Val Gln
        355

<210> SEQ ID NO 5
<211> LENGTH: 1008
<212> TYPE: DNA
<213> ORGANISM: Oryza sativa

<400> SEQUENCE: 5
atggtggtgc ttgccaaggg cgagctcgag cagatagccc tgccggcggc gcacccgccg     60
ccagccgacg tgcgcgcgat cgacctgtcc gccacgggtc ccgcccgcgc ggcggaggcg    120
cgcgcgctgg tggcggcgtg cgaggagcag gggttcttcc gggtgacggg ccacggcgtg    180
ccgccggggc tggtgcgcgc cgcggaggcc gccgcggcgc ggttcttcgc gctgccgcag    240
cccgacaagg aggccgccgc aggggcgccg ctcgggtacg ccagcaagcg gatcggcagc    300
gccggcgacc tcggctggat cgagtacctg ctactctgcc tcgccccgc cgccgccgcc    360 gcggcattgc cgtgcgccgc gacgtcgccc acgcctcctt gccccttacg ggagcttcta    420
cgcgagtaca gcgcggcggt gcggcgggtg cgtgcgggc tgctggagct gatggcggag    480
gggctcggcg tcgggccggc ggacgcgctg gcgcggctgg tggcgcgcga ggacagcgac    540
tccatcctca gggtgaacca ctacccgccg cgccccgatc agctgggcgg cggcggcggg    600
ccgaacctga cggggttcgg cgagcacacc gacccgcaga tcatctccgt gctccgctcc    660
aacggcgccc ccgggctgga gatctccctc cgtgacggcg cctgggcgtc cgtgccgcac    720
gacggcgacg cgactccctt tttcgtcaac gtcggcgaca ccctccaggt gctaacgaac    780
gggaggttca ggagcgtgaa gcacagggtg gtggtgaaca gcgagaagtc gagggtgtcc    840
atggtcttct cggcggccc gccgccccgc gagaggctgg cgccgctgcc ggcgttatta    900
ggggacggcg gccggagccg gtacagggag ttcacctgga aggagtacaa gggcagcggc    960
tgcaagggcc ggctcgccga cgacaggctc tgcagatttg agaactag              1008

<210> SEQ ID NO 6
<211> LENGTH: 335
<212> TYPE: PRT
<213> ORGANISM: Oryza sativa

<400> SEQUENCE: 6

| Met | Val | Val | Leu | Ala | Lys | Gly | Glu | Leu | Glu | Gln | Ile | Ala | Leu | Pro | Ala |
| 1 | | | | 5 | | | | | 10 | | | | | 15 | |

| Ala | His | Pro | Pro | Ala | Asp | Val | Arg | Ala | Ile | Asp | Leu | Ser | Ala | Thr |
| | | | 20 | | | | | 25 | | | | | 30 | |

| Gly | Pro | Ala | Arg | Ala | Ala | Glu | Ala | Arg | Ala | Leu | Val | Ala | Ala | Cys | Glu |
| | | 35 | | | | | 40 | | | | | 45 | | | |

| Glu | Gln | Gly | Phe | Phe | Arg | Val | Thr | Gly | His | Gly | Val | Pro | Pro | Gly | Leu |
| | 50 | | | | | 55 | | | | | 60 | | | | |

| Val | Arg | Ala | Ala | Glu | Ala | Ala | Ala | Ala | Arg | Phe | Phe | Ala | Leu | Pro | Gln |
| 65 | | | | | 70 | | | | | 75 | | | | | 80 |

| Pro | Asp | Lys | Glu | Ala | Ala | Ala | Gly | Ala | Pro | Leu | Gly | Tyr | Ala | Ser | Lys |
| | | | | 85 | | | | | 90 | | | | | 95 | |

| Arg | Ile | Gly | Ser | Ala | Gly | Asp | Leu | Gly | Trp | Ile | Glu | Tyr | Leu | Leu | Leu |
| | | | 100 | | | | | 105 | | | | | 110 | | |

| Cys | Leu | Ala | Pro | Ala | Ala | Ala | Ala | Ala | Leu | Pro | Cys | Ala | Ala | Thr |
| | | 115 | | | | | 120 | | | | | 125 | | |

| Ser | Pro | Thr | Pro | Pro | Cys | Pro | Leu | Arg | Glu | Leu | Leu | Arg | Glu | Tyr | Ser |
| | 130 | | | | | 135 | | | | | 140 | | | | |

| Ala | Ala | Val | Arg | Arg | Val | Ala | Cys | Gly | Val | Leu | Glu | Leu | Met | Ala | Glu |
| 145 | | | | | 150 | | | | | 155 | | | | | 160 |

| Gly | Leu | Gly | Val | Gly | Pro | Ala | Asp | Ala | Leu | Ala | Arg | Leu | Val | Ala | Arg |
| | | | | 165 | | | | | 170 | | | | | 175 | |

| Glu | Asp | Ser | Asp | Ser | Ile | Leu | Arg | Val | Asn | His | Tyr | Pro | Pro | Arg | Pro |
| | | | 180 | | | | | 185 | | | | | 190 | | |

| Asp | Gln | Leu | Gly | Gly | Gly | Gly | Pro | Asn | Leu | Thr | Gly | Phe | Gly | Glu |
| | | 195 | | | | | 200 | | | | | 205 | | |

| His | Thr | Asp | Pro | Gln | Ile | Ile | Ser | Val | Leu | Arg | Ser | Asn | Gly | Ala | Pro |
| | 210 | | | | | 215 | | | | | 220 | | | | |

| Gly | Leu | Glu | Ile | Ser | Leu | Arg | Asp | Gly | Ala | Trp | Ala | Ser | Val | Pro | His |
| 225 | | | | | 230 | | | | | 235 | | | | | 240 |

| Asp | Gly | Asp | Gly | Asp | Ser | Phe | Phe | Val | Asn | Val | Gly | Asp | Thr | Leu | Gln |
| | | | | 245 | | | | | 250 | | | | | 255 | |

| Val | Leu | Thr | Asn | Gly | Arg | Phe | Arg | Ser | Val | Lys | His | Arg | Val | Val | Val |
| | | | 260 | | | | | 265 | | | | | 270 | | |

| Asn | Ser | Glu | Lys | Ser | Arg | Val | Ser | Met | Val | Phe | Phe | Gly | Gly | Pro | Pro |
| | | 275 | | | | | 280 | | | | | 285 | | | |

| Pro | Gly | Glu | Arg | Leu | Ala | Pro | Leu | Pro | Ala | Leu | Leu | Gly | Asp | Gly | Gly |
| | 290 | | | | | 295 | | | | | 300 | | | | |

| Arg | Ser | Arg | Tyr | Arg | Glu | Phe | Thr | Trp | Lys | Glu | Tyr | Lys | Gly | Ser | Gly |
| 305 | | | | | 310 | | | | | 315 | | | | | 320 |

| Cys | Lys | Gly | Arg | Leu | Ala | Asp | Asp | Arg | Leu | Cys | Arg | Phe | Glu | Asn |
| | | | | 325 | | | | | 330 | | | | | 335 |

<210> SEQ ID NO 7
<211> LENGTH: 1062
<212> TYPE: DNA
<213> ORGANISM: Oryza sativa

<400> SEQUENCE: 7

| atggtggcga | tcacggcgcc | gagctccatc | gagcacatcc | cgctggtgag | gtgcccaag | 60 |
| ggcgccaatg | ccgggccgca | agctgtcatc | ccgtgcatcg | acctgtcggc | accgggcgcg | 120 |
| gcggcggcgg | tggccgacgc | gtgccgcacc | ctggggttct | tcaaggcgac | caaccacggc | 180 |
| gtccccgcgg | ggctcgccga | cgcgttggag | tcgagcgcca | tggcgttctt | cgcgctcccg | 240 |

-continued

```
caccaggaga agctcgacat gtccggcccc gcccggcccc tcggctacgg cagcaagagc    300
atcgggtcga acggcgacgt ggggtggctg gagtacctcc tcctctcggc cggcgccgcc    360
tcgtccggcg gcgcggcgct gccggcggcg ctgagggcgg cggtggaggc gtacacgggg    420
gcggtgaggg gggtggggtg cagggtgatg gagctgatgg cggaggggct ggggctgggg    480
gcgtcggagg aggggaggtg cgtgctgcgg cggatggtgg tggggtgcga gggcagcgac    540
gagatgctgc gggtgaacca ctacccgccg tgcctcctcc cgccgggccg cgaccgggac    600
gagtgcggcg tgacgggctt cggggagcac acggacccac agatcatctc cgtgctcagg    660
tccaactgca ccgcgggcct ccagatcctc ctccgcggag actactcctc ccctgcccgc    720
tgggtccccg tgcccccccga ccccgattcc ttcttcgtca acgtcggcga ctccctccaa    780
gtgttgacga atgggaggtt caggagcgtg aagcacaggg tgttggcgcc ggaggggggag    840 gagtcgaggc tgtcggtgat ctacttcggc gggccagcgg cgtcgcagcg gatcgcgccg    900
ctggagcagg tgatgcggga gggggagcag agcctgtaca gggagttcac ctgggggggag    960 tacaagaagg ccgcctacaa gacgcgcctc ggcgacaacc gcctcggccc ctacgagctg   1020
cagcacgccg ctgccaacga tgaggccgcg acgaagaaat aa                      1062
```

<210> SEQ ID NO 8
<211> LENGTH: 353
<212> TYPE: PRT
<213> ORGANISM: Oryza sativa

<400> SEQUENCE: 8

```
Met Val Ala Ile Thr Ala Pro Ser Ser Ile Glu His Ile Pro Leu Val
1               5                   10                  15

Arg Cys Pro Lys Gly Ala Asn Ala Gly Pro Gln Ala Val Ile Pro Cys
            20                  25                  30

Ile Asp Leu Ser Ala Pro Gly Ala Ala Ala Val Ala Asp Ala Cys
        35                  40                  45

Arg Thr Leu Gly Phe Phe Lys Ala Thr Asn His Gly Val Pro Ala Gly
    50                  55                  60

Leu Ala Asp Ala Leu Glu Ser Ser Ala Met Ala Phe Phe Ala Leu Pro
65                  70                  75                  80

His Gln Glu Lys Leu Asp Met Ser Gly Pro Ala Arg Pro Leu Gly Tyr
                85                  90                  95

Gly Ser Lys Ser Ile Gly Ser Asn Gly Asp Val Gly Trp Leu Glu Tyr
            100                 105                 110

Leu Leu Leu Ser Ala Gly Ala Ala Ser Ser Gly Ala Ala Leu Pro
        115                 120                 125

Ala Ala Leu Arg Ala Ala Val Glu Ala Tyr Thr Gly Ala Val Arg Gly
    130                 135                 140

Val Gly Cys Arg Val Met Glu Leu Met Ala Glu Gly Leu Gly Leu Gly
145                 150                 155                 160

Ala Ser Glu Glu Gly Arg Cys Val Leu Arg Arg Met Val Val Gly Cys
                165                 170                 175

Glu Gly Ser Asp Glu Met Leu Arg Val Asn His Tyr Pro Pro Cys Leu
            180                 185                 190

Leu Pro Pro Gly Arg Asp Arg Asp Glu Cys Gly Val Thr Gly Phe Gly
        195                 200                 205

Glu His Thr Asp Pro Gln Ile Ile Ser Val Leu Arg Ser Asn Cys Thr
    210                 215                 220

Ala Gly Leu Gln Ile Leu Leu Arg Gly Asp Tyr Ser Ser Pro Ala Arg
225                 230                 235                 240
```

```
Trp Val Pro Val Pro Asp Pro Asp Ser Phe Phe Val Asn Val Gly
            245                 250                 255

Asp Ser Leu Gln Val Leu Thr Asn Gly Arg Phe Arg Ser Val Lys His
            260                 265                 270

Arg Val Leu Ala Pro Glu Gly Glu Ser Arg Leu Ser Val Ile Tyr
        275                 280                 285

Phe Gly Gly Pro Ala Ala Ser Gln Arg Ile Ala Pro Leu Glu Gln Val
        290                 295                 300

Met Arg Glu Gly Glu Gln Ser Leu Tyr Arg Glu Phe Thr Trp Gly Glu
305                 310                 315                 320

Tyr Lys Lys Ala Ala Tyr Lys Thr Arg Leu Gly Asp Asn Arg Leu Gly
                325                 330                 335

Pro Tyr Glu Leu Gln His Ala Ala Ala Asn Asp Glu Ala Ala Thr Lys
            340                 345                 350

Lys
```

<210> SEQ ID NO 9
<211> LENGTH: 1080
<212> TYPE: DNA
<213> ORGANISM: Oryza sativa

<400> SEQUENCE: 9

```
atgccggcca tcgcggattg cgcggccgac ccgccgctgg cggacagcta ctacacgctg      60
ctccgcctcg gcggggacga cgacgacgac gcgtgcacga aggtgaccac gacgccgcag     120
cccgtgtcgg agtgcgagct cccgatgatc gacgtcggtt gcctgacggc gccgaccggc     180
gccgccgccg ccgccgccgt ggggcagcag catcaagccg aggagagggc ggcctgcgcg     240
gcggccatcg cggcggcggc cgcggagtgg gggttcttcc aggtggtgaa ccacggcgtc     300
gcgcaggagc tcctggaggc gatgcgccgg gagcaggcgc ggctgttccg cctcccgttc     360
gaggccaagt ccagcgccgg cctcctcaac gactcctacc gctgggcac cccgaccgcc     420
acctcgctcc gccagctctc ctggtcggag gccttccacc tcccgctcgc cggcatctcc     480
ggcaaatcct gcaactacgg cgacctcacc tccctcaggg acgtgacgcg ggaggtggcg     540
gacgcgatgt cgaggctggc cagggcgctg gcgcgcgtgc tggcggagag cctcctgggc     600
cacgccgccg cgagcgatt cccggagggg tgcgacacg cgacgtgctt cctccggctg     660
aaccgctacc gccgtgccc cttccacccg gacgacgcct cggcctggg cccgcacacc     720
gacagcgact cctccaccgt gctctgccag gaccacgtcg gcggcctgca gctcatgaag     780
ggctcccgct gggtcgccgt caagcccatc cccggcgccc tcatcgtcaa catcggagac     840
ctttttcagg cgtggagcaa caacaggtac aagagcgtgg agcacagggt gatgacgaac     900
gcgacgacgg agagatactc cgtcgcctac ttcctctgcc cgtcgtacga ctcgcccatc     960
ggcacgtgca gggagccttc cccttacaag gcgttcaccc tcggggagta caggcgaagg    1020
gtgcaggaag acgtcaagaa gacggggaag aagactggcc tcagtaattt cctcgtatga    1080
```

<210> SEQ ID NO 10
<211> LENGTH: 359
<212> TYPE: PRT
<213> ORGANISM: Oryza sativa

<400> SEQUENCE: 10

```
Met Pro Ala Ile Ala Asp Cys Ala Ala Asp Pro Pro Leu Ala Asp Ser
1               5                   10                  15

Tyr Tyr Thr Leu Leu Arg Leu Gly Gly Asp Asp Asp Asp Ala Cys
```

```
                    20                  25                  30
Thr Lys Val Thr Thr Thr Pro Gln Pro Val Ser Glu Cys Glu Leu Pro
                35                  40                  45
Met Ile Asp Val Gly Cys Leu Thr Ala Pro Thr Gly Ala Ala Ala Ala
 50                  55                  60
Ala Ala Val Gly Gln Gln His Gln Ala Glu Glu Arg Ala Ala Cys Ala
 65                  70                  75                  80
Ala Ala Ile Ala Ala Ala Ala Glu Trp Gly Phe Phe Gln Val Val
                85                  90                  95
Asn His Gly Val Ala Gln Glu Leu Leu Glu Ala Met Arg Arg Glu Gln
            100                 105                 110
Ala Arg Leu Phe Arg Leu Pro Phe Glu Ala Lys Ser Ser Ala Gly Leu
            115                 120                 125
Leu Asn Asp Ser Tyr Arg Trp Gly Thr Pro Thr Ala Thr Ser Leu Arg
        130                 135                 140
Gln Leu Ser Trp Ser Glu Ala Phe His Leu Pro Leu Ala Gly Ile Ser
145                 150                 155                 160
Gly Lys Ser Cys Asn Tyr Gly Asp Leu Thr Ser Leu Arg Asp Val Thr
                165                 170                 175
Arg Glu Val Ala Asp Ala Met Ser Arg Leu Ala Arg Ala Leu Ala Arg
            180                 185                 190
Val Leu Ala Glu Ser Leu Leu Gly His Ala Ala Gly Glu Arg Phe Pro
            195                 200                 205
Glu Gly Cys Asp Asp Ala Thr Cys Phe Leu Arg Leu Asn Arg Tyr Pro
        210                 215                 220
Pro Cys Pro Phe Pro Pro Asp Asp Ala Phe Gly Leu Val Pro His Thr
225                 230                 235                 240
Asp Ser Asp Phe Leu Thr Val Leu Cys Gln Asp His Val Gly Gly Leu
                245                 250                 255
Gln Leu Met Lys Gly Ser Arg Trp Val Ala Val Lys Pro Ile Pro Gly
            260                 265                 270
Ala Leu Ile Val Asn Ile Gly Asp Leu Phe Gln Ala Trp Ser Asn Asn
            275                 280                 285
Arg Tyr Lys Ser Val Glu His Arg Val Met Thr Asn Ala Thr Thr Glu
        290                 295                 300
Arg Tyr Ser Val Ala Tyr Phe Leu Cys Pro Ser Tyr Asp Ser Pro Ile
305                 310                 315                 320
Gly Thr Cys Arg Glu Pro Ser Pro Tyr Lys Ala Phe Thr Phe Gly Glu
                325                 330                 335
Tyr Arg Arg Arg Val Gln Glu Asp Val Lys Lys Thr Gly Lys Lys Thr
            340                 345                 350
Gly Leu Ser Asn Phe Leu Val
        355

<210> SEQ ID NO 11
<211> LENGTH: 900
<212> TYPE: DNA
<213> ORGANISM: Oryza sativa

<400> SEQUENCE: 11
atgccggcca tcgcggattg cgcggccgac ccgccgctgg cggacagcta ctacacgctg     60
ctccgcctcg gcggggacga cgacgacgac gcgtgcacga aggtgaccac gacgccgcag    120
cccgtgtcgg agtgcgagct cccgatgatc gacgtcggtt gcctgacggc gccgaccggc    180
gccgccgccg ccgccgccgt ggggcagcag catcaagccg aggagagggc ggcctgcgcg    240
```

```
gcggccatcg cggcggcggc cgcggagtgg gggttcttcc aggtggtgaa ccacggcgtc    300
gcgcaggagc tcctggaggc gatgcgccgg gagcaggcgc ggctgttccg cctcccgttc    360
gaggccaagt ccagcgccgg cctcctcaac gactcctacc gctggggcac cccgaccgcc    420
acctcgctcc gccagctctc ctggtcggag gccttccacc tcccgctcgc cggcatctcc    480
ggcaaatcct gcaactacgg cgacctcacc tccctcaggg acgtgacgcg ggaggtggcg    540
gacgcgatgt cgaggctggc cagggcgctg gcgcgcgtgc tggcggagag cctcctgggc    600
cacgccgccg gcgagcgatt cccggagggg tgcgacgacg cgacgtgctt cctccggctg    660
aaccgctacc cgccgtgccc cttcccaccg gacgacgcct tcggcctggt cccgcacacc    720
gacagcgact cctcaccgt gctctgccag gaccacgtcg gcggcctgca gctcatgaag    780
ggctcccgct gggtcgccgt caagcccatc cccggcgccc tcatcgtcaa catcggagac    840 cttttttcagg tacacccatt aactccaacg ttgtataaac atctcaacac aaatccctaa    900
```

<210> SEQ ID NO 12
<211> LENGTH: 299
<212> TYPE: PRT
<213> ORGANISM: Oryza sativa

<400> SEQUENCE: 12

```
Met Pro Ala Ile Ala Asp Cys Ala Ala Asp Pro Leu Ala Asp Ser
  1               5                  10                  15

Tyr Tyr Thr Leu Leu Arg Leu Gly Gly Asp Asp Asp Asp Ala Cys
                 20                  25                  30

Thr Lys Val Thr Thr Thr Pro Gln Pro Val Ser Glu Cys Glu Leu Pro
             35                  40                  45

Met Ile Asp Val Gly Cys Leu Thr Ala Pro Thr Gly Ala Ala Ala Ala
         50                  55                  60

Ala Ala Val Gly Gln Gln His Gln Ala Glu Glu Arg Ala Ala Cys Ala
 65                  70                  75                  80

Ala Ala Ile Ala Ala Ala Ala Ala Glu Trp Gly Phe Phe Gln Val Val
                 85                  90                  95

Asn His Gly Val Ala Gln Glu Leu Leu Glu Ala Met Arg Arg Glu Gln
                100                 105                 110

Ala Arg Leu Phe Arg Leu Pro Phe Glu Ala Lys Ser Ser Ala Gly Leu
             115                 120                 125

Leu Asn Asp Ser Tyr Arg Trp Gly Thr Pro Thr Ala Thr Ser Leu Arg
130                 135                 140

Gln Leu Ser Trp Ser Glu Ala Phe His Leu Pro Leu Ala Gly Ile Ser
145                 150                 155                 160

Gly Lys Ser Cys Asn Tyr Gly Asp Leu Thr Ser Leu Arg Asp Val Thr
                165                 170                 175

Arg Glu Val Ala Asp Ala Met Ser Arg Leu Ala Arg Ala Leu Ala Arg
            180                 185                 190

Val Leu Ala Glu Ser Leu Leu Gly His Ala Ala Gly Glu Arg Phe Pro
        195                 200                 205

Glu Gly Cys Asp Asp Ala Thr Cys Phe Leu Arg Leu Asn Arg Tyr Pro
    210                 215                 220

Pro Cys Pro Phe Pro Pro Asp Asp Ala Phe Gly Leu Val Pro His Thr
225                 230                 235                 240

Asp Ser Asp Phe Leu Thr Val Leu Cys Gln Asp His Val Gly Gly Leu
                245                 250                 255

Gln Leu Met Lys Gly Ser Arg Trp Val Ala Val Lys Pro Ile Pro Gly
```

```
              260                 265                 270
Ala Leu Ile Val Asn Ile Gly Asp Leu Phe Gln Val His Pro Leu Thr
            275                 280                 285

Pro Thr Leu Tyr Lys His Leu Asn Thr Asn Pro
        290                 295

<210> SEQ ID NO 13
<211> LENGTH: 1137
<212> TYPE: DNA
<213> ORGANISM: Oryza sativa

<400> SEQUENCE: 13
atggcgcagc cggagaagga ggcggcggcg gcggcggccg ccgccgccgt gccggggagc     60
ccgttcgggt acgggagcaa gaggatcggc tgcaacgggg acctcgggtg gtcgagtac    120 ctcctgctcg gcgtcgccgc cgccgccgcc gcgccattgc ccgcgcacgg cgaggcgtcg    180
ccgtcgccgt cgtacggctc gttccgcgat atcttaaatg agtacgttgt ggcggtgaga    240
gcgatgatgt gggaggtgct aaagttaatg gcggaagggc taggcctgaa ggagaaagat    300
gcgttggtta ggctggtctc acacgaggag agtgactccg tgctgagggt gaaccactac    360
ccaccacacc ctgagttgaa gcagcaaggc catggtaggt taaccgggtt tggagagcac    420
accgaccctc agatcatctc ggtgctccga tccaacgaca cctctggcct tgagatctct    480
ttgcgtgatg gtagctgggc ttctgtgcct ccggatcgaa agtcgttctt cgttaatgtt    540
ggagatgtct tacagccagg tggtagaatt aaattagagg aactgcaagg ttttcttcat    600
gccgtgtcgc tccgctccag ggcaacacgg gaggcgaccc gaagccgccc cgccgccggc    660
cttctctccc tcgcctcccc cacctcgccg ccgcctgagc agccgccggc aaagccggac    720
ggcggcaagg acggcggcgg cggggccttc taccccctcc aacaccctgc ggttggggcc    780
ccgacgggaa acaggcggag gggcggcgac gcgtcgaggc ggctccggcg acgccgacgg    840
ccagaggcag cagagccagc gtcgctgtta gcggatctgg ccccctcgca gccagatcgg    900
gacgaagtgg cgccggccgc gctgcatcag gacgaggcgc tggctggggc agtcgtggcg    960
ccggcggaga aggccgctgg atggggcagt cgcggcgcgg gcggaggcga cgtcgctggc   1020
ggcggggacg aggcagcgag cctgggcgcc gctggatctg gctctcccag gccggatcca   1080
acgcccgcag ctgggccacg aaggaggccg gctccggggc ggcggcggcg gcgatga      1137

<210> SEQ ID NO 14
<211> LENGTH: 378
<212> TYPE: PRT
<213> ORGANISM: Oryza sativa

<400> SEQUENCE: 14

Met Ala Gln Pro Glu Lys Glu Ala Ala Ala Ala Ala Ala Ala Ala Ala
1               5                   10                  15

Val Pro Gly Ser Pro Phe Gly Tyr Gly Ser Lys Arg Ile Gly Cys Asn
            20                  25                  30

Gly Asp Leu Gly Trp Val Glu Tyr Leu Leu Leu Gly Val Ala Ala Ala
        35                  40                  45

Ala Ala Ala Pro Leu Pro Ala His Gly Glu Ala Ser Pro Ser Pro Ser
    50                  55                  60

Tyr Gly Ser Phe Arg Asp Ile Leu Asn Glu Tyr Val Val Ala Val Arg
65                  70                  75                  80

Ala Met Met Trp Glu Val Leu Lys Leu Met Ala Glu Gly Leu Gly Leu
                85                  90                  95
```

```
Lys Glu Lys Asp Ala Leu Val Arg Leu Val Ser His Glu Glu Ser Asp
            100                 105                 110

Ser Val Leu Arg Val Asn His Tyr Pro Pro His Pro Glu Leu Lys Gln
        115                 120                 125

Gln Gly His Gly Arg Leu Thr Gly Phe Gly Glu His Thr Asp Pro Gln
    130                 135                 140

Ile Ile Ser Val Leu Arg Ser Asn Asp Thr Ser Gly Leu Glu Ile Ser
145                 150                 155                 160

Leu Arg Asp Gly Ser Trp Ala Ser Val Pro Asp Arg Lys Ser Phe
        165                 170                 175

Phe Val Asn Val Gly Asp Val Leu Gln Pro Gly Gly Arg Ile Lys Leu
        180                 185                 190

Glu Glu Leu Gln Gly Phe Leu His Ala Val Ser Leu Arg Ser Arg Ala
        195                 200                 205

Thr Arg Glu Ala Thr Arg Ser Arg Pro Ala Ala Gly Leu Leu Ser Leu
    210                 215                 220

Ala Ser Pro Thr Ser Pro Pro Glu Gln Pro Ala Lys Pro Asp
225                 230                 235                 240

Gly Gly Lys Asp Gly Gly Gly Ala Phe Tyr Pro Leu Gln His Pro
            245                 250                 255

Ala Val Gly Ala Pro Thr Gly Asn Arg Arg Gly Gly Asp Ala Ser
        260                 265                 270

Arg Arg Leu Arg Arg Arg Arg Pro Glu Ala Ala Glu Pro Ala Ser
    275                 280                 285

Leu Leu Ala Asp Leu Ala Pro Ser Gln Pro Asp Arg Asp Glu Val Ala
        290                 295                 300

Pro Ala Ala Leu His Gln Asp Glu Ala Leu Ala Gly Ala Val Val Ala
305                 310                 315                 320

Pro Ala Glu Lys Ala Ala Gly Trp Gly Ser Arg Gly Ala Gly Gly
            325                 330                 335

Asp Val Ala Gly Gly Gly Asp Glu Ala Ala Ser Leu Gly Ala Ala Gly
        340                 345                 350

Ser Gly Ser Pro Arg Pro Asp Pro Thr Pro Ala Ala Gly Pro Arg Arg
        355                 360                 365

Arg Pro Ala Pro Gly Arg Arg Arg Arg
    370                 375

<210> SEQ ID NO 15
<211> LENGTH: 816
<212> TYPE: DNA
<213> ORGANISM: Oryza sativa

<400> SEQUENCE: 15
atggcgcagc cggagaagga ggcggcggcg gcggcggccg ccgccgccgt gccggggagc      60
ccgttcgggt acgggagcaa gaggatcggc tgcaacgggg acctcgggtg gtcgagtac     120 ctcctgctcg gcgtcgccgc cgccgccgcc gcgccattgc ccgcgcacgg cgaggcgtcg     180
ccgtcgccgt cgtacggctc gttccgcgat atcttaaatg agtacgttgt ggcggtgaga     240
gcgatgatgt gggaggtgct aaagttaatg gcggaagggc taggcctgaa ggagaaagat     300
gcgttggtta ggctggtctc acacgaggag agtgactccg tgctgagggt gaaccactac     360
ccaccacacc ctgagttgaa gcagcaaggc catggtaggt taaccgggtt tggagagcac     420
accgaccctc agatcatctc ggtgctccga tccaacgaca cctctggcct tgagatctct     480
ttgcgtgatg gtagctgggc ttctgtgcct ccggatcgaa agtcgttctt cgttaatgtt     540
```

```
ggagatgtct tacagccagg tggtagaatt aaattagagg aactgcaagg ttttcttcat    600
gccgtgtcgc tccgctccag ggcaacacgg gaggcgaccc gaagccgccc cgccgctgga    660
tggggcagtc gcggcgcggg cggaggcgac gtcgctggcg gcggggacga ggcagcgagc    720
ctgggcgccg ctggatctgg ctctcccagg ccggatccaa cgcccgcagc tgggccacga    780
aggaggccgg ctccggggcg gcggcggcgg cgatga                              816
```

<210> SEQ ID NO 16
<211> LENGTH: 271
<212> TYPE: PRT
<213> ORGANISM: Oryza sativa

<400> SEQUENCE: 16

```
Met Ala Gln Pro Glu Lys Glu Ala Ala Ala Ala Ala Ala Ala
1               5                  10                  15

Val Pro Gly Ser Pro Phe Gly Tyr Gly Ser Lys Arg Ile Gly Cys Asn
            20                  25                  30

Gly Asp Leu Gly Trp Val Glu Tyr Leu Leu Gly Val Ala Ala Ala
        35                  40                  45

Ala Ala Ala Pro Leu Pro Ala His Gly Glu Ala Ser Pro Ser Pro Ser
50                  55                  60

Tyr Gly Ser Phe Arg Asp Ile Leu Asn Glu Tyr Val Ala Val Arg
65                  70                  75                  80

Ala Met Met Trp Glu Val Leu Lys Leu Met Ala Glu Gly Leu Gly Leu
                85                  90                  95

Lys Glu Lys Asp Ala Leu Val Arg Leu Val Ser His Glu Glu Ser Asp
            100                 105                 110

Ser Val Leu Arg Val Asn His Tyr Pro Pro His Pro Glu Leu Lys Gln
        115                 120                 125

Gln Gly His Gly Arg Leu Thr Gly Phe Gly Glu His Thr Asp Pro Gln
    130                 135                 140

Ile Ile Ser Val Leu Arg Ser Asn Asp Thr Ser Gly Leu Glu Ile Ser
145                 150                 155                 160

Leu Arg Asp Gly Ser Trp Ala Ser Val Pro Pro Asp Arg Lys Ser Phe
                165                 170                 175

Phe Val Asn Val Gly Asp Val Leu Gln Pro Gly Gly Arg Ile Lys Leu
            180                 185                 190

Glu Glu Leu Gln Gly Phe Leu His Ala Val Ser Leu Arg Ser Arg Ala
        195                 200                 205

Thr Arg Glu Ala Thr Arg Ser Arg Pro Ala Ala Gly Trp Gly Ser Arg
    210                 215                 220

Gly Ala Gly Gly Gly Asp Val Ala Gly Gly Asp Glu Ala Ala Ser
225                 230                 235                 240

Leu Gly Ala Ala Gly Ser Gly Ser Pro Arg Pro Asp Pro Thr Pro Ala
                245                 250                 255

Ala Gly Pro Arg Arg Pro Ala Pro Gly Arg Arg Arg Arg
            260                 265                 270
```

<210> SEQ ID NO 17
<211> LENGTH: 14
<212> TYPE: PRT
<213> ORGANISM: Artificial Sequence
<220> FEATURE:
<223> OTHER INFORMATION: Conserved amino acid sequence of domain III of
      class C20 GA2ox
<220> FEATURE:
<221> NAME/KEY: X
<222> LOCATION: (3)..(3)

```
<223> OTHER INFORMATION: Lys or Arg;
<220> FEATURE:
<221> NAME/KEY: X
<222> LOCATION: (4)..(4)
<223> OTHER INFORMATION: any of the 20 amino acids
<220> FEATURE:
<221> NAME/KEY: X
<222> LOCATION: (5)..(5)
<223> OTHER INFORMATION: Thr or Phe
<220> FEATURE:
<221> NAME/KEY: X
<222> LOCATION: (7)..(7)
<223> OTHER INFORMATION: any of the 20 amino acids
<220> FEATURE:
<221> NAME/KEY: X
<222> LOCATION: (9)..(9)
<223> OTHER INFORMATION: Val, Ile or Thr
<220> FEATURE:
<221> NAME/KEY: X
<222> LOCATION: (12)..(12)
<223> OTHER INFORMATION: any of the 20 amino acids
<220> FEATURE:
<221> NAME/KEY: X
<222> LOCATION: (13)..(13)
<223> OTHER INFORMATION: Arg or Asn

<400> SEQUENCE: 17

Asp Val Xaa Xaa Xaa Gly Xaa Lys Xaa Gly Leu Xaa Xaa Phe
1               5                   10

<210> SEQ ID NO 18
<211> LENGTH: 14
<212> TYPE: PRT
<213> ORGANISM: Oryza sativa

<400> SEQUENCE: 18

Asp Val Arg Ser Thr Gly Arg Lys Ile Gly Leu His Arg Phe
1               5                   10

<210> SEQ ID NO 19
<211> LENGTH: 14
<212> TYPE: PRT
<213> ORGANISM: Oryza sativa

<400> SEQUENCE: 19

Asp Val Arg Thr Thr Gly Lys Lys Ile Gly Leu Pro Asn Phe
1               5                   10

<210> SEQ ID NO 20
<211> LENGTH: 14
<212> TYPE: PRT
<213> ORGANISM: Oryza sativa

<400> SEQUENCE: 20

Asp Val Lys Lys Thr Gly Lys Lys Thr Gly Leu Ser Asn Phe
1               5                   10

<210> SEQ ID NO 21
<211> LENGTH: 14
<212> TYPE: PRT
<213> ORGANISM: Arabidopsis thaliana

<400> SEQUENCE: 21

Asp Val Lys Glu Thr Gly Asp Lys Val Gly Leu Ser Arg Phe
1               5                   10

<210> SEQ ID NO 22
<211> LENGTH: 14
<212> TYPE: PRT
<213> ORGANISM: Arabidopsis thaliana
```

<400> SEQUENCE: 22

Asp Val Lys Lys Phe Gly Phe Lys Val Gly Leu Pro Arg Phe
1               5                   10

<210> SEQ ID NO 23
<211> LENGTH: 14
<212> TYPE: PRT
<213> ORGANISM: Spinacia oleracea

<400> SEQUENCE: 23

Asp Val Arg Glu Phe Gly His Lys Ile Gly Leu Ser Arg Phe
1               5                   10

<210> SEQ ID NO 24
<211> LENGTH: 336
<212> TYPE: PRT
<213> ORGANISM: Arabidopsis thaliana

<400> SEQUENCE: 24

Met Ala Ser Gln Pro Pro Phe Lys Thr Asn Phe Cys Ser Ile Phe Gly
1               5                   10                  15

Ser Ser Phe Pro Asn Ser Thr Ser Glu Ser Asn Thr Asn Thr Ser Thr
            20                  25                  30

Ile Gln Thr Ser Gly Ile Lys Leu Pro Val Ile Asp Leu Ser His Leu
        35                  40                  45

Thr Ser Gly Glu Glu Val Lys Arg Lys Arg Cys Val Lys Gln Met Val
    50                  55                  60

Ala Ala Ala Lys Glu Trp Gly Phe Phe Gln Ile Val Asn His Gly Ile
65                  70                  75                  80

Pro Lys Asp Val Phe Glu Met Met Leu Leu Glu Glu Lys Lys Leu Phe
                85                  90                  95

Asp Gln Pro Phe Ser Val Lys Val Arg Glu Arg Phe Ser Asp Leu Ser
            100                 105                 110

Lys Asn Ser Tyr Arg Trp Gly Asn Pro Ser Ala Thr Ser Pro Ala Gln
        115                 120                 125

Tyr Ser Val Ser Glu Ala Phe His Ile Ile Leu Ser Glu Val Ser Arg
    130                 135                 140

Ile Ser Asp Asp Arg Asn Asn Leu Arg Thr Ile Val Glu Thr Tyr Val
145                 150                 155                 160

Gln Glu Ile Ala Arg Val Ala Gln Met Ile Cys Glu Ile Leu Gly Lys
                165                 170                 175

Gln Val Asn Val Ser Ser Glu Tyr Phe Glu Asn Ile Phe Glu Leu Glu
            180                 185                 190

Asn Ser Phe Leu Arg Leu Asn Lys Tyr His Pro Ser Val Phe Gly Ser
        195                 200                 205

Glu Val Phe Gly Leu Val Pro His Thr Asp Thr Ser Phe Leu Thr Ile
    210                 215                 220

Leu Ser Gln Asp Gln Ile Gly Gly Leu Glu Leu Glu Asn Asn Gly Gln
225                 230                 235                 240

Trp Ile Ser Val Lys Pro Cys Leu Glu Ala Leu Thr Val Asn Ile Gly
                245                 250                 255

Asp Met Phe Gln Ala Leu Ser Asn Gly Val Tyr Gln Ser Val Arg His
            260                 265                 270

Arg Val Ile Ser Pro Ala Asn Ile Glu Arg Met Ser Ile Ala Phe Phe
        275                 280                 285

Val Cys Pro Tyr Leu Glu Thr Glu Ile Asp Cys Phe Gly Tyr Pro Lys

```
                290                 295                 300
Lys Tyr Arg Arg Phe Ser Phe Arg Glu Tyr Lys Glu Gln Ser Glu His
305                 310                 315                 320

Asp Val Lys Glu Thr Gly Asp Lys Val Gly Leu Ser Arg Phe Leu Ile
                325                 330                 335

<210> SEQ ID NO 25
<211> LENGTH: 293
<212> TYPE: PRT
<213> ORGANISM: Arabidopsis thaliana

<400> SEQUENCE: 25

Met Asp Pro Pro Phe Asn Glu Ile Tyr Asn Asn Leu Leu Tyr Asn Gln
1               5                   10                  15

Ile Thr Lys Lys Asp Asn Asp Val Ser Glu Ile Pro Phe Ser Phe Ser
                20                  25                  30

Val Thr Ala Val Glu Glu Val Glu Leu Pro Val Ile Asp Val Ser
            35                  40                  45

Arg Leu Ile Asp Gly Ala Glu Glu Arg Glu Lys Cys Lys Glu Ala
    50                  55                  60

Ile Ala Arg Ala Ser Arg Glu Trp Gly Phe Phe Gln Val Ile Asn His
65                  70                  75                  80

Gly Ile Ser Met Asp Val Leu Glu Lys Met Arg Gln Glu Gln Ile Arg
                85                  90                  95

Val Phe Arg Glu Pro Phe Asp Lys Lys Ser Asn Ser Thr Met Glu Lys
                100                 105                 110

Phe Ala Ser Glu Ser Glu Ala Leu Ala Tyr Met Leu Ala Glu Val Leu
            115                 120                 125

Ala Glu Lys Ser Gly Gln Asn Ser Ser Phe Phe Lys Glu Asn Cys Val
    130                 135                 140

Arg Asn Thr Cys Tyr Leu Arg Met Asn Arg Tyr Pro Pro Cys Pro Lys
145                 150                 155                 160

Pro Ser Glu Val Tyr Gly Leu Met Pro His Thr Asp Ser Asp Phe Leu
                165                 170                 175

Thr Ile Leu Tyr Gln Asp Gln Val Gly Gly Leu Gln Leu Ile Lys Asp
            180                 185                 190

Asn Arg Trp Ile Ala Val Lys Pro Asn Pro Lys Ala Leu Ile Ile Asn
    195                 200                 205

Ile Gly Asp Leu Phe Gln Ala Trp Ser Asn Gly Met Tyr Lys Ser Val
210                 215                 220

Glu His Arg Val Met Thr Asn Pro Lys Val Glu Arg Phe Ser Thr Ala
225                 230                 235                 240

Tyr Phe Met Cys Pro Ser Tyr Asp Ala Val Ile Glu Cys Ser Ser Asp
                245                 250                 255

Arg Pro Ala Tyr Arg Asn Phe Ser Phe Arg Glu Phe Arg Gln Gln Val
            260                 265                 270

Gln Glu Asp Val Lys Lys Phe Gly Phe Lys Val Gly Leu Pro Arg Phe
    275                 280                 285

Leu Asn His Val Tyr
    290

<210> SEQ ID NO 26
<211> LENGTH: 374
<212> TYPE: PRT
<213> ORGANISM: Spinacia oleracea

<400> SEQUENCE: 26
```

```
Met Ala Ser Thr Lys Val Val Glu His Leu Lys Glu Asn Val Leu Trp
 1               5                  10                  15
Lys Gln Ala Ile Met Asp Arg Asn Ala Asn Ile Ser Asp Pro Pro Phe
             20                  25                  30
Glu Glu Thr Tyr Lys Asn Leu Leu Lys His Asn Ile Thr Pro Leu
         35                  40                  45
Thr Thr Thr Thr Thr Thr Thr Thr Thr Ala Thr Ile Glu Val Arg
 50                      55                  60
Asp Leu Pro Leu Ile Asp Leu Ser Arg Leu Val Ala Thr Ala Ala Lys
 65                  70                  75                  80
Glu Arg Glu Asn Cys Lys Arg Asp Ile Ala Asn Ala Ser Arg Glu Trp
                 85                  90                  95
Gly Phe Phe Gln Val Val Asn His Gly Ile Pro His Arg Met Leu Glu
             100                 105                 110
Glu Met Asn Lys Glu Gln Val Lys Val Phe Arg Glu Pro Phe Asn Lys
             115                 120                 125
Lys Lys Gly Asp Asn Cys Met Asn Leu Arg Leu Ser Pro Gly Ser Tyr
130                 135                 140
Arg Trp Gly Ser Pro Thr Pro Asn Cys Leu Ser Gln Leu Ser Trp Ser
145                 150                 155                 160
Glu Ala Phe His Ile Pro Met Asn Asp Ile Cys Ser Asn Ala Pro Arg
                 165                 170                 175
Asn Ile Ala Asn Gly Asn Pro Asn Ile Ser Asn Leu Cys Ser Thr Val
             180                 185                 190
Lys Gln Phe Ala Thr Thr Val Ser Glu Leu Ala Asn Lys Leu Ala Asn
         195                 200                 205
Ile Leu Val Glu Lys Leu Gly His Asp Glu Leu Thr Phe Ile Glu Glu
     210                 215                 220
Lys Cys Ser Pro Asn Thr Cys Tyr Leu Arg Met Asn Arg Tyr Pro Pro
225                 230                 235                 240
Cys Pro Lys Tyr Ser His Val Leu Gly Leu Met Pro His Thr Asp Ser
                 245                 250                 255
Asp Phe Leu Thr Ile Leu Tyr Gln Asp Gln Val Gly Gly Leu Gln Leu
             260                 265                 270
Val Lys Asp Gly Arg Trp Ile Ser Val Lys Pro Asn Pro Glu Ala Leu
         275                 280                 285
Ile Val Asn Ile Gly Asp Leu Phe Gln Ala Trp Ser Asn Gly Val Tyr
     290                 295                 300
Lys Ser Val Val His Arg Val Val Ala Asn Pro Arg Phe Glu Arg Phe
305                 310                 315                 320
Ser Thr Ala Tyr Phe Leu Cys Pro Ser Gly Asp Ala Val Ile Gln Ser
                 325                 330                 335
Tyr Arg Glu Pro Ser Met Tyr Arg Lys Phe Ser Phe Gly Glu Tyr Arg
             340                 345                 350
Gln Gln Val Gln Gln Asp Val Arg Glu Phe Gly His Lys Ile Gly Leu
         355                 360                 365
Ser Arg Phe Leu Ile Cys
     370

<210> SEQ ID NO 27
<211> LENGTH: 334
<212> TYPE: PRT
<213> ORGANISM: Oryza sativa

<400> SEQUENCE: 27
```

Met Glu Glu His Asp Tyr Asp Ser Asn Ser Asn Pro Pro Leu Met Ser
1               5                   10                  15

Thr Tyr Lys His Leu Phe Val Glu Gln His Arg Leu Asp Met Asp Met
            20                  25                  30

Gly Ala Ile Asp Val Asp Glu Cys Glu Leu Pro Val Ile Asp Leu Ala
        35                  40                  45

Gly Leu Met Glu Ala Gln Val Cys Arg Ala Asp Met Val Arg Ala
    50                  55                  60

Ala Ser Glu Trp Gly Phe Phe Gln Val Thr Asn His Gly Val Pro Gln
65                  70                  75                  80

Ala Leu Leu Arg Glu Leu His Asp Ala Gln Val Ala Val Phe Arg Arg
                85                  90                  95

Pro Phe Gln Glu Lys Val Thr Glu Arg Leu Leu Gly Phe Ser Pro Glu
            100                 105                 110

Ser Tyr Arg Trp Gly Thr Pro Thr Ala Lys Cys Leu Glu Gln Leu Ser
            115                 120                 125

Trp Ser Glu Ala Tyr His Ile Pro Met Thr Thr Pro Arg Pro Ser Thr
130                 135                 140

Ser Ile Arg Ala Arg Ala Val Ile Glu Glu Val Ser Arg Ala Met Tyr
145                 150                 155                 160

Glu Leu Ala Gln Lys Leu Ala Glu Ile Leu Met Arg Gly Leu Pro Gly
                165                 170                 175

Ala Gly Glu Gly Glu Thr Met Val Thr Thr Arg Glu Glu Thr Cys Phe
            180                 185                 190

Leu Arg Leu Asn Arg Tyr Pro Pro Cys Ala Met Ala Met Gly Gly Phe
        195                 200                 205

Gly Leu Cys Pro His Thr Asp Ser Asp Leu Leu Thr Ile Val His Gln
    210                 215                 220

Gln Gln Asp Thr Val Gly Gly Leu Gln Leu Leu Lys Gly Gly Arg Trp
225                 230                 235                 240

Val Ala Val Lys Pro Ser Pro Ser Thr Leu Ile Val Asn Val Gly Asp
                245                 250                 255

Leu Leu Gln Ala Trp Ser Asn Asp Val Tyr Lys Ser Val Glu His Arg
            260                 265                 270

Val Met Ala Asn Ala Thr Leu Glu Arg Phe Ser Met Ala Phe Phe Leu
            275                 280                 285

Cys Pro Ser Tyr His Thr Leu Ile Ile Pro Ser Ser His Val His
    290                 295                 300

Asp Asp Asp Ala His Tyr Arg Ser Phe Thr Phe Gly Glu Tyr Arg Lys
305                 310                 315                 320

Gln Ile Met Glu Asp Val Arg Ser Thr Gly Arg Lys Ile Gly
            325                 330

<210> SEQ ID NO 28
<211> LENGTH: 324
<212> TYPE: PRT
<213> ORGANISM: Oryza sativa

<400> SEQUENCE: 28

Met Glu Glu His Asp Tyr Asp Ser Asn Ser Asn Pro Pro Leu Met Ser
1               5                   10                  15

Thr Tyr Lys His Leu Phe Val Glu Gln His Arg Leu Asp Met Asp Met
            20                  25                  30

Gly Ala Ile Asp Val Asp Glu Cys Glu Leu Pro Val Ile Asp Leu Ala
        35                  40                  45

```
Gly Leu Met Glu Ala Glu Gln Val Cys Arg Ala Asp Met Val Arg Ala
    50                  55                  60

Ala Ser Glu Trp Gly Phe Phe Gln Val Thr Asn His Gly Val Pro Gln
65                  70                  75                  80

Ala Leu Leu Arg Glu Leu His Asp Ala Gln Val Ala Val Phe Arg Arg
                85                  90                  95

Pro Phe Gln Glu Lys Val Thr Glu Arg Leu Leu Gly Phe Ser Pro Glu
            100                 105                 110

Ser Tyr Arg Trp Gly Thr Pro Thr Ala Lys Cys Leu Glu Gln Leu Ser
        115                 120                 125

Trp Ser Glu Ala Tyr His Ile Pro Met Thr Thr Pro Arg Pro Ser Thr
    130                 135                 140

Ser Ile Arg Ala Arg Ala Val Ile Glu Val Ser Arg Ala Met Tyr
145                 150                 155                 160

Glu Leu Ala Gln Lys Leu Ala Glu Ile Leu Met Arg Gly Leu Pro Gly
                165                 170                 175

Ala Gly Glu Gly Glu Thr Met Val Thr Thr Arg Glu Glu Thr Cys Phe
            180                 185                 190

Leu Arg Leu Asn Arg Tyr Pro Pro Cys Ala Met Ala Met Gly Gly Phe
        195                 200                 205

Gly Leu Cys Pro His Thr Asp Ser Asp Leu Leu Thr Ile Val His Gln
    210                 215                 220

Gln Gln Asp Thr Val Gly Gly Leu Gln Leu Leu Lys Gly Gly Arg Trp
225                 230                 235                 240

Val Ala Val Lys Pro Ser Pro Ser Thr Leu Ile Val Asn Val Gly Asp
                245                 250                 255

Leu Leu Gln Ala Trp Ser Asn Asp Val Tyr Lys Ser Val Glu His Arg
            260                 265                 270

Val Met Ala Asn Ala Thr Leu Glu Arg Phe Ser Met Ala Phe Phe Leu
        275                 280                 285

Cys Pro Ser Tyr His Thr Leu Ile Ile Pro Ser Ser Ser His Val His
    290                 295                 300

Asp Asp Asp Ala His Tyr Arg Ser Phe Thr Phe Gly Glu Tyr Arg Lys
305                 310                 315                 320

Gln Ile Met Glu

<210> SEQ ID NO 29
<211> LENGTH: 337
<212> TYPE: PRT
<213> ORGANISM: Oryza sativa

<400> SEQUENCE: 29

Met Pro Ala Phe Ala Asp Ile Ala Ile Asp Pro Pro Leu Ala Asp Ser
1               5                   10                  15

Tyr Arg Ala Leu Ala Leu Leu Arg Arg Asp Arg Asp Gly Gly Ile Ala
            20                  25                  30

Pro Pro Ala Val Gln Met Val Gly Ser Gly Gly Ala Val Leu Glu Arg
        35                  40                  45

Asp Leu Pro Met Val Asp Leu Glu Arg Leu Thr Arg Gly Gly Ala Gly
    50                  55                  60

Glu Arg Lys Ala Cys Ala Gly Ala Met Ala Arg Ala Ala Ser Glu Trp
65                  70                  75                  80

Gly Phe Phe Gln Leu Thr Asn His Gly Val Gly Arg Glu Leu Met Glu
                85                  90                  95
```

```
Glu Met Arg Arg Glu Gln Ala Arg Leu Phe Arg Leu Pro Phe Glu Thr
            100                 105                 110
Lys Glu Lys Ala Gly Leu Leu Asn Gly Ser Tyr Arg Trp Gly Asn Pro
        115                 120                 125
Thr Ala Thr Ser Leu Arg His Leu Ser Trp Ser Glu Ala Phe His Val
    130                 135                 140
Pro Leu Ala Ser Ile Ser Gly Ala Asp Cys Asp Phe Gly Asp Leu Thr
145                 150                 155                 160
Ser Leu Arg Gly Val Met Gln Glu Val Ala Glu Ala Met Ser Arg Val
                165                 170                 175
Ala Asn Thr Val Ala Ala Ala Leu Ala Glu Glu Leu Thr Gly Arg Gly
            180                 185                 190
Gly Gly Gly Ala Ser Ala Ala Pro Trp Phe Pro Ala Gly Cys Asp Glu
        195                 200                 205
Thr Thr Cys Phe Leu Arg Leu Asn Arg Tyr Pro Ala Cys Pro Phe Ala
    210                 215                 220
Ala Asp Thr Phe Gly Leu Val Pro His Thr Asp Ser Asp Phe Leu Thr
225                 230                 235                 240
Val Leu Cys Gln Asp Gln Val Gly Gly Leu His Leu Met Lys Asp Ser
                245                 250                 255
Arg Trp Val Ala Val Arg Pro Arg Pro Asp Ala Leu Val Val Asn Ile
            260                 265                 270
Gly Asp Leu Phe Gln Ala Trp Ser Asn Asn Arg Tyr Lys Ser Val Glu
        275                 280                 285
His Lys Val Val Ala Asn Ala Lys Thr Ala Arg Leu Ser Val Ala Tyr
    290                 295                 300
Phe Leu Cys Pro Ser Tyr Asp Ser Leu Val Gly Thr Cys Gly Glu Pro
305                 310                 315                 320
Ser Pro Tyr Arg Ala Phe Thr Phe Gly Glu Tyr Arg Lys Lys Val Gln
                325                 330                 335
Glu

<210> SEQ ID NO 30
<211> LENGTH: 347
<212> TYPE: PRT
<213> ORGANISM: Oryza sativa

<400> SEQUENCE: 30

Met Pro Ala Phe Ala Asp Ile Ala Ile Asp Pro Pro Leu Ala Asp Ser
1               5                   10                  15
Tyr Arg Ala Leu Ala Leu Leu Arg Arg Asp Arg Asp Gly Gly Ile Ala
                20                  25                  30
Pro Pro Ala Val Gln Met Val Gly Ser Gly Gly Ala Val Leu Glu Arg
            35                  40                  45
Asp Leu Pro Met Val Asp Leu Glu Arg Leu Thr Arg Gly Gly Ala Gly
        50                  55                  60
Glu Arg Lys Ala Cys Ala Gly Ala Met Ala Arg Ala Ala Ser Glu Trp
65                  70                  75                  80
Gly Phe Phe Gln Leu Thr Asn His Gly Val Gly Arg Glu Leu Met Glu
                85                  90                  95
Glu Met Arg Arg Glu Gln Ala Arg Leu Phe Arg Leu Pro Phe Glu Thr
            100                 105                 110
Lys Glu Lys Ala Gly Leu Leu Asn Gly Ser Tyr Arg Trp Gly Asn Pro
        115                 120                 125
Thr Ala Thr Ser Leu Arg His Leu Ser Trp Ser Glu Ala Phe His Val
```

```
                    130                 135                 140
Pro Leu Ala Ser Ile Ser Gly Ala Asp Cys Asp Phe Gly Asp Leu Thr
145                 150                 155                 160

Ser Leu Arg Gly Val Met Gln Glu Val Ala Glu Ala Met Ser Arg Val
                165                 170                 175

Ala Asn Thr Val Ala Ala Leu Ala Glu Glu Leu Thr Gly Arg Gly
            180                 185                 190

Gly Gly Gly Ala Ser Ala Ala Pro Trp Phe Pro Ala Gly Cys Asp Glu
                195                 200                 205

Thr Thr Cys Phe Leu Arg Leu Asn Arg Tyr Pro Ala Cys Pro Phe Ala
        210                 215                 220

Ala Asp Thr Phe Gly Leu Val Pro His Thr Asp Ser Asp Phe Leu Thr
225                 230                 235                 240

Val Leu Cys Gln Asp Gln Val Gly Gly Leu His Leu Met Lys Asp Ser
                245                 250                 255

Arg Trp Val Ala Val Arg Pro Arg Pro Asp Ala Leu Val Val Asn Ile
            260                 265                 270

Gly Asp Leu Phe Gln Ala Trp Ser Asn Asn Arg Tyr Lys Ser Val Glu
        275                 280                 285

His Lys Val Val Ala Asn Ala Lys Thr Asp Arg Leu Ser Val Ala Tyr
        290                 295                 300

Phe Leu Cys Pro Ser Tyr Asp Ser Leu Val Gly Thr Cys Gly Glu Pro
305                 310                 315                 320

Ser Pro Tyr Arg Ala Phe Thr Phe Gly Glu Tyr Arg Lys Lys Val Gln
                325                 330                 335

Glu Asp Val Arg Thr Thr Gly Lys Lys Ile Gly
                340                 345

<210> SEQ ID NO 31
<211> LENGTH: 22
<212> TYPE: DNA
<213> ORGANISM: Oryza sativa

<400> SEQUENCE: 31
atggaggagc acgactacga ct                                           22

<210> SEQ ID NO 32
<211> LENGTH: 23
<212> TYPE: DNA
<213> ORGANISM: Oryza sativa

<400> SEQUENCE: 32
tcctccatga tctgcttcct gta                                          23

<210> SEQ ID NO 33
<211> LENGTH: 23
<212> TYPE: DNA
<213> ORGANISM: Oryza sativa

<400> SEQUENCE: 33
agatactcac tccgtttcat gtt                                          23

<210> SEQ ID NO 34
<211> LENGTH: 23
<212> TYPE: DNA
<213> ORGANISM: Oryza sativa

<400> SEQUENCE: 34
gtagtgcggt gaaacaggat gcc                                          23
```

```
<210> SEQ ID NO 35
<211> LENGTH: 21
<212> TYPE: DNA
<213> ORGANISM: Oryza sativa

<400> SEQUENCE: 35
tgctccggac gccacaatct a                                        21

<210> SEQ ID NO 36
<211> LENGTH: 24
<212> TYPE: DNA
<213> ORGANISM: Oryza sativa

<400> SEQUENCE: 36
cgagatgata ctttgaccaa caat                                     24

<210> SEQ ID NO 37
<211> LENGTH: 21
<212> TYPE: DNA
<213> ORGANISM: Oryza sativa

<400> SEQUENCE: 37
aactcatggc gatctcttac c                                        21

<210> SEQ ID NO 38
<211> LENGTH: 28
<212> TYPE: DNA
<213> ORGANISM: Oryza sativa

<400> SEQUENCE: 38
cgagcaaacg atgtggaagg gctacagg                                 28

<210> SEQ ID NO 39
<211> LENGTH: 28
<212> TYPE: DNA
<213> ORGANISM: Oryza sativa

<400> SEQUENCE: 39
tggctcaggc ggagtgagta cattgtcg                                 28

<210> SEQ ID NO 40
<211> LENGTH: 22
<212> TYPE: DNA
<213> ORGANISM: Oryza sativa

<400> SEQUENCE: 40
ccccacatcc ctgacaaggc tc                                       22

<210> SEQ ID NO 41
<211> LENGTH: 22
<212> TYPE: DNA
<213> ORGANISM: Oryza sativa

<400> SEQUENCE: 41
ctattcatgg tcgtcatcgt cc                                       22

<210> SEQ ID NO 42
<211> LENGTH: 22
<212> TYPE: DNA
<213> ORGANISM: Oryza sativa

<400> SEQUENCE: 42
tgagcgcgct ggtgacggcg ga                                       22
```

```
<210> SEQ ID NO 43
<211> LENGTH: 21
<212> TYPE: DNA
<213> ORGANISM: Oryza sativa

<400> SEQUENCE: 43
cttgatttgt aggcagcctt c                                              21

<210> SEQ ID NO 44
<211> LENGTH: 21
<212> TYPE: DNA
<213> ORGANISM: Oryza sativa

<400> SEQUENCE: 44
tcggtggagg ataacttcgg c                                              21

<210> SEQ ID NO 45
<211> LENGTH: 21
<212> TYPE: DNA
<213> ORGANISM: Oryza sativa

<400> SEQUENCE: 45
tgggttagcg acaggtggtg g                                              21

<210> SEQ ID NO 46
<211> LENGTH: 22
<212> TYPE: DNA
<213> ORGANISM: Oryza sativa

<400> SEQUENCE: 46
atggaggagc acgactacga ct                                             22

<210> SEQ ID NO 47
<211> LENGTH: 23
<212> TYPE: DNA
<213> ORGANISM: Oryza sativa

<400> SEQUENCE: 47
tcctccatga tctgcttcct gta                                            23

<210> SEQ ID NO 48
<211> LENGTH: 24
<212> TYPE: DNA
<213> ORGANISM: Oryza sativa

<400> SEQUENCE: 48
gacgacgtgc ttcctgcggc tcaa                                           24

<210> SEQ ID NO 49
<211> LENGTH: 22
<212> TYPE: DNA
<213> ORGANISM: Oryza sativa

<400> SEQUENCE: 49
cttcctgcac cttcttcctg ta                                             22

<210> SEQ ID NO 50
<211> LENGTH: 20
<212> TYPE: DNA
<213> ORGANISM: Oryza sativa

<400> SEQUENCE: 50
acgggagctt ctacgcgagt                                                20
```

<210> SEQ ID NO 51
<211> LENGTH: 23
<212> TYPE: DNA
<213> ORGANISM: Oryza sativa

<400> SEQUENCE: 51
tcaaatctgc agagcctgtc gtc        23

<210> SEQ ID NO 52
<211> LENGTH: 22
<212> TYPE: DNA
<213> ORGANISM: Oryza sativa

<400> SEQUENCE: 52
gtgctgcggc ggatggtggt gg        22

<210> SEQ ID NO 53
<211> LENGTH: 23
<212> TYPE: DNA
<213> ORGANISM: Oryza sativa

<400> SEQUENCE: 53
cttcgtcgcg gcctcatcgt tgg        23

<210> SEQ ID NO 54
<211> LENGTH: 19
<212> TYPE: DNA
<213> ORGANISM: Oryza sativa

<400> SEQUENCE: 54
atgtcgaggc tggccaggg        19

<210> SEQ ID NO 55
<211> LENGTH: 22
<212> TYPE: DNA
<213> ORGANISM: Oryza sativa

<400> SEQUENCE: 55
catacgagga aattactgag gc        22

<210> SEQ ID NO 56
<211> LENGTH: 21
<212> TYPE: DNA
<213> ORGANISM: Oryza sativa

<400> SEQUENCE: 56
ctccgatcca acgacacctc t        21

<210> SEQ ID NO 57
<211> LENGTH: 20
<212> TYPE: DNA
<213> ORGANISM: Oryza sativa

<400> SEQUENCE: 57
agccagcgcc tcgtcctgat        20

<210> SEQ ID NO 58
<211> LENGTH: 28
<212> TYPE: DNA
<213> ORGANISM: Oryza sativa

<400> SEQUENCE: 58
tctccaagct catgtggtcc gagggcta        28

<210> SEQ ID NO 59
<211> LENGTH: 28
<212> TYPE: DNA
<213> ORGANISM: Oryza sativa

<400> SEQUENCE: 59
tggagcacga aggtgaagaa gcccgagt                                    28

<210> SEQ ID NO 60
<211> LENGTH: 20
<212> TYPE: DNA
<213> ORGANISM: Oryza sativa

<400> SEQUENCE: 60
cctcgtgccc ctatcaactt                                             20

<210> SEQ ID NO 61
<211> LENGTH: 20
<212> TYPE: DNA
<213> ORGANISM: Oryza sativa

<400> SEQUENCE: 61
gacactaaag cgcccggtat                                             20

<210> SEQ ID NO 62
<211> LENGTH: 28
<212> TYPE: DNA
<213> ORGANISM: Artificial Sequence
<220> FEATURE:
<223> OTHER INFORMATION: PCR primer

<400> SEQUENCE: 62
agcggatcca tggaggagca cgactacg                                    28

<210> SEQ ID NO 63
<211> LENGTH: 28
<212> TYPE: DNA
<213> ORGANISM: Artificial Sequence
<220> FEATURE:
<223> OTHER INFORMATION: PCR primer

<400> SEQUENCE: 63
aatggatccc tatcgggttc gaaagcgg                                    28

<210> SEQ ID NO 64
<211> LENGTH: 22
<212> TYPE: DNA
<213> ORGANISM: Artificial Sequence
<220> FEATURE:
<223> OTHER INFORMATION: PCR primer

<400> SEQUENCE: 64
ttggatccat gccggccttc gc                                          22

<210> SEQ ID NO 65
<211> LENGTH: 23
<212> TYPE: DNA
<213> ORGANISM: Artificial Sequence
<220> FEATURE:
<223> OTHER INFORMATION: PCR primer

<400> SEQUENCE: 65
cgggatcctt attgtactga aga                                         23

-continued

```
<210> SEQ ID NO 66
<211> LENGTH: 30
<212> TYPE: DNA
<213> ORGANISM: Artificial Sequence
<220> FEATURE:
<223> OTHER INFORMATION: PCR primer

<400> SEQUENCE: 66
tcggatccct actccatgat ctgcttcctg                                  30

<210> SEQ ID NO 67
<211> LENGTH: 30
<212> TYPE: DNA
<213> ORGANISM: Artificial Sequence
<220> FEATURE:
<223> OTHER INFORMATION: PCR primer

<400> SEQUENCE: 67
tttggatcct tattcctgca ccttcttcct                                  30

<210> SEQ ID NO 68
<211> LENGTH: 343
<212> TYPE: PRT
<213> ORGANISM: Oryza sativa

<400> SEQUENCE: 68

Met Pro Ala Ile Ala Asp Cys Ala Ala Asp Pro Leu Ala Asp Ser
1               5                  10                  15

Tyr Tyr Thr Leu Leu Arg Leu Gly Gly Asp Asp Asp Asp Ala Cys
            20                  25                  30

Thr Lys Val Thr Thr Thr Pro Gln Pro Val Ser Glu Cys Glu Leu Pro
        35                  40                  45

Met Ile Asp Val Gly Cys Leu Thr Ala Pro Thr Gly Ala Ala Ala
    50                  55                  60

Ala Ala Val Gly Gln Gln His Gln Ala Glu Glu Arg Ala Ala Cys Ala
65                  70                  75                  80

Ala Ala Ile Ala Ala Ala Ala Glu Trp Gly Phe Phe Gln Val Val
                85                  90                  95

Asn His Gly Val Ala Gln Glu Leu Leu Glu Ala Met Arg Arg Glu Gln
            100                 105                 110

Ala Arg Leu Phe Arg Leu Pro Phe Glu Ala Lys Ser Ser Ala Gly Leu
        115                 120                 125

Leu Asn Asp Ser Tyr Arg Trp Gly Thr Pro Thr Ala Thr Ser Leu Arg
130                 135                 140

Gln Leu Ser Trp Ser Glu Ala Phe His Leu Pro Leu Ala Gly Ile Ser
145                 150                 155                 160

Gly Lys Ser Cys Asn Tyr Gly Asp Leu Thr Ser Leu Arg Asp Val Thr
                165                 170                 175

Arg Glu Val Ala Asp Ala Met Ser Arg Leu Ala Arg Ala Leu Ala Arg
            180                 185                 190

Val Leu Ala Glu Ser Leu Leu Gly His Ala Ala Gly Glu Arg Phe Pro
        195                 200                 205

Glu Gly Cys Asp Asp Ala Thr Cys Phe Leu Arg Leu Asn Arg Tyr Pro
    210                 215                 220

Pro Cys Pro Phe Pro Pro Asp Ala Phe Gly Leu Val Pro His Thr
225                 230                 235                 240

Asp Ser Asp Phe Leu Thr Val Leu Cys Gln Asp His Val Gly Leu
                245                 250                 255

Gln Leu Met Lys Gly Ser Arg Trp Val Ala Val Lys Pro Ile Pro Gly
```

```
                    260                 265                 270
Ala Leu Ile Val Asn Ile Gly Asp Leu Phe Gln Ala Trp Ser Asn Asn
            275                 280                 285

Arg Tyr Lys Ser Val Glu His Arg Val Met Thr Asn Ala Thr Thr Glu
        290                 295                 300

Arg Tyr Ser Val Ala Tyr Phe Leu Cys Pro Ser Tyr Asp Ser Pro Ile
305                 310                 315                 320

Gly Thr Cys Arg Glu Pro Ser Pro Tyr Lys Ala Phe Thr Phe Gly Glu
                325                 330                 335

Tyr Arg Arg Arg Val Gln Glu
                340

<210> SEQ ID NO 69
<211> LENGTH: 353
<212> TYPE: PRT
<213> ORGANISM: Oryza sativa

<400> SEQUENCE: 69

Met Pro Ala Ile Ala Asp Cys Ala Ala Asp Pro Pro Leu Ala Asp Ser
1               5                   10                  15

Tyr Tyr Thr Leu Leu Arg Leu Gly Gly Asp Asp Asp Asp Asp Ala Cys
            20                  25                  30

Thr Lys Val Thr Thr Thr Pro Gln Pro Val Ser Glu Cys Glu Leu Pro
        35                  40                  45

Met Ile Asp Val Gly Cys Leu Thr Ala Pro Thr Gly Ala Ala Ala Ala
    50                  55                  60

Ala Ala Val Gly Gln Gln His Gln Ala Glu Glu Arg Ala Ala Cys Ala
65                  70                  75                  80

Ala Ala Ile Ala Ala Ala Ala Glu Trp Gly Phe Phe Gln Val Val
                85                  90                  95

Asn His Gly Val Ala Gln Glu Leu Leu Glu Ala Met Arg Arg Glu Gln
            100                 105                 110

Ala Arg Leu Phe Arg Leu Pro Phe Glu Ala Lys Ser Ser Ala Gly Leu
        115                 120                 125

Leu Asn Asp Ser Tyr Arg Trp Gly Thr Pro Thr Ala Thr Ser Leu Arg
130                 135                 140

Gln Leu Ser Trp Ser Glu Ala Phe His Leu Pro Leu Ala Gly Ile Ser
145                 150                 155                 160

Gly Lys Ser Cys Asn Tyr Gly Asp Leu Thr Ser Leu Arg Asp Val Thr
                165                 170                 175

Arg Glu Val Ala Asp Ala Met Ser Arg Leu Ala Arg Ala Leu Ala Arg
            180                 185                 190

Val Leu Ala Glu Ser Leu Leu Gly His Ala Ala Gly Glu Arg Phe Pro
        195                 200                 205

Glu Gly Cys Asp Asp Ala Thr Cys Phe Leu Arg Leu Asn Arg Tyr Pro
    210                 215                 220

Pro Cys Pro Phe Pro Pro Asp Asp Ala Phe Gly Leu Val Pro His Thr
225                 230                 235                 240

Asp Ser Asp Phe Leu Thr Val Leu Cys Gln Asp His Val Gly Gly Leu
                245                 250                 255

Gln Leu Met Lys Gly Ser Arg Trp Val Ala Val Lys Pro Ile Pro Gly
            260                 265                 270

Ala Leu Ile Val Asn Ile Gly Asp Leu Phe Gln Ala Trp Ser Asn Asn
        275                 280                 285

Arg Tyr Lys Ser Val Glu His Arg Val Met Thr Asn Ala Thr Thr Glu
```

```
                290             295             300
Arg Tyr Ser Val Ala Tyr Phe Leu Cys Pro Ser Tyr Asp Ser Pro Ile
305             310             315             320

Gly Thr Cys Arg Glu Pro Ser Pro Tyr Lys Ala Phe Thr Phe Gly Glu
            325             330             335

Tyr Arg Arg Arg Val Gln Glu Asp Val Lys Lys Thr Gly Lys Lys Thr
            340             345             350

Gly

<210> SEQ ID NO 70
<211> LENGTH: 102
<212> TYPE: PRT
<213> ORGANISM: Oryza sativa

<400> SEQUENCE: 70

Glu Thr Cys Phe Leu Arg Leu Asn Arg Tyr Pro Pro Cys Ala Met Ala
1               5                  10                  15

Met Gly Gly Phe Gly Leu Cys Pro His Thr Asp Ser Asp Leu Leu Thr
            20                  25                  30

Ile Val His Gln Gln Asp Thr Val Gly Gly Leu Gln Leu Leu Lys
        35                  40                  45

Gly Gly Arg Trp Val Ala Val Lys Pro Ser Pro Ser Thr Leu Ile Val
    50                  55                  60

Asn Val Gly Asp Leu Leu Gln Ala Trp Ser Asn Asp Val Tyr Lys Ser
65                  70                  75                  80

Val Glu His Arg Val Met Ala Asn Ala Thr Leu Glu Arg Phe Ser Met
                85                  90                  95

Ala Phe Phe Leu Cys Pro
            100

<210> SEQ ID NO 71
<211> LENGTH: 100
<212> TYPE: PRT
<213> ORGANISM: Oryza sativa

<400> SEQUENCE: 71

Thr Thr Cys Phe Leu Arg Leu Asn Arg Tyr Pro Ala Cys Pro Phe Ala
1               5                  10                  15

Ala Asp Thr Phe Gly Leu Val Pro His Thr Asp Ser Asp Phe Leu Thr
            20                  25                  30

Val Leu Cys Gln Asp Gln Val Gly Gly Leu His Leu Met Lys Asp Ser
        35                  40                  45

Arg Trp Val Ala Val Arg Pro Arg Pro Asp Ala Leu Val Val Asn Ile
    50                  55                  60

Gly Asp Leu Phe Gln Ala Trp Ser Asn Asn Arg Tyr Lys Ser Val Glu
65                  70                  75                  80

His Lys Val Val Ala Asn Ala Lys Thr Asp Arg Leu Ser Val Ala Tyr
                85                  90                  95

Phe Leu Cys Pro
            100

<210> SEQ ID NO 72
<211> LENGTH: 109
<212> TYPE: PRT
<213> ORGANISM: Oryza sativa

<400> SEQUENCE: 72

Ser Asp Ser Ile Leu Arg Val Asn His Tyr Pro Pro Arg Pro Asp Gln
```

```
                 1               5                  10                 15
Leu Gly Gly Gly Gly Pro Asn Leu Thr Gly Phe Gly Glu His Thr
                20                 25                 30

Asp Pro Gln Ile Ile Ser Val Leu Arg Ser Asn Gly Ala Pro Gly Leu
                35                 40             45

Glu Ile Ser Leu Arg Asp Gly Ala Trp Ala Ser Val Pro His Asp Gly
 50                 55                 60

Asp Gly Asp Ser Phe Phe Val Asn Val Gly Asp Thr Leu Gln Val Leu
 65                 70                 75                 80

Thr Asn Gly Arg Phe Arg Ser Val Lys His Arg Val Val Val Asn Ser
                85                 90                 95

Glu Lys Ser Arg Val Ser Met Val Phe Phe Gly Gly Pro
                100                105
```

<210> SEQ ID NO 73
<211> LENGTH: 114
<212> TYPE: PRT
<213> ORGANISM: Oryza sativa

<400> SEQUENCE: 73

```
Ser Asp Glu Met Leu Arg Val Asn His Tyr Pro Pro Cys Leu Leu Pro
 1               5                  10                 15

Pro Gly Arg Asp Arg Asp Glu Cys Gly Val Thr Gly Phe Gly Glu His
                20                 25                 30

Thr Asp Pro Gln Ile Ile Ser Val Leu Arg Ser Asn Cys Thr Ala Gly
                35                 40                 45

Leu Gln Ile Leu Leu Arg Gly Asp Tyr Ser Ser Pro Ala Arg Trp Val
 50                 55                 60

Pro Val Pro Pro Asp Pro Asp Ser Phe Phe Val Asn Val Gly Asp Ser
 65                 70                 75                 80

Leu Gln Val Leu Thr Asn Gly Arg Phe Arg Ser Val Lys His Arg Val
                85                 90                 95

Leu Ala Pro Glu Gly Glu Ser Arg Leu Ser Val Ile Tyr Phe Gly
                100                105                110

Gly Pro
```

<210> SEQ ID NO 74
<211> LENGTH: 101
<212> TYPE: PRT
<213> ORGANISM: Oryza sativa

<400> SEQUENCE: 74

```
Ala Thr Cys Phe Leu Arg Leu Asn Arg Tyr Pro Pro Cys Pro Phe Pro
 1               5                  10                 15

Pro Asp Asp Ala Phe Gly Leu Val Pro His Thr Asp Ser Asp Phe Leu
                20                 25                 30

Thr Val Leu Cys Gln Asp His Val Gly Gly Leu Gln Leu Met Lys Gly
                35                 40                 45

Ser Arg Trp Val Ala Val Lys Pro Ile Pro Gly Ala Leu Ile Val Asn
 50                 55                 60

Ile Gly Asp Leu Phe Gln Ala Trp Ser Asn Asn Arg Tyr Lys Ser Val
 65                 70                 75                 80

Glu His Arg Val Met Thr Asn Ala Thr Thr Glu Arg Tyr Ser Val Ala
                85                 90                 95

Tyr Phe Leu Cys Pro
                100
```

```
<210> SEQ ID NO 75
<211> LENGTH: 107
<212> TYPE: PRT
<213> ORGANISM: Oryza sativa

<400> SEQUENCE: 75

Ser Asp Ser Val Leu Arg Val Asn His Tyr Pro Pro His Pro Glu Leu
1               5                   10                  15

Lys Gln Gln Gly His Gly Arg Leu Thr Gly Phe Gly Glu His Thr Asp
                20                  25                  30

Pro Gln Ile Ile Ser Val Leu Arg Ser Asn Asp Thr Ser Gly Leu Glu
            35                  40                  45

Ile Ser Leu Arg Asp Gly Ser Trp Ala Ser Val Pro Pro Asp Arg Lys
        50                  55                  60

Ser Phe Phe Val Asn Val Gly Asp Val Leu Gln Pro Gly Gly Arg Ile
65                  70                  75                  80

Lys Leu Glu Glu Leu Gln Gly Phe Leu His Ala Val Ser Leu Arg Ser
                85                  90                  95

Arg Ala Thr Arg Glu Ala Thr Arg Ser Arg Pro
                100                 105
```